US006261551B1

(12) United States Patent
Wilson et al.

(10) Patent No.: US 6,261,551 B1
(45) Date of Patent: *Jul. 17, 2001

(54) RECOMBINANT ADENOVIRUS AND ADENO-ASSOCIATED VIRUS, CELL LINES, AND METHODS OF PRODUCTION AND USE THEREOF

(75) Inventors: James M. Wilson, Gladwyne, PA (US); Krishna J. Fisher, New Orleans, LA (US); Guang-Ping Gao, Havertown, PA (US)

(73) Assignee: The Trustees of the University of Pennsylvania, Philadelphia, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 08/973,334

(22) PCT Filed: Jun. 4, 1996

(86) PCT No.: PCT/US96/10245

§ 371 Date: Dec. 5, 1997

§ 102(e) Date: Dec. 5, 1997

(87) PCT Pub. No.: WO96/39530

PCT Pub. Date: Dec. 12, 1996

Related U.S. Application Data

(63) Continuation-in-part of application No. 08/549,489, filed on Oct. 27, 1995, which is a continuation-in-part of application No. 08/462,014, filed on Jun. 5, 1995, now Pat. No. 5,756,283.

(51) Int. Cl.$^7$ .................. A61K 48/00; C12N 15/861; C12N 15/63; C12N 5/10

(52) U.S. Cl. .................. 424/93.2; 424/93.6; 435/320.1; 435/69.1; 435/325; 435/366; 435/235.1; 435/455; 435/456; 435/457; 435/463; 435/369; 435/375

(58) Field of Search .................. 435/69.1, 325, 435/366, 235.1, 320.1, 455, 456, 457, 463, 369, 375; 424/93.2, 93.6

(56) References Cited

U.S. PATENT DOCUMENTS

| | | | |
|---|---|---|---|
| 4,797,368 | 1/1989 | Carter et al. | 435/320.1 |
| 4,920,209 | 4/1990 | Davis et al. | 435/235.1 |
| 5,139,941 | 8/1992 | Muzyczka et al. | 435/456 |
| 5,173,414 | 12/1992 | Lebkowski et al. | 435/91.4 |
| 5,252,479 | 10/1993 | Srivastava | 435/235.1 |
| 5,354,678 | 10/1994 | Lebkowski et al. | 435/463 |
| 5,436,146 | 7/1995 | Shenk et al. | 435/457 |
| 5,543,328 | 8/1996 | McClelland et al. | 435/320.1 |
| 5,604,090 | 2/1997 | Alexander et al. | 435/5 |
| 5,622,856 | 4/1997 | Natsoulis | 435/325 |
| 5,707,618 | * 1/1998 | Armentano et al. | 424/93.21 |
| 5,753,500 | 5/1998 | Shenk et al. | 435/320.1 |
| 5,756,283 | * 5/1998 | Wilson et al. | 435/5 |

FOREIGN PATENT DOCUMENTS

| | | |
|---|---|---|
| 27902/92 | 4/1993 | (AU) . |
| WO91/18088 | 11/1991 | (WO) . |
| WO93/19191 | 9/1993 | (WO) . |
| WO93/24641 | 12/1993 | (WO) . |
| WO94/12649 | 6/1994 | (WO) . |
| WO94/13788 | 6/1994 | (WO) . |
| WO94/17832 | 8/1994 | (WO) . |
| WO94/20517 | 9/1994 | (WO) . |
| WO94/24299 | 10/1994 | (WO) . |
| WO94/26914 | 11/1994 | (WO) . |
| WO94/28152 | 12/1994 | (WO) . |
| WO94/28157 | 12/1994 | (WO) . |
| WO94/28938 | 12/1994 | (WO) . |
| WO95/00655 | 1/1995 | (WO) . |
| WO95/02697 | 1/1995 | (WO) . |
| WO95/06743 | 3/1995 | (WO) . |
| WO95/10623 | 4/1995 | (WO) . |
| WO95/13392 | 5/1995 | (WO) . |
| WO95/20671 | 8/1995 | (WO) . |
| WO95/27071 | 10/1995 | (WO) . |
| WO95/33824 | 12/1995 | (WO) . |
| WO95/34671 | 12/1995 | (WO) . |
| WO96/12030 | 4/1996 | (WO) . |
| WO96/13596 | 5/1996 | (WO) . |
| WO96/13597 | 5/1996 | (WO) . |
| WO96/13598 | 5/1996 | (WO) . |
| WO96/14061 | 5/1996 | (WO) . |
| WO96/18418 | 6/1996 | (WO) . |
| WO96/22378 | 7/1996 | (WO) . |

OTHER PUBLICATIONS

Ross et al., Human Gene Therapy, vol. 7, pp. 1781–1790, Sep. 10, 1996.*

Orkin et al., "Report and Recommendations of the Panel to Assess the NIH Investment in Research on Gene Therapy", Dec. 7, 1995.*

Verma et al., Nature, vol. 389, pp. 239–242, Sep. 18, 1997.*

I. Alexander et al, "DNA–Damaging Agents Greatly Increase the Transduction of Nondividing Cells by Adeno–Associated Virus Vectors", *J. Virol.*, 68(12):8282–8287 (Dec., 1994).

F. Collins, "Cystic Fibrosis: Molecular Biology and Therapeutic Implications", *Science*, 256:774–779 (May 8, 1992).

B. Davidson et al, "A Model System for in vivo Gene Transfer into the Central Nervous System Using an Adenoviral Vector", *Nature Genetics*, 3:219–223 (Mar., 1993).

(List continued on next page.)

*Primary Examiner*—David Guzo
(74) *Attorney, Agent, or Firm*—Howson and Howson

(57) ABSTRACT

An adenovirus E1/E4 expressing packaging cell line is provided, which permits the generation of recombinant adenoviruses deleted in both gene regions. A method for enhancing the efficiency of transduction of a recombinant AAV into a target cell is provided by infecting a target cell with a recombinant AAV comprising a selected transgene under the control of regulatory sequences. The infected cell is contacted with an agent which facilitates the conversion of single stranded recombinant virus to its double stranded form.

25 Claims, 11 Drawing Sheets

OTHER PUBLICATIONS

M. Eloit et al, "Construction of a Defective Adenovirus Vector Expressing the Pseudorabies Virus Glycoprotein gp50 and its Use as a Live Vaccine", *J. Gen. Virol.*, 71(10):2425–2431 (Oct., 1990).

J. Engelhardt et al, "Ablation of E2A in Recombinant Adenoviruses Improves Transgene Persistence and Decreases Inflammatory Response in Mouse Liver", *Proc. Natl. Acad. Sci. USA*, 91:6196–6200 (Jun., 1994) [Engelhardt I].

J. Engelhardt et al, "Adenovirus–Mediated Transfer of the CFTR Gene to Lung of Nonhuman Primates: Biological Efficacy Study", *Human Genet. Ther.*, 4:759–769 (Dec., 1993) [Engelhardt II].

J. Engelhardt et al, "Prolonged Transgene Expression in Cotton Rat Lung with Recombinant Adenoviruses Defective in E2a", *Human Gene Ther.*, 5:1217–1229 (Oct., 1994) [Engelhardt III].

K. Fisher et al, "Biochemical and Functional Analysis of an Adenovirus–Based Ligand Complex for Gene Transfer", *Biochem. J.*, 299:49–58 (Apr. 1, 1994) [Fisher I].

M. Grable et al, "Adenovirus Type 5 Packaging Domain is Composed of a Repeated Element that is Functionally Redundant", *J. Virol.*, 64(5):2047–2056 (May, 1990).

P. Hearing et al, "Identification of a Repeated Sequence Element Required for Efficient Encapsidation of the Adenovirus Type 5 Chromosome", *J. Virol.*, 61(8):2555–2558 (Aug., 1987).

M. Horwitz, "Adenoviridae and Their Replication", *Virology*, 2d edition, ed. B. N. Fields, Raven Press, Ltd., New York, Chapter 60, pp. 1679–1721 (1990).

S. Ishibashi et al, "Hypercholesterolemia in Low Density Lipoprotein Receptor Knockout Mice and its Reversal by Adenovirus–mediated Gene Delivery", *J. Clin. Invest.*, 92:883–893 (Aug., 1993).

M. Kaplitt et al, "Long–term Gene Expression and Phenotypic Correction Using Adeno–associated Virus Vectors in the Mammalian Brain," *Nature Genetics*, 8:148–154 (Oct., 1994).

K. Kozarsky et al, "In Vivo Correction of Low Density Lipoprotein Receptor Deficiency in the Watanabe Heritable Hyperlipidemic Rabbit with Recombinant Adenoviruses", *J. Biol. Chem.*, 5269(18):13695–13702 (May 6, 1994) [Kozarsky I].

K. Kozarsky et al, "Adenovirus–Mediated Correction of the Genetic Defect in Hepatocytes from Patients with Familial Hypercholesterolemia", *Somatic Cell and Molecular Genetics*, 19(5):449–458 (Sep., 1993) [Kozarsky II].

K. Kozarsky et al, "Gene Therapy: Adenovirus Vectors", *Curr. Opin. Genet. Devel.*, 3:499–503 (Mar., 1993) [Kozarsky III].

C. Laughlin et al, "Cloning of infectious adeno–associated virus genomes in bacterial plasmids", *Gene*, 23:65–73 (Jul., 1983).

J. Logan et al, "Adenovirus Tripartite Leader Sequence Enhances Translation of mRNAs Late After Infection", *Proc. Natl. Acad. Sci. USA*, 81:3655–3659 (Jun., 1984).

B. Roessler et al, "Adenoviral–mediated Gene Transfer to Rabbit Synovium In Vivo", *J. Clin. Invest.*, 92:1085–1092 (Aug., 1993).

D. Russell et al, "Adeno–associated virus vectors preferentially transduce cells in S phase", *Proc. Natl. Acad. Sci. USA*, 91:8915–8919 (Sep., 1994) [Russell I].

M. Rosenfeld et al, "In Vivo Transfer of the Human Cystic Fibrosis Transmembrane Conductance Regulator Gene to the Airway Epithelium", *Cell*, 68:143–155 (Jan. 10, 1992).

R. Samulski et al, "Helper–Free Stocks of Recombinant Adeno–Associated Viruses: Normal Integration Does Not Require Viral Gene Expression", *J. Virol.*, 63(9):3822–3828 (Sep., 1989).

T. Shenk et al, "Genetic Analysis of Adenoviruses", *Current Topics in Microbiol. and Immunol.*, 111:1–39 (1984).

W. Smythe et al, "Successful Adenovirus–Mediated Gene Transfer in an In Vivo Model of Human Malignant Mesothelioma", *Ann. Thorac. Surg.*, 57(6):1395–1401 (Jun., 1994).

R. Spessot et al, "Cloning of the Herpes Simplex Virus ICP4 Gene in an Adenovirus Vector: Effects on Adenovirus Gene Expression and Replication", *Virol.*, 168:378–387 (1989).

P. Van Der Vliet et al, "Thermolabile DNA Binding Proteins from Cells Infected with a Temperature–Sensitive Mutant of Adenovirus Defective in Viral DNA Synthesis", *J. Virol.*, 15(2):348–354 (Feb., 1975).

J. Wilson et al, "Vehicles for gene therapy", *Nature*, 365:691–692 (Oct. 21, 1993) [Wilson I].

Y. Yang et al, "MHC Class I–Restricted Cytotoxic T Lymphocytes to Viral Antigens Destroy Hepatocytes in Mice Infected with E1–Deleted Recombinant Adenoviruses", *Immunity*, 1:433–442 (Aug., 1994) [Yang I].

Y. Yang et al, "Cellular Immunity to Viral Antigens Limits E1–Deleted Adenoviruses for Gene Therapy", *Proc. Natl. Acad. Sci. USA*, 91:4407–4411 (May, 1994) [Yang II].

Y. Yang et al, "Inactivation of E2a in Recombinant Adenoviruses Improves the Prospect for Gene Therapy in Cystic Fibrosis", *Nature Genetics*, 7:362–369 (Jul, 1994) [Yang III].

D. Russell et al, "DNA Synthesis and topoisomerase Inhibitors Increase Transduction by Adeno–Associated Virus Vectors", *Proc. Natl. Acad. Sci. USA*, 92:5719–5723 (Jun. 5, 1995) [Russell II].

P. Hermonat et al, "Use of Adeno–Associated Virus as a Mammalian DNA Cloning Vector: Transduction of Neomycin Resistance into Mammalian Tissue Culture Cells", *Proc. Natl. Acad. Sci. USA*, 81:6466–6470 (Oct., 1984).

K. Fisher et al, "Transduction with Recombinant Adeno–Associated Virus for Gene Therapy is Limited by Leading–Strand Synthesis", *J. Virol.*, 70(1):520–532 (Jan., 1996) [Fisher II].

M. Weitzman et al, "Recruitment of Wild–Type and Recombinant Adeno–Associated Virus into Adenovirus Replication Centers", *J. Virol.*, 70(3):1845–1854 (Mar., 1996).

P. Nahreini et al, "Cloning and Integration of DNA Fragments in Human Cells via the Inverted Terminal Repeats of the Adeno–Associated Virus 2 Genome", *Gene*, 119(2):265–272 (1992).

B. Carter, "The Growth Cycle of Adeno–Associated Virus", in *CRC Handbook of Parvoviruses*, ed. P. Tijssen, vol. I, pp. 155–168 (1990).

S. McLaughlin et al, "Adeno–Associated Virus General Transduction Vectors: Analysis of Proviral Structures", *J. Virology*, 62(6):1963–1973 (Jun., 1988).

W. Gunzburg et al, "Virus Vector Design in Gene Therapy", *Molecular Medicine Today*, 1(9):410–417 (Dec., 1995).

J. Schlehofer et al, "Vaccinia Virus, Herpes Simplex Virus, and Carcinogens Induce DNA Amplification in a Human Cell Line and Support Replication of a Helpervirus Dependent Parvovirus", *Virology*, 152:110–117 (May, 1986).

B. Yakobson et al, "Replication of Adeno–Associated Virus in Synchronized Cells without the Addition of a Helper Virus", *J. Virology*, 61(4):972–981 (Apr., 1987).

R. Boucher et al, "Clinical Protocol—Gene Therapy for Cystic Fibrosis Using E1–Deleted Adenovirus: A Phase I Trial in the Nasal Cavity The University of North Carolina at Chapel Hill", *Human Gene Ther.*, 5:615–639 (May, 1994).

J. Engelhardt et al, "Direct Gene Transfer of Human CFTR into Human Bronchial Epithelia of Xenografts with E1–deleted Adenoviruses", *Nat. Genet.*, 4:27–34 (May, 1993) [Engelhardt IV].

J. Goldstein et al, "Defective Lipoprotein Receptors and Atherosclerosis", *New Engl. J. Med.*, 309(5):288–296 (Aug., 1983).

M. Goldman et al, "Expression of $\alpha_v\beta_5$ Integrin Is Necessary for Efficient Adenovirus–Mediated Gene Transfer in the Human Airway", *J. Virol.*, 69:5951–5958 (Oct., 1995) [Goldman I].

M. Goldman et al, "Transfer of the CFTR Gene to the Lung of Nonhuman Primates with E1–Deleted, E2a–Defective Recombinant Adenoviruses: A Preclinical Toxicology Study", *Human Gene Therapy*, 6:839–851 (Jul., 1995) [Goldman II].

M. Goldman et al, "Gene therapy in a xenograft model of cystic fibrosis lung corrects chloride transport more effectively than the sodium defect", *Nature Genetics*, 9:126–131 (Feb., 1995) [Goldman III].

M. Grossman et al, "Towards Liver–Directed Gene Therapy: Retrovirus–Mediated Gene Transfer into Human Hepatocytes", *Somatic Cell and Molec. Genet.*, 17(6):601–607 (Nov., 1991).

B. Grubb et al, "Inefficient gene transfer by adenovirus vector to cystic fibrosis airway epithelia of mice and humans", *Nature*, 371:802–806 (Oct. 27, 1994).

S. Ishibashi et al, "Massive Xanthomatosis and Atherosclerosis i Cholesterol–fed Low Density Lipoprotein Receptor–negative Mice", *J. Clin. Invest.*, 93:1885–1893 (May, 1994) [Ishibashi I].

M. Knowles et al, "A Controlled Study of Adenoviral–Vector–Mediated Gene Transfer in the Nasal Epithelium of Patients with Cystic Fibrosis", *N. Engl. J. Med.*, 333(13):823–831 (Sep., 1995).

J. Pilewski et al, "Adenovirus–mediated gene transfer to human bronchial submucosal glands using xenografts", *Amer. J. Physiol: Lung, Cell and Mole Physiol.*, 268:L657–L665 (Apr., 1995) [Pilewski I].

J. Pilewski et al, "ICAM–1 Expression on Bronchial Epithelium after Recombinant Adenovirus Infection", *Am J. Respir. Cell Mol. Biol.*, 12:142–148 (Feb., 1995) [Pilewski II].

T. A. G. Smith et al, "Adenovirus mediated expression of therapeutic plasma levels of human factor IX in mice", *Nature Genetics*, 5:397–402 (Dec., 1993).

K. Tanzawa et al, "WHHL–Rabbit: A Low Density Lipoprotein Receptor–Deficient Animal Model for Familial Hypercholesterolemia", *FEBS Leters*, 118(1):81–84 (Aug., 1980).

Y. Watanabe et al, "Serial Inbreeding of Rabbits with Hereditary Hyperlipidemia (WHHL–Rabbit)", *Atherosclerosis*, 36:261–268 (Jan., 1980).

J. Wilson et al, "Correction of the Genetic Defect in Hepatocytes from the Watanabe Heritable Hyperlipidemic Rabbit", *Proc. Natl. Acad. Sci. USA*, 85:4421–4425 (Jun., 1988) [Wilson II].

J. Wilson et al, "Research Article—Transplantation of Allogeneic Hepatocytes into LDL Receptor Deficient Rabbits Leads to Transient Improvement in Hypercholesterolemia", *Clin. Biotechnology*, 3:21–26 (Feb. 28, 1991) [Wilson III].

J. Wilson et al, "A Novel Mechanism for Achieving Transgene Persistence in Vivo After Somatic Gene Transfer into Hepatocytes", *J. Biol. Chem.*, 267(16):11483–11489 (Jun., 1992) [Wilson IV].

C. Wu et al, "Targeting Genes: Delivery and Persistent Expression of a Foreign Gene Driven by Mammalian Regulatory Elements in Vivo", *J. Biol. Chem.*, 264(29):16985–16987 (Oct. 15, 1989).

Y. Yang et al, "Recombinant IL–12 Prevents Formation of Blocking IgA Antibodies to Recombinant Adenovirus and Allows Repeated Gene Therapy to Mouse Lung", *Nat. Med.*, 1(9):890–893 (Sep., 1995) [Yang IV].

Y. Yang et al, "Upregulation of Class I MHC Antigens by Interferon–$\gamma$ is Necessary for the T Cell–Mediated Elimination of Recombinant Adenovirus Infected Hepatocytes In Vivo", *Proc. Natl. Acad. Sci. USA*, 92:7257–7261 (Aug., 1995) [Yang V].

Y. Yang et al, "Cellular and Humoral Immune Responses to Viral Antigens Create Barriers to Lung–Directed Gene Therapy with Recombinant Adenoviruses", *J. Virol.*, 69(4):2004–2015 (Apr., 1995) [Yang VI].

Y. Yang et al, "Clearance of Adenovirus–Infected Hepatocytes by MHC Class I–Restricted CD4+ CTLs in Vivo", *J. Immunol.*, 155:2564–2570 (Jun., 1995) [Yang VII].

K. Berkner, "Development of Adenovirus Vectors for the Expression of Heterologous Genes", *BioTechniques*, 6(7):616–629 (1988) [Berkner I].

E. Bridge et al, "Redundant Control of Adenovirus Late Gene Expression by Early Region 4", *J. Virol.*, 63(2):631–638 (Feb., 1989) [Bridge I].

Y. Dai et al, "Cellular and Humoral Immune Responses to Adenoviral Vectors Containing Factor IX Gene: Tolerization of Factor IX and Vector Antigens Allows for Long–Term Expression", *Proc. Natl. Acad. Sci. USA*, 92:1401–1405 (Feb., 1995).

Q. Wang et al, "A Packaging Cell Line for Propagation of Recombinant Adenovirus Vectors Containing Two Lethal Gene–Region Deletions", *Gene Therapy*, 2:775–783 (Dec. 19, 1995).

R. Hirt et al, "Inducible Protein Expression Using a Glucocortocoid–Sensitive Vector", *Methods in Cell Biology*, 43:247–262 (1994).

D. Weinberg et al, "A Cell Line that Supports the Growth of a Defective Early Region 4 Deletion Mutant of Human Adenovirus Type 2", *Proc. Natl. Acad. Sci. USA*, 80:5383–5386 (Sep., 1983).

D. Armentano et al, "Characterization of an Adenovirus Gene Transfer Vector Containing an E4 Deletion", *Human Gene Therapy*, 6:1343–1353 (Oct., 1995).

E. Bridge et al, "Adenovirus Early Region 4 and Viral DNA Synthesis", *Virology*, 193:794–801 (1993) [Bridge II].

K. Berkner, "Expression of Heterologous Sequences in Adenoviral Vectors", *Current Topics in Microbiology and Immunology*, 158:39–66 (1992) [Berkner II].

K. Ohman et al, "Two Adenovirus Proteins with Redundant Activities in Virus Growth Facilitates Tripartite Leader mRNA Accumulation", *Virology*, 194:50–58 (1993).

J. Wilson et al, "Clinical Protocol—Gene Thearpy of Cystic Fibrosis Lung Disease Using E1 Deleted Adenoviruses: A Phase I Trial", *Human Gene Therapy*, 5:501–519 (1994) [Wilson V].

R. Crystal, "Transfer of Genes to Humans: Early Lessons and Obstacles to Success", *Science*, 270:404–409 (Oct. 20, 1995).

S. Karlsson, "Treatment of Genetic Defects in Hematopoietic Cell Function by Gene Transfer", *Blood*, 78(10):2481–2492 (Nov. 15, 1991).

J-Y. Dong et al, "Systematic Analysis of Repeated Gene Delivery into Animal Lungs with a Recombinant Adenovirus Vector", *Human Gene Therapy*, 7:319–331 (Feb. 10, 1996).

A. Scaria et al, "Complementation of a Human Adenovirus Early Region 4 Deletion Mutant in 293 Cells Using Adenovirus–Polylysine–DNA Complexes", *Gene Therapy*, 2:295–298 (1995).

E. Marshall, "Less Hype, More Biology Needed for Gene Therapy", *Science*, 270:1751 (Dec. 15, 1995) [Marshall I].

A. Coghlan, "Gene Dream Fades Away", *New Scientist*, 145:14–15 (Nov. 25, 1995).

E. Marshall, "Gene Therapy's Growing Pains", *Science*, 269:1050–1055 (Agu. 25, 1995) [Marshall II].

S. Orkin et al, "Report and Recommendations of the Panel to Assess the NIH Investment in Research on Gene Therapy", (Dec. 7, 1995).

* cited by examiner

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 3653 base pairs
      (B) TYPE: nucleic acid
      (C) STRANDEDNESS: double
      (D) TOPOLOGY: Not Relevant (ii) MOLECULE TYPE: cDNA (ix) FEATURE:

(A) NAME/KEY: CDS
       (B) LOCATION: 1521..2405

(xi) SEQUENCE DESCRIPTION: SEQ ID NO:1:

```
CTGCATGTGT CAGAGGTTTT CACCGTCATC ACCGAAACGC GCGAGGCAGC          50

AAGCTTGGCA GAAATGGTTG AACTCCCGAG AGTGTCCTAC ACCTAGGGGA         100

GAAGCAGCCA AGGGGTTGTT TCCCACCAAG GACGACCCGT CTGCGCACAA         150

ACGGATGAGC CCATCAGACA AAGACATATT CATTCTCTGC TGCAAACTTG         200

GCATAGCTCT GCTTTGCCTG GGGCTATTGG GGGAAGTTGC GGTTCGTGCT         250

CGCAGGGCTC TCACCCTTGA CTCTTTCAAT AATAACTCTT CTGTGCAAGA         300

TTACAATCTA AACAATTCGG AGAACTCGAC CTTCCTCCTG AGGCAAGGAC         350

CACAGCCAAC TTCCTCTTAC AAGCCGCATC GATTTTGTCC TTCAGAAATA         400

GAAATAAGAA TGCTTGCTAA AAATTATATT TTTACCAATA AGACCAATCC         450

AATAGGTAGA TTATTAGTTA CTATGTTAAG AAATGAATCA TTATCTTTTA         500

GTACTATTTT TACTCAAATT CAGAAGTTAG AAATGGGAAT AGAAAATAGA         550

AAGAGACGCT CAACCTCAAT TGAAGAACAG GTGCAAGGAC TATTGACCAC         600

AGGCCTAGAA GTAAAAAAGG GAAAAAAGAG TGTTTTTGTC AAAATAGGAG         650

ACAGGTGGTG GCAACCAGGG ACTTATAGGG GACCTTACAT CTACAGACCA         700

ACAGATGCCC CCTTACCATA TACAGGAAGA TATGACTTAA ATTGGGATAG         750

GTGGGTTACA GTCAATGGCT ATAAAGTGTT ATATAGATCC CTCCCCTTTC         800

GTGAAAGACT CGCCAGAGCT AGACCTCCTT GGTGTATGTT GTCTCAAGAA         850

AAGAAAGACG ACATGAAACA ACAGGTACAT GATTATATTT ATCTAGGAAC         900

AGGAATGCAC TTTTGGGGAA AGATTTTCCA TACCAAGGAG GGGACAGTGG         950

CTGGACTAAT AGAACATTAT TCTGCAAAAA CTTATGGCAT GAGTTATTAT        1000

GATTAGCCTT GATTTGCCCA ACCTTGCGGT TCCCAAGGCT TAAGTAAGTT        1050

TTTGGTTACA AACTGTTCTT AAAACAAGGA TGTGAGACAA GTGGTTTCCT        1100

GACTTGGTTT GGTATCAAAG GTTCTGATCT GAGCTCTGAG TGTTCTATTT        1150

TCCTATGTTC TTTTGGAATT TATCCAAATC TTATGTAAAT GCTTATGTAA        1200

ACCAAGATAT AAAAGAGTGC TGATTTTTTG AGTAAACTTG CAACAGTCCT        1250

AACATTCACC TCTTGTGTGT TTGTGTCTGT TCGCCATCCC GTCTCCGCTC        1300

GTCACTTATC CTTCACTTTC CAGAGGGTCC CCCCGCAGAC CCCGGCGACC        1350

CTCAGGTCGG CCGACTGCGG CAGCTGGCGC CCGAACAGGG ACCCTCGGAT        1400

AAGTGACCCT TGTCTTTATT TCTACTATTT TGTGTTCGTC TTGTTTTGTC        1450

TCTATCTTGT CTGGCTATCA TCACAAGAGC GGAACGGACT CACCTCAGGG        1500

AACCAAGCTA GCCCAATTCG ATGACTACGT CCGGCGTTCC ATTTGGCATG        1550

ACACTACGAC CAACACGATC TCGGTTGTCT CGGCGCACTC CGTACAGTAG        1600

GGATCGTCTA CCTCCTTTTG AGACAGAAAC CCGCGCTACC ATACTGGAGG        1650

ATCATCCGCT GCTGCCCGAA TGTAACACTT TGACAATGCA CAACGTGAGT        1700

TACGTGCGAG GTCTTCCCTG CAGTGTGGGA TTTACGCTGA TTCAGGAATG        1750

GGTTGTTCCC TGGATATGG TTCTAACGCG GGAGGAGCTT GTAATCCTGA         1800

GGAAGTGTAT GCACGTGTGC CTGTGTTGTG CCAACATTGA TATCATGACG        1850
```

-continued

```
AGCATGATGA TCCATGGTTA CGAGTCCTGG GCTCTCCACT GTCATTGTTC         1900

CAGTCCCGGT TCCCTGCAGT GTATAGCCGG CGGGCAGGTT TTGGCCAGCT         1950

GGTTTAGGAT GGTGGTGGAT GGCGCCATGT TTAATCAGAG GTTTATATGG         2000

TACCGGGAGG TGGTGAATTA CAACATGCCA AAAGAGGTAA TGTTTATGTC         2050

CAGCGTGTTT ATGAGGGGTC GCCACTTAAT CTACCTGCGC TTGTGGTATG         2100

ATGGCCACGT GGGTTCTGTG GTCCCCGCCA TGAGCTTTGG ATACAGCGCC         2150

TTGCACTGTG GGATTTTGAA CAATATTGTG GTGCTGTGCT GCAGTTACTG         2200

TGCTGATTTA AGTGAGATCA GGGTGCGCTG CTGTGCCCGG AGGACAAGGC         2250

GCCTTATGCT GCGGGCGGTG CGAATCATCG CTGAGGAGAC CACTGCCATG         2300

TTGTATTCCT GCAGGACGGA GCGGCGGCGG CAGCAGTTTA TTCGCGCGCT         2350

GCTGCAGCAC CACCGCCCTA TCCTGATGCA CGATTATGAC TCTACCCCCA         2400

TGTAGGGATC CAAGCTTGCG GGCGCATCGA TGATATCAAG CTTGCATGCC         2450

TGCAGGTCGA CTCTAGAGGA TCCCGGGTGG NATCCCTGTG ACCCCTCCCC         2500

AGTGCCTCTC CTGGCCCTGG AAGTTGGCAC TCCAGTGCCC ACCAGCCTTG         2550

TCCTAATAAA ATTAAGTTGN ATCATTTTGT CTGACTAGGT GTCCTTCTAT         2600

AATATTATGG GGTGGAGGGG GGTGGTATGG AGCAANGGGN AANTTGGNAA         2650

GACAANCTGT AGGGCCTGCG GGGTCTATTG GAACAAGCT  GGAGTGCAGT         2700

GGCACAATCT TGGCTCACTG CAATCTCCGC CTCCTGGGTT CAAGCGATTC         2750

TCCTGCCTCA GACTCCCGAG TTGTTGGGAT TCCAGGCATG CATGACCAGG         2800

CTCAGATAAT TTTTGTTTTT TTGGTAGAGA CGGGGTTTCA CCATATTGGN         2850

CAGGCTGGTC TCCAACTCCT AATCTCAGGT GATCTNCCCA CCTTGGCCTC         2900

CCAAATTGCT GGGATTACAG GNGTGAACCA CTGNTCCCTT CCCTGTCCTT         2950

CTGATTTTAA AATAACTATA CCAGCAGGAG GACGTCCAGA CACAGCATAG         3000

GCTACCTGGC CATGCCCAAC CGGTGGGACA TTTGAGTTGC TTGCTTGGCA         3050

CTGTCCTCTC ATGCGTTGGG TCCACTCAGT AGATGCCTGT TGAATTGGGT         3100

ACGCGGCCAG CTTGGCTGTG GAATGTGTGT CAGTTAGGGT GTGGAAAGTC         3150

CCCAGGCTCC CCAGCAGGCA GAAGTATGCA AAGCATGCAT CTCAATTAGT         3200

CAGCAACCAG GTGTGGAAAG TCCCCAGGCT CCCCAGCAGG CAGAAGTATG         3250

CAAAGCATGC ATCTCAATTA GTCAGNAACC ATAGNCCCGC CCCTAACTCC         3300

GTCCATCCCG GCCCTAACTC NGGCCAGTTC CGACCNTNCT CCGGCNNATG         3350

GNTGAGTAAT TTGCNNGATT TATGCAGNGG GCGAGGNCGC CTCGGGCTCT         3400

GAGNTNTTCC AGAAGTAGTG AGGAGGCTTT NNTGGTGGAA TTGATCAGCT         3450

TGGGATCTGA TCAAGAGACA GGATGAGGAT CGNNNCGNAT GATTGAACAA         3500

GATGGGTTGC ACGGAGGTTC TCCGGNCGCT TGGGTGGGGA GGNTATTCGG         3550

NTATTNTTGG TGNACAACAG NNAAACGGNT GTTCTGATGC CGCCGCGTTC         3600

NCGCTTTCAG NGCAGGGGGG CCCCCCTTCT NTTGAGANNA GCNCCCCTTN         3650

TTG                                                            3653
```

(2) INFORMATION FOR SEQ ID NO:2:

(i) SEQUENCE CHARACTERISTICS:
        (A) LENGTH: 294 amino acids (B) TYPE: amino acid
        (C) STRANDEDNESS:
        (D) TOPOLOGY: Not Relevant (ii) MOLECULE TYPE: protein (xi) SEQUENCE DESCRIPTION: SEQ ID NO:2:

Met Thr Thr Ser Gly Val Pro Phe Gly Met Thr Leu Arg Pro Thr Arg
 1               5                  10                  15

Ser Arg Leu Ser Arg Arg Thr Pro Tyr Ser Arg Asp Arg Leu Pro Pro
                20                  25                  30

Phe Glu Thr Glu Thr Arg Ala Thr Ile Leu Glu Asp His Pro Leu Leu
            35                  40                  45

Pro Glu Cys Asn Thr Leu Thr Met His Asn Val Ser Tyr Val Arg Gly
        50                  55                  60

Leu Pro Cys Ser Val Gly Phe Thr Leu Ile Gln Glu Trp Val Val Pro
 65                  70                  75                  80

Trp Asp Met Val Leu Thr Arg Glu Glu Leu Val Ile Leu Arg Lys Cys
                85                  90                  95

Met His Val Cys Leu Cys Ala Asn Ile Asp Ile Met Thr Ser Met
                100                 105                 110

Met Ile Tyr Gly Tyr Glu Ser Trp Ala Leu His Cys His Cys Ser Ser
            115                 120                 125

Pro Gly Ser Leu Gln Cys Ile Ala Gly Gly Gln Val Leu Ala Ser Trp
        130                 135                 140

Phe Arg Met Val Val Asp Gly Ala Met Phe Asn Gln Arg Phe Ile Trp
145                 150                 155                 160

Tyr Arg Glu Val Val Asn Tyr Asn Met Pro Lys Glu Val Met Phe Met
                165                 170                 175

Ser Ser Val Phe Met Arg Gly Arg His Leu Ile Tyr Leu Arg Tyr Trp
            180                 185                 190

Tyr Asp Gly His Val Gly Ser Val Val Pro Ala Met Ser Phe Gly Tyr
        195                 200                 205

Ser Ala Leu His Cys Gly Ile Leu Asn Asn Ile Val Val Leu Cys Cys
        210                 215                 220

Ser Tyr Cys Ala Asp Leu Ser Glu Ile Arg Val Arg Cys Cys Ala Arg
225                 230                 235                 240

Arg Thr Arg Arg Leu Met Leu Arg Ala Val Arg Ile Ile Ala Glu Glu
                245                 250                 255

Thr Thr Ala Met Leu Tyr Ser Cys Arg Thr Glu Arg Arg Gln Gln
            260                 265                 270

Phe Ile Arg Ala Leu Leu Gln His His Arg Pro Ile Leu Met His Asp
        275                 280                 285

Tyr Asp Ser Thr Pro Met
        290

(2) INFORMATION FOR SEQ ID NO:3:

(i) SEQUENCE CHARACTERISTICS:
        (A) LENGTH: 35408 base pairs
        (B) TYPE: nucleic acid
        (C) STRANDEDNESS: Not Relevant
        (D) TOPOLOGY: Not Relevant (ii) MOLECULE TYPE: other nucleic acid (xi) SEQUENCE DESCRIPTION: SEQ ID NO:3:

CATCATCAAT AATATACCTT ATTTTGGATT GAAGCCAATA TGATAATGAG            50

-continued

| | |
|---|---|
| GGGGTGGAGT TTGTGACGTG GCGCGGGGCG TGGGAACGGG GCGGGTGACG | 100 |
| TAGTAGTGTG GCGGAAGTGT GATGTTGCAA GTGTGGCGGA ACACATGTAA | 150 |
| GCGACGGATG TGGCAAAAGT GACGTTTTTG GTGTGCGCCG GTGTACACAG | 200 |
| GAAGTGACAA TTTTCGCGCG GTTTTAGGCG GATGTTGTAG TAAATTTGGG | 250 |
| CGTAACCGAG TAAGATTTGG CCATTTTCGC GGGAAAACTG AATAAGAGGA | 300 |
| AGTGAAATCT GAATAATTTT GTGTTACTCA TAGCGCGTAA TATTTGTCTA | 350 |
| GGGAGATCAG CCTGCAGGTC GTTACATAAC TTACGGTAAA TGGCCCGCCT | 400 |
| GGCTGACCGC CCAACGACCC CCGCCCATTG ACGTCAATAA TGACGTATGT | 450 |
| TCCCATAGTA ACGCCAATAG GGACTTTCCA TTGACGTCAA TGGGTGGAGT | 500 |
| ATTTACGGTA AACTGCCCAC TTGGCAGTAC ATCAAGTGTA TCATATGCCA | 550 |
| AGTACGCCCC CTATTGACGT CAATGACGGT AAATGGCCCG CCTGGCATTA | 600 |
| TGCCCAGTAC ATGACCTTAT GGGACTTTCC TACTTGGCAG TACATCTACT | 650 |
| CGAGGCCACG TTCTGCTTCA CTCTCCCCAT CTCCCCCCCC TCCCCACCCC | 700 |
| CAATTTTGTA TTTATTTATT TTTTAATTAT TTTGTGCAGC GATGGGGCG | 750 |
| GGGGGGGGGG GGGGCGCGC GCCAGGCGGG GCGGGCGGG GCGAGGGGCG | 800 |
| GGGCGGGCG AGGCGGAGAG GTGCGGCGGC AGCCAATCAG AGCGGCGCGC | 850 |
| TCCGAAAGTT TCCTTTTATG GCGAGGCGG GGCGGCGGCG GCCCTATAAA | 900 |
| AAGCGAAGCG CGCGGCGGGC GGGAGCGGGA TCAGCCACCG CGGTGGCGGC | 950 |
| CGCAATTCCC GGGGATCGAA AGAGCCTGCT AAAGCAAAAA AGAAGTCACC | 1000 |
| ATGTCGTTTA CTTTGACCAA CAAGAACGTG ATTTTCGTTG CCGGTCTGGG | 1050 |
| AGGCATTGGT CTGGACACCA GCAAGGAGCT GCTCAAGCGC GATCCCGTCG | 1100 |
| TTTTACAACG TCGTGACTGG GAAAACCCTG GCGTTACCCA ACTTAATCGC | 1150 |
| CTTGCAGCAC ATCCCCCTTT CGCCAGCTGG CGTAATAGCG AAGAGGCCCG | 1200 |
| CACCGATCGC CCTTCCCAAC AGTTGCGCAG CCTGAATGGC GAATGGCGCT | 1250 |
| TTGCCTGGTT TCCGGCACCA GAAGCGGTGC CGGAAAGCTG GCTGGAGTGC | 1300 |
| GATCTTCCTG AGGCCGATAC TGTCGTCGTC CCCTCAAACT GGCAGATGCA | 1350 |
| CGGTTACGAT GCGCCCATCT ACACCAACGT AACCTATCCC ATTACGGTCA | 1400 |
| ATCCGCCGTT TGTTCCCACG GAGAATCCGA CGGGTTGTTA CTCGCTCACA | 1450 |
| TTTAATGTTG ATGAAAGCTG GCTACAGGAA GGCCAGACGC GAATTATTTT | 1500 |
| TGATGGCGTT AACTCGGCGT TTCATCTGTG GTGCAACGGG CGCTGGGTCG | 1550 |
| GTTACGGCCA GGACAGTCGT TTGCCGTCTG AATTTGACCT GAGCGCATTT | 1600 |
| TTACGCGCCG GAGAAAACCG CCTCGCGGTG ATGGTGCTGC GTTGGAGTGA | 1650 |
| CGGCAGTTAT CTGGAAGATC AGGATATGTG GCGGATGAGC GGCATTTTCC | 1700 |
| GTGACGTCTC GTTGCTGCAT AAACCGACTA CACAAATCAG CGATTTCCAT | 1750 |
| GTTGCCACTC GCTTTAATGA TGATTTCAGC CGCGCTGTAC TGGAGGCTGA | 1800 |
| AGTTCAGATG TGCGGCGAGT TGCGTGACTA CCTACGGGTA ACAGTTTCTT | 1850 |
| TATGGCAGGG TGAAACGCAG GTCGCCAGCG GCACCGCGCC TTTCGGCGGT | 1900 |
| GAAATTATCG ATGAGCGTGG TGGTTATGCC GATCGCGTCA CACTACGTCT | 1950 |
| GAACGTCGAA AACCCGAAAC TGTGGAGCGC CGAAATCCCG AATCTCTATC | 2000 |

| | |
|---|---|
| GTGCGGTGGT TGAACTGCAC ACCGCCGACG GCACGCTGAT TGAAGCAGAA | 2050 |
| GCCTGCGATG TCGGTTTCCG CGAGGTGCGG ATTGAAAATG GTCTGCTGCT | 2100 |
| GCTGAACGGC AAGCCGTTGC TGATTCGAGG CGTTAACCGT CACGAGCATC | 2150 |
| ATCCTCTGCA TGGTCAGGTC ATGGATGAGC AGACGATGGT GCAGGATATC | 2200 |
| CTGCTGATGA AGCAGAACAA CTTTAACGCC GTGCGCTGTT CGCATTATCC | 2250 |
| GAACCATCCG CTGTGGTACA CGCTGTGCGA CCGCTACGGC CTGTATGTGG | 2300 |
| TGGATGAAGC CAATATTGAA ACCCACGGCA TGGTGCCAAT GAATCGTCTG | 2350 |
| ACCGATGATC CGCGCTGGCT ACCGGCGATG AGCGAACGCG TAACGCGAAT | 2400 |
| GGTGCAGCGC GATCGTAATC ACCCGAGTGT GATCATCTGG TCGCTGGGGA | 2450 |
| ATGAATCAGG CCACGGCGCT AATCACGACG CGCTGTATCG CTGGATCAAA | 2500 |
| TCTGTCGATC CTTCCCGCCC GGTGCAGTAT GAAGGCGGCG GAGCCGACAC | 2550 |
| CACGGCCACC GATATTATTT GCCCGATGTA CGCGCGCGTG GATGAAGACC | 2600 |
| AGCCCTTCCC GGCTGTGCCG AAATGGTCCA TCAAAAAATG GCTTTCGCTA | 2650 |
| CCTGGAGAGA CGCGCCCGCT GATCCTTTGC GAATACGCCC ACGCGATGGG | 2700 |
| TAACAGTCTT GGCGGTTTCG CTAAATACTG GCAGGCGTTT CGTCAGTATC | 2750 |
| CCCGTTTACA GGGCGGCTTC GTCTGGGACT GGGTGGATCA GTCGCTGATT | 2800 |
| AAATATGATG AAAACGGCAA CCCGTGGTCG GCTTACGGCG GTGATTTTGG | 2850 |
| CGATACGCCG AACGATCGCC AGTTCTGTAT GAACGGTCTG GTCTTTGCCG | 2900 |
| ACCGCACGCC GCATCCAGCG CTGACGGAAG CAAAACACCA GCAGCAGTTT | 2950 |
| TTCCAGTTCC GTTTATCCGG GCAAACCATC GAAGTGACCA GCGAATACCT | 3000 |
| GTTCCGTCAT AGCGATAACG AGCTCCTGCA CTGGATGGTG GCGCTGGATG | 3050 |
| GTAAGCCGCT GGCAAGCGGT GAAGTGCCTC TGGATGTCGC TCCACAAGGT | 3100 |
| AAACAGTTGA TTGAACTGCC TGAACTACCG CAGCCGGAGA GCGCCGGGCA | 3150 |
| ACTCTGGCTC ACAGTACGCG TAGTGCAACC GAACGCGACC GCATGGTCAG | 3200 |
| AAGCCGGGCA CATCAGCGCC TGGCAGCAGT GGCGTCTGGC GGAAAACCTC | 3250 |
| AGTGTGACGC TCCCCGCCGC GTCCCACGCC ATCCCGCATC TGACCACCAG | 3300 |
| CGAAATGGAT TTTTGCATCG AGCTGGGTAA TAAGCGTTGG CAATTTAACC | 3350 |
| GCCAGTCAGG CTTTCTTTCA CAGATGTGGA TTGGCGATAA AAAACAACTG | 3400 |
| CTGACGCCGC TGCGCGATCA GTTCACCCGT GCACCGCTGG ATAACGACAT | 3450 |
| TGGCGTAAGT GAAGCGACCC GCATTGACCC TAACGCCTGG GTCGAACGCT | 3500 |
| GGAAGGCGGC GGGCCATTAC CAGGCCGAAG CAGCGTTGTT GCAGTGCACG | 3550 |
| GCAGATACAC TTGCTGATGC GGTGCTGATT ACGACCGCTC ACGCGTGGCA | 3600 |
| GCATCAGGGG AAAACCTTAT TTATCAGCCG GAAAACCTAC CGGATTGATG | 3650 |
| GTAGTGGTCA AATGGCGATT ACCGTTGATG TTGAAGTGGC GAGCGATACA | 3700 |
| CCGCATCCGG CGCGGATTGG CCTGAACTGC CAGCTGGCGC AGGTAGCAGA | 3750 |
| GCGGGTAAAC TGGCTCGGAT TAGGGCCGCA AGAAAACTAT CCCGACCGCC | 3800 |
| TTACTGCCGC CTGTTTTGAC CGCTGGGATC TGCCATTGTC AGACATGTAT | 3850 |
| ACCCCGTACG TCTTCCCGAG CGAAAACGGT CTGCGCTGCG GACGCGCGA | 3900 |
| ATTGAATTAT GGCCCACACC AGTGGCGCGG CGACTTCCAG TTCAACATCA | 3950 |
| GCCGCTACAG TCAACAGCAA CTGATGGAAA CCAGCCATCG CCATCTGCTG | 4000 |

-continued

| | |
|---|---|
| CACGCGGAAG AAGGCACATG GCTGAATATC GACGGTTTCC ATATGGGAT | 4050 |
| TGGTGGCGAC GACTCCTGGA GCCCGTCAGT ATCGGCGGAA TTACAGCTGA | 4100 |
| GCGCCGGTCG CTACCATTAC CAGTTGGTCT GGTGTCAAAA ATAATAATAA | 4150 |
| CCGGGCAGGC CATGTCTGCC CGTATTTCGC GTAAGGAAAT CCATTATGTA | 4200 |
| CTATTTAAAA AACACAAACT TTTGGATGTT CGGTTTATTC TTTTTCTTTT | 4250 |
| ACTTTTTTAT CATGGGAGCC TACTTCCCGT TTTTCCCGAT TTGGCTACAT | 4300 |
| GACATCAACC ATATCAGCAA AAGTGATACG GGTATTATTT TTGCCGCTAT | 4350 |
| TTCTCTGTTC TCGCTATTAT TCCAACCGCT GTTTGGTCTG CTTTCTGACA | 4400 |
| AACTCGGCCT CGACTCTAGG CGGCCGCGGG GATCCAGACA TGATAAGATA | 4450 |
| CATTGATGAG TTTGGACAAA CCACAACTAG AATGCAGTGA AAAAAATGCT | 4500 |
| TTATTTGTGA AATTTGTGAT GCTATTGCTT TATTTGTAAC CATTATAAGC | 4550 |
| TGCAATAAAC AAGTTAACAA CAACAATTGC ATTCATTTTA TGTTTCAGGT | 4600 |
| TCAGGGGAG GTGTGGGAGG TTTTTTCGGA TCCTCTAGAG TCGACCTGCA | 4650 |
| GGCTGATCAG TGGAAGGTGC TGAGGTACGA TGAGACCCGC ACCAGGTGCA | 4700 |
| GACCCTGCGA GTGTGGCGGT AAACATATTA GGAACCAGCC TGTGATGCTG | 4750 |
| GATGTGACCG AGGAGCTGAG GCCCGATCAC TTGGTGCTGG CCTGCACCCG | 4800 |
| CGCTGAGTTT GGCTCTAGCG ATGAAGATAC AGATTGAGGT ACTGAAATGT | 4850 |
| GTGGGCGTGG CTTAAGGGTG GGAAAGAATA TATAAGGTGG GGGTCTTATG | 4900 |
| TAGTTTTGTA TCTGTTTTGC AGCAGCCGCC GCCGCCATGA GCACCAACTC | 4950 |
| GTTTGATGGA AGCATTGTGA GCTCATATTT GACAACGCGC ATGCCCCCAT | 5000 |
| GGGCCGGGGT GCGTCAGAAT GTGATGGGCT CCAGCATTGA TGGTCGCCCC | 5050 |
| GTCCTGCCCG CAAACTCTAC TACCTTGACC TACGAGACCG TGTCTGGAAC | 5100 |
| GCCGTTGGAG ACTGCAGCCT CCGCCGCCGC TTCAGCCGCT GCAGCCACCG | 5150 |
| CCCGCGGGAT TGTGACTGAC TTTGCTTTCC TGAGCCCGCT TGCAAGCAGT | 5200 |
| GCAGCTTCCC GTTCATCCGC CCGCGATGAC AAGTTGACGG CTCTTTTGGC | 5250 |
| ACAATTGGAT TCTTTGACCC GGGAACTTAA TGTCGTTTCT CAGCAGCTGT | 5300 |
| TGGATCTGCG CCAGCAGGTT TCTGCCCTGA AGGCTTCCTC CCCTCCCAAT | 5350 |
| GCGGTTTAAA ACATAAATAA AAAACCAGAC TCTGTTTGGA TTTGGATCAA | 5400 |
| GCAAGTGTCT TGCTGTCTTT ATTTAGGGGT TTTGCGCGCG CGGTAGGCCC | 5450 |
| GGGACCAGCG GTCTCGGTCG TTGAGGGTCC TGTGTATTTT TTCCAGGACG | 5500 |
| TGGTAAAGGT GACTCTGGAT GTTCAGATAC ATGGGCATAA GCCCGTCTCT | 5550 |
| GGGGTGGAGG TAGCACCACT GCAGAGCTTC ATGCTGCGGG GTGGTGTTGT | 5600 |
| AGATGATCCA GTCGTAGCAG GAGCGCTGGG CGTGGTGCCT AAAAATGTCT | 5650 |
| TTCAGTAGCA AGCTGATTGC CAGGGCAGG CCCTTGGTGT AAGTGTTTAC | 5700 |
| AAAGCGGTTA AGCTGGGATG GGTGCATACG TGGGGATATG AGATGCATCT | 5750 |
| TGGACTGTAT TTTTAGGTTG GCTATGTTCC CAGCCATATC CCTCCGGGGA | 5800 |
| TTCATGTTGT GCAGAACCAC CAGCACAGTG TATCCGGTGC ACTTGGGAAA | 5850 |
| TTTGTCATGT AGCTTAGAAG GAAATGCGTG GAAGAACTTG GAGACGCCCT | 5900 |
| TGTGACCTCC AAGATTTTCC ATGCATTCGT CCATAATGAT GGCAATGGGC | 5950 |

| | |
|---|---|
| CCACGGGCGG CGGCCTGGGC GAAGATATTT CTGGGATCAC TAACGTCATA | 6000 |
| GTTGTGTTCC AGGATGAGAT CGTCATAGGC CATTTTTACA AAGCGCGGGC | 6050 |
| GGAGGGTGCC AGACTGCGGT ATAATGGTTC CATCCGGCCC AGGGGCGTAG | 6100 |
| TTACCCTCAC AGATTTGCAT TTCCCACGCT TTGAGTTCAG ATGGGGGAT | 6150 |
| CATGTCTACC TGCGGGCGA TGAAGAAAAC GGTTTCCGGG GTAGGGGAGA | 6200 |
| TCAGCTGGGA AGAAAGCAGG TTCCTGAGCA GCTGCGACTT ACCGCAGCCG | 6250 |
| GTGGGCCCGT AAATCACACC TATTACCGGG TGCAACTGGT AGTTAAGAGA | 6300 |
| GCTGCAGCTG CCGTCATCCC TGAGCAGGGG GGCCACTTCG TTAAGCATGT | 6350 |
| CCCTGACTCG CATGTTTTCC CTGACCAAAT CCGCCAGAAG GCGCTCGCCG | 6400 |
| CCCAGCGATA GCAGTTCTTG CAAGGAAGCA AAGTTTTTCA ACGGTTTGAG | 6450 |
| ACCGTCCGCC GTAGGCATGC TTTTGAGCGT TTGACCAAGC AGTTCCAGGC | 6500 |
| GGTCCCACAG CTCGGTCACC TGCTCTACGG CATCTCGATC CAGCATATCT | 6550 |
| CCTCGTTTCG CGGGTTGGGG CGGCTTTCGC TGTACGGCAG TAGTCGGTGC | 6600 |
| TCGTCCAGAC GGGCCAGGGT CATGTCTTTC CACGGGCGCA GGGTCCTCGT | 6650 |
| CAGCGTAGTC TGGGTCACGG TGAAGGGGTG CGCTCCGGGC TGCGCGCTGG | 6700 |
| CCAGGGTGCG CTTGAGGCTG GTCCTGCTGG TGCTGAAGCG CTGCCGGTCT | 6750 |
| TCGCCCTGCG CGTCGGCCAG GTAGCATTTG ACCATGGTGT CATAGTCCAG | 6800 |
| CCCCTCCGCG GCGTGGCCCT TGGCGCGCAG CTTGCCCTTG GAGGAGGCGC | 6850 |
| CGCACGAGGG GCAGTGCAGA CTTTTGAGGG CGTAGAGCTT GGGCGCGAGA | 6900 |
| AATACCGATT CCGGGGAGTA GGCATCCGCG CCGCAGGCCC CGCAGACGGT | 6950 |
| CTCGCATTCC ACGAGCCAGG TGAGCTCTGG CCGTTCGGGG TCAAAAACCA | 7000 |
| GGTTTCCCCC ATGCTTTTTG ATGCGTTTCT TACCTCTGGT TTCCATGAGC | 7050 |
| CGGTGTCCAC GCTCGGTGAC GAAAAGGCTG TCCGTGTCCC CGTATACAGA | 7100 |
| CTTGAGAGGC CTGTCCTCGA GCGGTGTTCC GCGGTCCTCC TCGTATAGAA | 7150 |
| ACTCGGACCA CTCTGAGACA AAGGCTCGCG TCCAGGCCAG CACGAAGGAG | 7200 |
| GCTAAGTGGG AGGGGTAGCG GTCGTTGTCC ACTAGGGGGT CCACTCGCTC | 7250 |
| CAGGGTGTGA AGACACATGT CGCCCTCTTC GGCATCAAGG AAGGTGATTG | 7300 |
| GTTTGTAGGT GTAGGCCACG TGACCGGGTG TTCCTGAAGG GGGGCTATAA | 7350 |
| AAGGGGGTGG GGGCGCGTTC GTCCTCACTC TCTTCCGCAT CGCTGTCTGC | 7400 |
| GAGGGCCAGC TGTTGGGGTG AGTACTCCCT CTGAAAAGCG GGCATGACTT | 7450 |
| CTGCGCTAAG ATTGTCAGTT TCCAAAAACG AGGAGGATTT GATATTCACC | 7500 |
| TGGCCCGCGG TGATGCCTTT GAGGGTGGCC GCATCCATCT GGTCAGAAAA | 7550 |
| GACAATCTTT TTGTTGTCAA GCTTGGTGGC AAACGACCCG TAGAGGGCGT | 7600 |
| TGGACAGCAA CTTGGCGATG GAGCGCAGGG TTTGGTTTTT GTCGCGATCG | 7650 |
| GCGCGCTCCT TGGCCGCGAT GTTTAGCTGC ACGTATTCGC GCGCAACGCA | 7700 |
| CCGCCATTCG GGAAAGACGG TGGTGCGCTC GTCGGGCACC AGGTGCACGC | 7750 |
| GCCAACCGCG GTTGTGCAGG GTGACAAGGT CAACGCTGGT GGCTACCTCT | 7800 |
| CCGCGTAGGC GCTCGTTGGT CCAGCAGAGG CGGCCGCCCT TGCGCGAGCA | 7850 |
| GAATGGCGGT AGGGGGTCTA GCTGCGTCTC GTCCGGGGGG TCTGCGTCCA | 7900 |
| CGGTAAAGAC CCCGGGCAGC AGGCGCGCGT CGAAGTAGTC TATCTTGCAT | 7950 |

```
CCTTGCAAGT CTAGCGCCTG CTGCCATGCG CGGGCGGCAA GCGCGCGCTC        8000

GTATGGGTTG AGTGGGGGAC CCCATGGCAT GGGGTGGGTG AGCGCGGAGG        8050

CGTACATGCC GCAAATGTCG TAAACGTAGA GGGGCTCTCT GAGTATTCCA        8100

AGATATGTAG GGTAGCATCT TCCACCGCGG ATGCTGGCGC GCACGTAATC        8150

GTATAGTTCG TGCGAGGGAG CGAGGAGGTC GGGACCGAGG TTGCTACGGG        8200

CGGGCTGCTC TGCTCGGAAG ACTATCTGCC TGAAGATGGC ATGTGAGTTG        8250

GATGATATGG TTGGACGCTG GAAGACGTTG AAGCTGGCGT CTGTGAGACC        8300

TACCGCGTCA CGCACGAAGG AGGCGTAGGA GTCGCGCAGC TTGTTGACCA        8350

GCTCGGCGGT GACCTGCACG TCTAGGGCGC AGTAGTCCAG GGTTTCCTTG        8400

ATGATGTCAT ACTTATCCTG TCCCTTTTTT TTCCACAGCT CGCGGTTGAG        8450

GACAAACTCT TCGCGGTCTT TCCAGTACTC TTGGATCGGA AACCCGTCGG        8500

CCTCCGAACG GTAAGAGCCT AGCATGTAGA ACTGGTTGAC GGCCTGGTAG        8550

GCGCAGCATC CCTTTTCTAC GGGTAGCGCG TATGCCTGCG CGGCCTTCCG        8600

GAGCGAGGTG TGGGTGAGCG CAAAGGTGTC CCTGACCATG ACTTTGAGGT        8650

ACTGGTATTT GAAGTCAGTG TCGTCGCATC CGCCCTGCTC CCAGAGCAAA        8700

AAGTCCGTGC GCTTTTTGGA ACGCGGATTT GGCAGGGCGA AGGTGACATC        8750

GTTGAAGAGT ATCTTTCCCG CGCGAGGCAT AAAGTTGCGT GTGATGCGGA        8800

AGGGTCCCGG CACCTCGGAA CGGTTGTTAA TTACCTGGGC GGCGAGCACG        8850

ATCTCGTCAA AGCCGTTGAT GTTGTGGCCC ACAATGTAAA GTTCCAAGAA        8900

GCGCGGGATG CCCTTGATGG AAGGCAATTT TTTAAGTTCC TCGTAGGTGA        8950

GCTCTTCAGG GGAGCTGAGC CCGTGCTCTG AAAGGGCCCA GTCTGCAAGA        9000

TGAGGGTTGG AAGCGACGAA TGAGCTCCAC AGGTCACGGG CCATTAGCAT        9050

TTGCAGGTGG TCGCGAAAGG TCCTAAACTG GCGACCTATG GCCATTTTTT        9100

CTGGGGTGAT GCAGTAGAAG GTAAGCGGGT CTTGTTCCCA GCGGTCCCAT        9150

CCAAGGTTCG CGGCTAGGTC TCGCGCGGCA GTCACTAGAG GCTCATCTCC        9200

GCCGAACTTC ATGACCAGCA TGAAGGGCAC GAGCTGCTTC CCAAAGGCCC        9250

CCATCCAAGT ATAGGTCTCT ACATCGTAGG TGACAAAGAG ACGCTCGGTG        9300

CGAGGATGCG AGCCGATCGG GAAGAACTGG ATCTCCCGCC ACCAATTGGA        9350

GGAGTGGCTA TTGATGTGGT GAAAGTAGAA GTCCCTGCGA CGGGCCGAAC        9400

ACTCGTGCTG GCTTTTGTAA AAACGTGCGC AGTACTGGCA GCGGTGCACG        9450

GGCTGTACAT CCTGCACGAG GTTGACCTGA CGACCGCGCA CAAGGAAGCA        9500

GAGTGGGAAT TTGAGCCCCT CGCCTGGCGG GTTTGGCTGG TGGTCTTCTA        9550

CTTCGGCTGC TTGTCCTTGA CCGTCTGGCT GCTCGAGGGG AGTTACGGTG        9600

GATCGGACCA CCACGCCGCG CGAGCCCAAA GTCCAGATGT CCGCGCGCGG        9650

CGGTCGGAGC TTGATGACAA CATCGCGCAG ATGGGAGCTG TCCATGGTCT        9700

GGAGCTCCCG CGGCGTCAGG TCAGGCGGGA GCTCCTGCAG GTTTACCTCG        9750

CATAGACGGG TCAGGGCGCG GGCTAGATCC AGGTGATACC TAATTTCCAG        9800

GGGCTGGTTT GTGGCGGCGT CGATGGCTTG CAAGAGGCCG CATCCCCGCG        9850

GCGCGACTAC GGTACCGCGC GGCGGGCGGT GGGCCGCGGG GGTGTCCTTG        9900
```

| | |
|---|---|
| GATGATGCAT CTAAAAGCGG TGACGCGGGC GAGCCCCCGG AGGTAGGGGG | 9950 |
| GGCTCCGGAC CCGCCGGGAG AGGGGGCAGG GGCACGTCGG CGCCGCGCGC | 10000 |
| GGGCAGGAGC TGGTGCTGCG CGCGTAGGTT GCTGGCGAAC GCGACGACGC | 10050 |
| GGCGGTTGAT CTCCTGAATC TGGCGCCTCT GCGTGAAGAC GACGGGCCCG | 10100 |
| GTGAGCTTGA GCCTGAAAGA GAGTTCGACA GAATCAATTT CGGTGTCGTT | 10150 |
| GACGGCGGCC TGGCGCAAAA TCTCCTGCAC GTCTCCTGAG TTGTCTTGAT | 10200 |
| AGGCGATCTC GGCCATGAAC TGCTCGATCT CTTCCTCCTG GAGATCTCCG | 10250 |
| CGTCCGGCTC GCTCCACGGT GGCGGCGAGG TCGTTGGAAA TGCGGGCCAT | 10300 |
| GAGCTGCGAG AAGGCGTTGA GGCCTCCCTC GTTCCAGACG CGGCTGTAGA | 10350 |
| CCACGCCCCC TTCGGCATCG CGGGCGCGCA TGACCACCTG CGCGAGATTG | 10400 |
| AGCTCCACGT GCCGGGCGAA GACGGCGTAG TTTCGCAGGC GCTGAAAGAG | 10450 |
| GTAGTTGAGG GTGGTGGCGG TGTGTTCTGC CACGAAGAAG TACATAACCC | 10500 |
| AGCGTCGCAA CGTGGATTCG TTGATATCCC CCAAGGCCTC AAGGCGCTCC | 10550 |
| ATGGCCTCGT AGAAGTCCAC GGCGAAGTTG AAAAACTGGG AGTTGCGCGC | 10600 |
| CGACACGGTT AACTCCTCCT CCAGAAGACG GATGAGCTCG GCGACAGTGT | 10650 |
| CGCGCACCTC GCGCTCAAAG GCTACAGGGG CCTCTTCTTC TTCTTCAATC | 10700 |
| TCCTCTTCCA TAAGGGCCTC CCCTTCTTCT TCTTCTGGCG GCGGTGGGGG | 10750 |
| AGGGGGACA CGGCGGCGAC GACGGCGCAC CGGGAGGCGG TCGACAAAGC | 10800 |
| GCTCGATCAT CTCCCCGCGG CGACGGCGCA TGGTCTCGGT GACGGCGCGG | 10850 |
| CCGTTCTCGC GGGGGCGCAG TTGGAAGACG CCGCCCGTCA TGTCCCGGTT | 10900 |
| ATGGGTTGGC GGGGGGCTGC CATGCGGCAG GGATACGGCG CTAACGATGC | 10950 |
| ATCTCAACAA TTGTTGTGTA GGTACTCCGC CGCCGAGGGA CCTGAGCGAG | 11000 |
| TCCGCATCGA CCGGATCGGA AAACCTCTCG AGAAAGGCGT CTAACCAGTC | 11050 |
| ACAGTCGCAA GGTAGGCTGA GCACCGTGGC GGGCGGCAGC GGGCGGCGGT | 11100 |
| CGGGGTTGTT TCTGGCGGAG GTGCTGCTGA TGATGTAATT AAAGTAGGCG | 11150 |
| GTCTTGAGAC GGCGGATGGT CGACAGAAGC ACCATGTCCT TGGGTCCGGC | 11200 |
| CTGCTGAATG CGCAGGCGGT CGGCCATGCC CCAGGCTTCG TTTTGACATC | 11250 |
| GGCGCAGGTC TTTGTAGTAG TCTTGCATGA GCCTTTCTAC CGGCACTTCT | 11300 |
| TCTTCTCCTT CCTCTTGTCC TGCATCTCTT GCATCTATCG CTGCGGCGGC | 11350 |
| GGCGGAGTTT GGCCGTAGGT GGCGCCCTCT TCCTCCCATG CGTGTGACCC | 11400 |
| CGAAGCCCCT CATCGGCTGA AGCAGGGCTA GGTCGGCGAC AACGCGCTCG | 11450 |
| GCTAATATGG CCTGCTGCAC CTGCGTGAGG GTAGACTGGA AGTCATCCAT | 11500 |
| GTCCACAAAG CGGTGGTATG CGCCCGTGTT GATGGTGTAA GTGCAGTTGG | 11550 |
| CCATAACGGA CCAGTTAACG GTCTGGTGAC CCGGCTGCGA GAGCTCGGTG | 11600 |
| TACCTGAGAC GCGAGTAAGC CCTCGAGTCA AATACGTAGT CGTTGCAAGT | 11650 |
| CCGCACCAGG TACTGGTATC CCACCAAAAA GTGCGGCGGC GGCTGGCGGT | 11700 |
| AGAGGGGCCA GCGTAGGGTG GCCGGGGCTC CGGGGGCGAG ATCTTCCAAC | 11750 |
| ATAAGGCGAT GATATCCGTA GATGTACCTG GACATCCAGG TGATGCCGGC | 11800 |
| GGCGGTGGTG GAGGCGCGCG GAAAGTCGCG GACGCGGTTC CAGATGTTGC | 11850 |
| GCAGCGGCAA AAAGTGCTCC ATGGTCGGGA CGCTCTGGCC GGTCAGGCGC | 11900 |

```
GCGCAATCGT TGACGCTCTA GACCGTGCAA AAGGAGAGCC TGTAAGCGGG       11950

CACTCTTCCG TGGTCTGGTG GATAAATTCG CAAGGGTATC ATGGCGGACG       12000

ACCGGGGTTC GAGCCCCGTA TCCGGCCGTC CGCCGTGATC CATGCGGTTA       12050

CCGCCCGCGT GTCGAACCCA GGTGTGCGAC GTCAGACAAC GGGGGAGTGC       12100

TCCTTTTGGC TTCCTTCCAG GCGCGGCGGC TGCTGCGCTA GCTTTTTTGG       12150

CCACTGGCCG CGCGCAGCGT AAGCGGTTAG GCTGGAAAGC GAAAGCATTA       12200

AGTGGCTCGC TCCCTGTAGC GGGAGGGTTA TTTTCCAAGG GTTGAGTCGC       12250

GGGACCCCCG GTTCGAGTCT CGGACCGGCC GGACTGCGGC GAACGGGGGT       12300

TTGCCTCCCC GTCATGCAAG ACCCCGCTTG CAAATTCCTC CGGAAACAGG       12350

GACGAGCCCC TTTTTTGCTT TTCCCAGATG CATCCGGTGC TGCGGCAGAT       12400

GCGCCCCCCT CCTCAGCAGC GGCAAGAGCA AGAGCAGCGG CAGACATGCA       12450

GGGCACCCTC CCCTCCTCCT ACCGCGTCAG GAGGGGCGAC ATCCGCGGTT       12500

GACGCGGCAG CAGATGGTGA TTACGAACCC CCGCGGCGCC GGGCCCGGCA       12550

CTACCTGGAC TTGGAGGAGG GCGAGGGCCT GGCGCGGCTA GGAGCGCCCT       12600

CTCCTGAGCG GTACCCAAGG GTGCAGCTGA AGCGTGATAC GCGTGAGGCG       12650

TACGTGCCGC GGCAGAACCT GTTTCGCGAC CGCGAGGGAG AGGAGCCCGA       12700

GGAGATGCGG GATCGAAAGT TCCACGCAGG GCGCGAGCTG CGGCATGGCC       12750

TGAATCGCGA GCGGTTGCTG CGCGAGGAGG ACTTTGAGCC CGACGCGCGA       12800

ACCGGGATTA GTCCCGCGCG CGCACACGTG GCGGCCGCCG ACCTGGTAAC       12850

CGCATACGAG CAGACGGTGA ACCAGGAGAT TAACTTTCAA AAAAGCTTTA       12900

ACAACCACGT GCGTACGCTT GTGGCGCGCG AGGAGGTGGC TATAGGACTG       12950

ATGCATCTGT GGGACTTTGT AAGCGCGCTG GAGCAAAACC CAAATAGCAA       13000

GCCGCTCATG GCGCAGCTGT TCCTTATAGT GCAGCACAGC AGGGACAACG       13050

AGGCATTCAG GGATGCGCTG CTAAACATAG TAGAGCCCGA GGGCCGCTGG       13100

CTGCTCGATT TGATAAACAT CCTGCAGAGC ATAGTGGTGC AGGAGCGCAG       13150

CTTGAGCCTG GCTGACAAGG TGGCCGCCAT CAACTATTCC ATGCTTAGCC       13200

TGGGCAAGTT TTACGCCCGC AAGATATACC ATACCCCTTA CGTTCCCATA       13250

GACAAGGAGG TAAAGATCGA GGGGTTCTAC ATGCGCATGG CGCTGAAGGT       13300

GCTTACCTTG AGCGACGACC TGGGCGTTTA TCGCAACGAG CGCATCCACA       13350

AGGCCGTGAG CGTGAGCCGG CGGCGCGAGC TCAGCGACCG CGAGCTGATG       13400

CACAGCCTGC AAAGGGCCCT GGCTGGCACG GGCAGCGGCG ATAGAGAGGC       13450

CGAGTCCTAC TTTGACGCGG GCGCTGACCT GCGCTGGGCC CCAAGCCGAC       13500

GCGCCCTGGA GGCAGCTGGG GCCGGACCTG GCTGGCGGT GGCACCCGCG        13550

CGCGCTGGCA ACGTCGGCGG CGTGGAGGAA TATGACGAGG ACGATGAGTA       13600

CGAGCCAGAG GACGGCGAGT ACTAAGCGGT GATGTTTCTG ATCAGATGAT       13650

GCAAGACGCA ACGGACCCGG CGGTGCGGGC GGCGCTGCAG AGCCAGCCGT       13700

CCGGCCTTAA CTCCACGGAC GACTGGCGCC AGGTCATGGA CCGCATCATG       13750

TCGCTGACTG CGCGCAATCC TGACGCGTTC CGGCAGCAGC CGCAGGCCAA       13800

CCGGCTCTCC GCAATTCTGG AAGCGGTGGT CCCGGCGCGC GCAAACCCCA       13850
```

| | |
|---|---|
| CGCACGAGAA GGTGCTGGCG ATCGTAAACG CGCTGGCCGA AAACAGGGCC | 13900 |
| ATCCGGCCCG ACGAGGCCGG CCTGGTCTAC GACGCGCTGC TTCAGCGCGT | 13950 |
| GGCTCGTTAC AACAGCGGCA ACGTGCAGAC CAACCTGGAC CGGCTGGTGG | 14000 |
| GGGATGTGCG CGAGGCCGTG GCGCAGCGTG AGCGCGCGCA GCAGCAGGGC | 14050 |
| AACCTGGGCT CCATGGTTGC ACTAAACGCC TTCCTGAGTA CACAGCCCGC | 14100 |
| CAACGTGCCG CGGGGACAGG AGGACTACAC CAACTTTGTG AGCGCACTGC | 14150 |
| GGCTAATGGT GACTGAGACA CCGCAAAGTG AGGTGTACCA GTCTGGGCCA | 14200 |
| GACTATTTTT TCCAGACCAG TAGACAAGGC CTGCAGACCG TAAACCTGAG | 14250 |
| CCAGGCTTTC AAAAACTTGC AGGGGCTGTG GGGGTGCGG GCTCCCACAG | 14300 |
| GCGACCGCGC GACCGTGTCT AGCTTGCTGA CGCCCAACTC GCGCCTGTTG | 14350 |
| CTGCTGCTAA TAGCGCCCTT CACGGACAGT GGCAGCGTGT CCCGGGACAC | 14400 |
| ATACCTAGGT CACTTGCTGA CACTGTACCG CGAGGCCATA GGTCAGGCGC | 14450 |
| ATGTGGACGA GCATACTTTC CAGGAGATTA CAAGTGTCAG CCGCGCGCTG | 14500 |
| GGGCAGGAGG ACACGGGCAG CCTGGAGGCA ACCCTAAACT ACCTGCTGAC | 14550 |
| CAACCGGCGG CAGAAGATCC CCTCGTTGCA CAGTTTAAAC AGCGAGGAGG | 14600 |
| AGCGCATTTT GCGCTACGTG CAGCAGAGCG TGAGCCTTAA CCTGATGCGC | 14650 |
| GACGGGGTAA CGCCCAGCGT GGCGCTGGAC ATGACCGCGC GCAACATGGA | 14700 |
| ACCGGGCATG TATGCCTCAA ACCGGCCGTT TATCAACCGC CTAATGGACT | 14750 |
| ACTTGCATCG CGCGGCCGCC GTGAACCCCG AGTATTTCAC CAATGCCATC | 14800 |
| TTGAACCCGC ACTGGCTACC GCCCCCTGGT TTCTACACCG GGGGATTCGA | 14850 |
| GGTGCCCGAG GGTAACGATG GATTCCTCTG GGACGACATA GACGACAGCG | 14900 |
| TGTTTTCCCC GCAACCGCAG ACCCTGCTAG AGTTGCAACA GCGCGAGCAG | 14950 |
| GCAGAGGCGG CGCTGCGAAA GGAAAGCTTC CGCAGGCCAA GCAGCTTGTC | 15000 |
| CGATCTAGGC GCTGCGGCCC CGCGGTCAGA TGCTAGTAGC CCATTTCCAA | 15050 |
| GCTTGATAGG GTCTCTTACC AGCACTCGCA CCACCCGCCC GCGCCTGCTG | 15100 |
| GGCGAGGAGG AGTACCTAAA CAACTCGCTG CTGCAGCCGC AGCGCGAAAA | 15150 |
| AAACCTGCCT CCGGCATTTC CAACAACGG GATAGAGAGC CTAGTGGACA | 15200 |
| AGATGAGTAG ATGGAAGACG TACGCGCAGG AGCACAGGGA CGTGCCAGGC | 15250 |
| CCGCGCCCGC CCACCCGTCG TCAAAGGCAC GACCGTCAGC GGGGTCTGGT | 15300 |
| GTGGGAGGAC GATGACTCGG CAGACGACAG CAGCGTCCTG GATTTGGGAG | 15350 |
| GGAGTGGCAA CCCGTTTGCG CACCTTCGCC CCAGGCTGGG GAGAATGTTT | 15400 |
| TAAAAAAAAA AAAGCATGAT GCAAAATAAA AAACTCACCA AGGCCATGGC | 15450 |
| ACCGAGCGTT GGTTTTCTTG TATTCCCCTT AGTATGCGGC GCGCGGCGAT | 15500 |
| GTATGAGGAA GGTCCTCCTC CCTCCTACGA GAGTGTGGTG AGCGCGGCGC | 15550 |
| CAGTGGCGGC GGCGCTGGGT TCTCCCTTCG ATGCTCCCCT GGACCCGCCG | 15600 |
| TTTGTGCCTC CGCGGTACCT GCGGCCTACC GGGGGGAGAA ACAGCATCCG | 15650 |
| TTACTCTGAG TTGGCACCCC TATTCGACAC CACCCGTGTG TACCTGGTGG | 15700 |
| ACAACAAGTC AACGGATGTG GCATCCCTGA ACTACCAGAA CGACCACAGC | 15750 |
| AACTTTCTGA CCACGGTCAT TCAAAACAAT GACTACAGCC CGGGGGAGGC | 15800 |
| AAGCACACAG ACCATCAATC TTGACGACCG GTCGCACTGG GGCGGCGACC | 15850 |

-continued

| | |
|---|---|
| TGAAAACCAT CCTGCATACC AACATGCCAA ATGTGAACGA GTTCATGTTT | 15900 |
| ACCAATAAGT TTAAGGCGCG GGTGATGGTG TCGCGCTTGC CTACTAAGGA | 15950 |
| CAATCAGGTG GAGCTGAAAT ACGAGTGGGT GGAGTTCACG CTGCCCGAGG | 16000 |
| GCAACTACTC CGAGACCATG ACCATAGACC TTATGAACAA CGCGATCGTG | 16050 |
| GAGCACTACT TGAAAGTGGG CAGACAGAAC GGGGTTCTGG AAAGCGACAT | 16100 |
| CGGGGTAAAG TTTGACACCC GCAACTTCAG ACTGGGGTTT GACCCCGTCA | 16150 |
| CTGGTCTTGT CATGCCTGGG GTATATACAA ACGAAGCCTT CCATCCAGAC | 16200 |
| ATCATTTTGC TGCCAGGATG CGGGGTGGAC TTCACCCACA GCCGCCTGAG | 16250 |
| CAACTTGTTG GGCATCCGCA AGCGGCAACC CTTCCAGGAG GGCTTTAGGA | 16300 |
| TCACCTACGA TGATCTGGAG GGTGGTAACA TTCCCGCACT GTTGGATGTG | 16350 |
| GACGCCTACC AGGCGAGCTT GAAAGATGAC ACCGAACAGG GCGGGGGTGG | 16400 |
| CGCAGGCGGC AGCAACAGCA GTGGCAGCGG CGCGGAAGAG AACTCCAACG | 16450 |
| CGGCAGCCGC GGCAATGCAG CCGGTGGAGG ACATGAACGA TCATGCCATT | 16500 |
| CGCGGCGACA CCTTTGCCAC ACGGGCTGAG GAGAAGCGCG CTGAGGCCGA | 16550 |
| AGCAGCGGCC GAAGCTGCCG CCCCCGCTGC GCAACCCGAG GTCGAGAAGC | 16600 |
| CTCAGAAGAA ACCGGTGATC AAACCCCTGA CAGAGGACAG CAAGAAACGC | 16650 |
| AGTTACAACC TAATAAGCAA TGACAGCACC TTCACCCAGT ACCGCAGCTG | 16700 |
| GTACCTTGCA TACAACTACG GCGACCCTCA GACCGGAATC CGCTCATGGA | 16750 |
| CCCTGCTTTG CACTCCTGAC GTAACCTGCG GCTCGGAGCA GGTCTACTGG | 16800 |
| TCGTTGCCAG ACATGATGCA AGACCCCGTG ACCTTCCGCT CCACGCGCCA | 16850 |
| GATCAGCAAC TTTCCGGTGG TGGGCGCCGA GCTGTTGCCC GTGCACTCCA | 16900 |
| AGAGCTTCTA CAACGACCAG GCCGTCTACT CCCAACTCAT CCGCCAGTTT | 16950 |
| ACCTCTCTGA CCCACGTGTT CAATCGCTTT CCCGAGAACC AGATTTTGGC | 17000 |
| GCGCCCGCCA GCCCCCACCA TCACCACCGT CAGTGAAAAC GTTCCTGCTC | 17050 |
| TCACAGATCA CGGGACGCTA CCGCTGCGCA ACAGCATCGG AGGAGTCCAG | 17100 |
| CGAGTGACCA TTACTGACGC CAGACGCCGC ACCTGCCCCT ACGTTTACAA | 17150 |
| GGCCCTGGGC ATAGTCTCGC CGCGCGTCCT ATCGAGCCGC ACTTTTTGAG | 17200 |
| CAAGCATGTC CATCCTTATA TCGCCCAGCA ATAACACAGG CTGGGGCCTG | 17250 |
| CGCTTCCCAA GCAAGATGTT TGGCGGGGCC AAGAAGCGCT CCGACCAACA | 17300 |
| CCCAGTGCGC GTGCGCGGGC ACTACCGCGC GCCCTGGGGC GCGCACAAAC | 17350 |
| GCGGCCGCAC TGGGCGCACC ACCGTCGATG ACGCCATCGA CGCGGTGGTG | 17400 |
| GAGGAGGCGC GCAACTACAC GCCCACGCCG CCACCAGTGT CCACAGTGGA | 17450 |
| CGCGGCCATT CAGACCGTGG TGCGCGGAGC CCGGCGCTAT GCTAAAATGA | 17500 |
| AGAGACGGCG GAGGCGCGTA GCACGTCGCC ACCGCCGCCG ACCCGGCACT | 17550 |
| GCCGCCCAAC GCGCGGCGGC GGCCCTGCTT AACCGCGCAC GTCGCACCGG | 17600 |
| CCGACGGGCG GCCATGCGGG CCGCTCGAAG GCTGGCCGCG GGTATTGTCA | 17650 |
| CTGTGCCCCC CAGGTCCAGG CGACGAGCGG CCGCCGCAGC AGCCGCGGCC | 17700 |
| ATTAGTGCTA TGACTCAGGG TCGCAGGGGC AACGTGTATT GGGTGCGCGA | 17750 |
| CTCGGTTAGC GGCCTGCGCG TGCCCGTGCG CACCCGCCCC CCGCGCAACT | 17800 |

| | |
|---|---|
| AGATTGCAAG AAAAAACTAC TTAGACTCGT ACTGTTGTAT GTATCCAGCG | 17850 |
| GCGGCGGCGC GCAACGAAGC TATGTCCAAG CGCAAAATCA AAGAAGAGAT | 17900 |
| GCTCCAGGTC ATCGCGCCGG AGATCTATGG CCCCCCGAAG AAGGAAGAGC | 17950 |
| AGGATTACAA GCCCCGAAAG CTAAAGCGGG TCAAAAAGAA AAAGAAAGAT | 18000 |
| GATGATGATG AACTTGACGA CGAGGTGGAA CTGCTGCACG CTACCGCGCC | 18050 |
| CAGGCGACGG GTACAGTGGA AAGGTCGACG CGTAAAACGT GTTTTGCGAC | 18100 |
| CCGGCACCAC CGTAGTCTTT ACGCCCGGTG AGCGCTCCAC CCGCACCTAC | 18150 |
| AAGCGCGTGT ATGATGAGGT GTACGGCGAC GAGGACCTGC TTGAGCAGGC | 18200 |
| CAACGAGCGC CTCGGGGAGT TTGCCTACGG AAAGCGGCAT AAGGACATGC | 18250 |
| TGGCGTTGCC GCTGGACGAG GGCAACCCAA CACCTAGCCT AAAGCCCGTA | 18300 |
| ACACTGCAGC AGGTGCTGCC CGCGCTTGCA CCGTCCGAAG AAAAGCGCGG | 18350 |
| CCTAAAGCGC GAGTCTGGTG ACTTGGCACC CACCGTGCAG CTGATGGTAC | 18400 |
| CCAAGCGCCA GCGACTGGAA GATGTCTTGG AAAAAATGAC CGTGGAACCT | 18450 |
| GGGCTGGAGC CCGAGGTCCG CGTGCGGCCA ATCAAGCAGG TGGCGCCGGG | 18500 |
| ACTGGGCGTG CAGACCGTGG ACGTTCAGAT ACCCACTACC AGTAGCACCA | 18550 |
| GTATTGCCAC CGCCACAGAG GGCATGGAGA CACAAACGTC CCCGGTTGCC | 18600 |
| TCAGCGGTGG CGGATGCCGC GGTGCAGGCG GTCGCTGCGG CCGCGTCCAA | 18650 |
| GACCTCTACG GAGGTGCAAA CGGACCCGTG GATGTTTCGC GTTTCAGCCC | 18700 |
| CCCGGCGCCC GCGCGGTTCG AGGAAGTACG GCGCCGCCAG CGCGCTACTG | 18750 |
| CCCGAATATG CCCTACATCC TTCCATTGCG CCTACCCCCG GCTATCGTGG | 18800 |
| CTACACCTAC CGCCCCAGAA GACGAGCAAC TACCCGACGC CGAACCACCA | 18850 |
| CTGGAACCCG CCGCCGCCGT CGCCGTCGCC AGCCCGTGCT GGCCCCGATT | 18900 |
| TCCGTGCGCA GGGTGGCTCG CGAAGGAGGC AGGACCCTGG TGCTGCCAAC | 18950 |
| AGCGCGCTAC CACCCCAGCA TCGTTTAAAA GCCGGTCTTT GTGGTTCTTG | 19000 |
| CAGATATGGC CCTCACCTGC CGCCTCCGTT TCCCGGTGCC GGGATTCCGA | 19050 |
| GGAAGAATGC ACCGTAGGAG GGGCATGGCC GGCCACGGCC TGACGGGCGG | 19100 |
| CATGCGTCGT GCGCACCACC GGCGGCGGCG CGCGTCGCAC CGTCGCATGC | 19150 |
| GCGGCGGTAT CCTGCCCCTC CTTATTCCAC TGATCGCCGC GGCGATTGGC | 19200 |
| GCCGTGCCCG GAATTGCATC CGTGGCCTTG CAGGCGCAGA GACACTGATT | 19250 |
| AAAAACAAGT TGCATGTGGA AAAATCAAAA TAAAAAGTCT GGACTCTCAC | 19300 |
| GCTCGCTTGG TCCTGTAACT ATTTTGTAGA ATGGAAGACA TCAACTTTGC | 19350 |
| GTCTCTGGCC CCGCGACACG GCTCGCGCCC GTTCATGGGA AACTGGCAAG | 19400 |
| ATATCGGCAC CAGCAATATG AGCGGTGGCG CCTTCAGCTG GGGCTCGCTG | 19450 |
| TGGAGCGGCA TTAAAAATTT CGGTTCCACC GTTAAGAACT ATGGCAGCAA | 19500 |
| GGCCTGGAAC AGCAGCACAG GCCAGATGCT GAGGGATAAG TTGAAAGAGC | 19550 |
| AAAATTTCCA ACAAAAGGTG GTAGATGGCC TGGCCTCTGG CATTAGCGGG | 19600 |
| GTGGTGGACC TGGCCAACCA GGCAGTGCAA AATAAGATTA ACAGTAAGCT | 19650 |
| TGATCCCCGC CCTCCCGTAG AGGAGCCTCC ACCGGCCGTG GAGACAGTGT | 19700 |
| CTCCAGAGGG GCGTGGCGAA AAGCGTCCGC GCCCCGACAG GGAAGAAACT | 19750 |
| CTGGTGACGC AAATAGACGA GCCTCCCTCG TACGAGGAGG CACTAAAGCA | 19800 |

| | |
|---|---|
| AGGCCTGCCC ACCACCCGTC CCATCGCGCC CATGGCTACC GGAGTGCTGG | 19850 |
| GCCAGCACAC ACCCGTAACG CTGGACCTGC CTCCCCCCGC CGACACCCAG | 19900 |
| CAGAAACCTG TGCTGCCAGG CCCGACCGCC GTTGTTGTAA CCCGTCCTAG | 19950 |
| CCGCGCGTCC CTGCGCCGCG CCGCCAGCGG TCCGCGATCG TTGCGGCCCG | 20000 |
| TAGCCAGTGG CAACTGGCAA AGCACACTGA ACAGCATCGT GGGTCTGGGG | 20050 |
| GTGCAATCCC TGAAGCGCCG ACGATGCTTC TGAATAGCTA ACGTGTCGTA | 20100 |
| TGTGTGTCAT GTATGCGTCC ATGTCGCCGC CAGAGGAGCT GCTGAGCCGC | 20150 |
| CGCGCGCCCG CTTTCCAAGA TGGCTACCCC TTCGATGATG CCGCAGTGGT | 20200 |
| CTTACATGCA CATCTCGGGC CAGGACGCCT CGGAGTACCT GAGCCCCGGG | 20250 |
| CTGGTGCAGT TTGCCCGCGC CACCGAGACG TACTTCAGCC TGAATAACAA | 20300 |
| GTTTAGAAAC CCCACGGTGG CGCCTACGCA CGACGTGACC ACAGACCGGT | 20350 |
| CCCAGCGTTT GACGCTGCGG TTCATCCCTG TGGACCGTGA GGATACTGCG | 20400 |
| TACTCGTACA AGGCGCGGTT CACCCTAGCT GTGGGTGATA ACCGTGTGCT | 20450 |
| GGACATGGCT TCCACGTACT TTGACATCCG CGGCGTGCTG GACAGGGGCC | 20500 |
| CTACTTTTAA GCCCTACTCT GGCACTGCCT ACAACGCCCT GGCTCCCAAG | 20550 |
| GGTGCCCCAA ATCCTTGCGA ATGGGATGAA GCTGCTACTG CTCTTGAAAT | 20600 |
| AAACCTAGAA GAAGAGGACG ATGACAACGA AGACAGAAGTA GACGAGCAAG | 20650 |
| CTGAGCAGCA AAAAACTCAC GTATTTGGGC AGGCGCCTTA TTCTGGTATA | 20700 |
| AATATTACAA AGGAGGGTAT TCAAATAGGT GTCGAAGGTC AAACACCTAA | 20750 |
| ATATGCCGAT AAAACATTTC AACCTGAACC TCAAATAGGA GAATCTCAGT | 20800 |
| GGTACGAAAC TGAAATTAAT CATGCAGCTG GGAGAGTCCT TAAAAAGACT | 20850 |
| ACCCCAATGA AACCATGTTA CGGTTCATAT GCAAAACCCA CAAATGAAAA | 20900 |
| TGGAGGGCAA GGCATTCTTG TAAAGCAACA AAATGGAAAG CTAGAAAGTC | 20950 |
| AAGTGGAAAT GCAATTTTTC TCAACTACTG AGGCGACCGC AGGCAATGGT | 21000 |
| GATAACTTGA CTCCTAAAGT GGTATTGTAC AGTGAAGATG TAGATATAGA | 21050 |
| AACCCCAGAC ACTCATATTT CTTACATGCC CACTATTAAG GAAGGTAACT | 21100 |
| CACGAGAACT AATGGGCCAA CAATCTATGC CCAACAGGCC TAATTACATT | 21150 |
| GCTTTTAGGG ACAATTTTAT TGGTCTAATG TATTACAACA GCACGGGTAA | 21200 |
| TATGGGTGTT CTGGCGGGCC AAGCATCGCA GTTGAATGCT GTTGTAGATT | 21250 |
| TGCAAGACAG AAACACAGAG CTTTCATACC AGCTTTTGCT TGATTCCATT | 21300 |
| GGTGATAGAA CCAGGTACTT TTCTATGTGG AATCAGGCTG TTGACAGCTA | 21350 |
| TGATCCAGAT GTTAGAATTA TTGAAAATCA TGGAACTGAA GATGAACTTC | 21400 |
| CAAATTACTG CTTTCCACTG GGAGGTGTGA TTAATACAGA GACTCTTACC | 21450 |
| AAGGTAAAAC CTAAAACAGG TCAGGAAAAT GGATGGGAAA AGATGCTAC | 21500 |
| AGAATTTTCA GATAAAAATG AAATAAGAGT TGGAAATAAT TTTGCCATGG | 21550 |
| AAATCAATCT AAATGCCAAC CTGTGGAGAA ATTTCCTGTA CTCCAACATA | 21600 |
| GCGCTGTATT TGCCCGACAA GCTAAAGTAC AGTCCTTCCA ACGTAAAAAT | 21650 |
| TTCTGATAAC CCAAACACCT ACGACTACAT GAACAAGCGA GTGGTGGCTC | 21700 |
| CCGGGTTAGT GGACTGCTAC ATTAACCTTG GAGCACGCTG GTCCCTTGAC | 21750 |

| | |
|---|---|
| TATATGGACA ACGTCAACCC ATTTAACCAC CACCGCAATG CTGGCCTGCG | 21800 |
| CTACCGCTCA ATGTTGCTGG GCAATGGTCG CTATGTGCCC TTCCACATCC | 21850 |
| AGGTGCCTCA GAAGTTCTTT GCCATTAAAA ACCTCCTTCT CCTGCCGGGC | 21900 |
| TCATACACCT ACGAGTGGAA CTTCAGGAAG GATGTTAACA TGGTTCTGCA | 21950 |
| GAGCTCCCTA GGAAATGACC TAAGGGTTGA CGGAGCCAGC ATTAAGTTTG | 22000 |
| ATAGCATTTG CCTTTACGCC ACCTTCTTCC CCATGGCCCA CAACACCGCC | 22050 |
| TCCACGCTTG AGGCCATGCT TAGAAACGAC ACCAACGACC AGTCCTTTAA | 22100 |
| CGACTATCTC TCCGCCGCCA ACATGCTCTA CCCTATACCC GCCAACGCTA | 22150 |
| CCAACGTGCC CATATCCATC CCCTCCCGCA ACTGGGCGG TTTCCGCGGC | 22200 |
| TGGGCCTTCA CGCGCCTTAA GACTAAGGAA ACCCCATCAC TGGGCTCGGG | 22250 |
| CTACGACCCT TATTACACCT ACTCTGGCTC TATACCCTAC CTAGATGGAA | 22300 |
| CCTTTTACCT CAACCACACC TTTAAGAAGG TGGCCATTAC CTTTGACTCT | 22350 |
| TCTGTCAGCT GGCCTGGCAA TGACCGCCTG CTTACCCCCA ACGAGTTTGA | 22400 |
| AATTAAGCGC TCAGTTGACG GGGAGGGTTA CAACGTTGCC CAGTGTAACA | 22450 |
| TGACCAAAGA CTGGTTCCTG GTACAAATGC TAGCTAACTA CAACATTGGC | 22500 |
| TACCAGGGCT TCTATATCCC AGAGAGCTAC AAGGACCGCA TGTACTCCTT | 22550 |
| CTTTAGAAAC TTCCAGCCCA TGAGCCGTCA GGTGGTGGAT GATACTAAAT | 22600 |
| ACAAGGACTA CCAACAGGTG GGCATCCTAC ACCAACACAA CAACTCTGGA | 22650 |
| TTTGTTGGCT ACCTTGCCCC CACCATGCGC GAAGGACAGG CCTACCCTGC | 22700 |
| TAACTTCCCC TATCCGCTTA TAGGCAAGAC CGCAGTTGAC AGCATTACCC | 22750 |
| AGAAAAAGTT TCTTTGCGAT CGCACCCTTT GGCGCATCCC ATTCTCCAGT | 22800 |
| AACTTTATGT CCATGGGCGC ACTCACAGAC CTGGGCCAAA ACCTTCTCTA | 22850 |
| CGCCAACTCC GCCCACGCGC TAGACATGAC TTTTGAGGTG GATCCCATGG | 22900 |
| ACGAGCCCAC CCTTCTTTAT GTTTTGTTTG AAGTCTTTGA CGTGGTCCGT | 22950 |
| GTGCACCGGC CGCACCGCGG CGTCATCGAA ACCGTGTACC TGCGCACGCC | 23000 |
| CTTCTCGGCC GGCAACGCCA CAACATAAAG AAGCAAGCAA CATCAACAAC | 23050 |
| AGCTGCCGCC ATGGGCTCCA GTGAGCAGGA ACTGAAAGCC ATTGTCAAAG | 23100 |
| ATCTTGGTTG TGGGCCATAT TTTTTGGGCA CCTATGACAA GCGCTTTCCA | 23150 |
| GGCTTTGTTT CTCCACACAA GCTCGCCTGC GCCATAGTCA ATACGGCCGG | 23200 |
| TCGCGAGACT GGGGGCGTAC ACTGGATGGC CTTTGCCTGG AACCCGCACT | 23250 |
| CAAAAACATG CTACCTCTTT GAGCCCTTTG GCTTTTCTGA CCAGCGACTC | 23300 |
| AAGCAGGTTT ACCAGTTTGA GTACGAGTCA CTCCTGCGCC GTAGCGCCAT | 23350 |
| TGCTTCTTCC CCCGACCGCT GTATAACGCT GGAAAAGTCC ACCCAAAGCG | 23400 |
| TACAGGGGCC CAACTCGGCC GCCTGTGGAC TATTCTGCTG CATGTTTCTC | 23450 |
| CACGCCTTTG CCAACTGGCC CCAAACTCCC ATGGATCACA ACCCCACCAT | 23500 |
| GAACCTTATT ACCGGGGTAC CCAACTCCAT GCTCAACAGT CCCCAGGTAC | 23550 |
| AGCCCACCCT GCGTCGCAAC CAGGAACAGC TCTACAGCTT CCTGGAGCGC | 23600 |
| CACTCGCCCT ACTTCCGCAG CCACAGTGCG CAGATTAGGA GCGCCACTTC | 23650 |
| TTTTTGTCAC TTGAAAAACA TGTAAAAATA ATGTACTAGA GACACTTTCA | 23700 |
| ATAAAGGCAA ATGCTTTTAT TTGTACACTC TCGGGTGATT ATTTACCCCC | 23750 |

-continued

| | |
|---|---|
| ACCCTTGCCG TCTGCGCCGT TTAAAAATCA AAGGGGTTCT GCCGCGCATC | 23800 |
| GCTATGCGCC ACTGGCAGGG ACACGTTGCG ATACTGGTGT TTAGTGCTCC | 23850 |
| ACTTAAACTC AGGCACAACC ATCCGCGGCA GCTCGGTGAA GTTTTCACTC | 23900 |
| CACAGGCTGC GCACCATCAC CAACGCGTTT AGCAGGTCGG GCGCCGATAT | 23950 |
| CTTGAAGTCG CAGTTGGGGC CTCCGCCCTG CGCGCGCGAG TTGCGATACA | 24000 |
| CAGGGTTGCA GCACTGGAAC ACTATCAGCG CCGGGTGGTG CACGCTGGCC | 24050 |
| AGCACGCTCT TGTCGGAGAT CAGATCCGCG TCCAGGTCCT CCGCGTTGCT | 24100 |
| CAGGGCGAAC GGAGTCAACT TTGGTAGCTG CCTTCCCAAA AAGGGCGCGT | 24150 |
| GCCCAGGCTT TGAGTTGCAC TCGCACCGTA GTGGCATCAA AAGGTGACCG | 24200 |
| TGCCCGGTCT GGGCGTTAGG ATACAGCGCC TGCATAAAAG CCTTGATCTG | 24250 |
| CTTAAAAGCC ACCTGAGCCT TTGCGCCTTC AGAGAAGAAC ATGCCGCAAG | 24300 |
| ACTTGCCGGA AAACTGATTG GCCGGACAGG CCGCGTCGTG CACGCAGCAC | 24350 |
| CTTGCGTCGG TGTTGGAGAT CTGCACCACA TTTCGGCCCC ACCGGTTCTT | 24400 |
| CACGATCTTG GCCTTGCTAG ACTGCTCCTT CAGCGCGCGC TGCCCGTTTT | 24450 |
| CGCTCGTCAC ATCCATTTCA ATCACGTGCT CCTTATTTAT CATAATGCTT | 24500 |
| CCGTGTAGAC ACTTAAGCTC GCCTTCGATC TCAGCGCAGC GGTGCAGCCA | 24550 |
| CAACGCGCAG CCCGTGGGCT CGTGATGCTT GTAGGTCACC TCTGCAAACG | 24600 |
| ACTGCAGGTA CGCCTGCAGG AATCGCCCCA TCATCGTCAC AAAGGTCTTG | 24650 |
| TTGCTGGTGA AGGTCAGCTG CAACCCGCGG TGCTCCTCGT TCAGCCAGGT | 24700 |
| CTTGCATACG GCCGCCAGAG CTTCCACTTG GTCAGGCAGT AGTTTGAAGT | 24750 |
| TCGCCTTTAG ATCGTTATCC ACGTGGTACT TGTCCATCAG CGCGCGCGCA | 24800 |
| GCCTCCATGC CCTTCTCCCA CGCAGACACG ATCGGCACAC TCAGCGGGTT | 24850 |
| CATCACCGTA ATTTCACTTT CCGCTTCGCT GGGCTCTTCC TCTTCCTCTT | 24900 |
| GCGTCCGCAT ACCACGCGCC ACTGGGTCGT CTTCATTCAG CCGCCGCACT | 24950 |
| GTGCGCTTAC CTCCTTTGCC ATGCTTGATT AGCACCGGTG GGTTGCTGAA | 25000 |
| ACCCACCATT TGTAGCGCCA CATCTTCTCT TTCTTCCTCG CTGTCCACGA | 25050 |
| TTACCTCTGG TGATGGCGGG CGCTCGGGCT TGGGAGAAGG GCGCTTCTTT | 25100 |
| TTCTTCTTGG GCGCAATGGC CAAATCCGCC GCCGAGGTCG ATGGCCGCGG | 25150 |
| GCTGGGTGTG CGCGGCACCA GCGCGTCTTG TGATGAGTCT TCCTCGTCCT | 25200 |
| CGGACTCGAT ACGCCGCCTC ATCCGCTTTT TTGGGGCGCG CCGGGGAGGC | 25250 |
| GGCGGCGACG GGGACGGGGA CGACACGTCC TCCATGGTTG GGGGACGTCG | 25300 |
| CGCCGCACCG CGTCCGCGCT CGGGGGTGGT TTCGCGCTGC TCCTCTTCCC | 25350 |
| GACTGGCCAT TTCCTTCTCC TATAGGCAGA AAAAGATCAT GGAGTCAGTC | 25400 |
| GAGAAGAAGG ACAGCCTAAC CGCCCCCTCT GAGTTCGCCA CCACCGCCTC | 25450 |
| CACCGATGCC GCCAACGCGC CTACCACCTT CCCCGTCGAG GCACCCCCGC | 25500 |
| TTGAGGAGGA GGAAGTGATT ATCGAGCAGG ACCCAGGTTT TGTAAGCGAA | 25550 |
| GACGACGAGG ACCGCTCAGT ACCAACAGAG GATAAAAAGC AAGACCAGGA | 25600 |
| CAACGCGAGG GCAAACGAGG AACAAGTCGG GCGGGGGGAC GAAAGGCATG | 25650 |
| GCGACTACCT AGATGTGGGA GACGACGTGC TGTTGAAGCA TCTGCAGCGC | 25700 |

| | |
|---|---|
| CAGTGCGCCA TTATCTGCGA CGCGTTGCAA GAGCGCAGCG ATGTGCCCCT | 25750 |
| CGCCATAGCG GATGTCAGCC TTGCCTACGA ACGCCACCTA TTCTCACCGC | 25800 |
| GCGTACCCCC CAAACGCCAA GAAAACGGCA CATGCGAGCC CAACCCGCGC | 25850 |
| CTCAACTTCT ACCCCGTATT TGCCGTGCCA GAGGTGCTTG CCACCTATCA | 25900 |
| CATCTTTTTC CAAAACTGCA AGATACCCCT ATCCTGCCGT GCCAACCGCA | 25950 |
| GCCGAGCGGA CAAGCAGCTG GCCTTGCGGC AGGGCGCTGT CATACCTGAT | 26000 |
| ATCGCCTCGC TCAACGAAGT GCCAAAAATC TTTGAGGGTC TTGGACGCGA | 26050 |
| CGAGAAGCGC GCGGCAAACG CTCTGCAACA GGAAAACAGC GAAAATGAAA | 26100 |
| GTCACTCTGG AGTGTTGGTG GAACTCGAGG GTGACAACGC GCGCCTAGCC | 26150 |
| GTACTAAAAC GCAGCATCGA GGTCACCCAC TTTGCCTACC CGGCACTTAA | 26200 |
| CCTACCCCCC AAGGTCATGA GCACAGTCAT GAGTGAGCTG ATCGTGCGCC | 26250 |
| GTGCGCAGCC CCTGGAGAGG GATGCAAATT TGCAAGAACA AACAGAGGAG | 26300 |
| GGCCTACCCG CAGTTGGCGA CGAGCAGCTA GCGCGCTGGC TTCAAACGCG | 26350 |
| CGAGCCTGCC GACTTGGAGG AGCGACGCAA ACTAATGATG GCCGCAGTGC | 26400 |
| TCGTTACCGT GGAGCTTGAG TGCATGCAGC GGTTCTTTGC TGACCCGGAG | 26450 |
| ATGCAGCGCA AGCTAGAGGA AACATTGCAC TACACCTTTC GACAGGGCTA | 26500 |
| CGTACGCCAG GCCTGCAAGA TCTCCAACGT GGAGCTCTGC AACCTGGTCT | 26550 |
| CCTACCTTGG AATTTTGCAC GAAAACCGCC TTGGGCAAAA CGTGCTTCAT | 26600 |
| TCCACGCTCA AGGGCGAGGC GCGCCGCGAC TACGTCCGCG ACTGCGTTTA | 26650 |
| CTTATTTCTA TGCTACACCT GGCAGACGGC CATGGGCGTT TGGCAGCAGT | 26700 |
| GCTTGGAGGA GTGCAACCTC AAGGAGCTGC AGAAACTGCT AAAGCAAAAC | 26750 |
| TTGAAGGACC TATGGACGGC CTTCAACGAG CGCTCCGTGG CCGCGCACCT | 26800 |
| GGCGGACATC ATTTTCCCCG AACGCCTGCT TAAAACCCTG CAACAGGGTC | 26850 |
| TGCCAGACTT CACCAGTCAA AGCATGTTGC AGAACTTTAG GAACTTTATC | 26900 |
| CTAGAGCGCT CAGGAATCTT GCCCGCCACC TGCTGTGCAC TTCCTAGCGA | 26950 |
| CTTTGTGCCC ATTAAGTACC GCGAATGCCC TCCGCCGCTT TGGGGCCACT | 27000 |
| GCTACCTTCT GCAGCTAGCC AACTACCTTG CCTACCACTC TGACATAATG | 27050 |
| GAAGACGTGA GCGGTGACGG TCTACTGGAG TGTCACTGTC GCTGCAACCT | 27100 |
| ATGCACCCCG CACCGCTCCC TGGTTTGCAA TTCGCAGCTG CTTAACGAAA | 27150 |
| GTCAAATTAT CGGTACCTTT GAGCTGCAGG GTCCCTCGCC TGACGAAAAG | 27200 |
| TCCGCGGCTC CGGGGTTGAA ACTCACTCCG GGGCTGTGGA CGTCGGCTTA | 27250 |
| CCTTCGCAAA TTTGTACCTG AGGACTACCA CGCCCACGAG ATTAGGTTCT | 27300 |
| ACGAAGACCA ATCCCGCCCG CCAAATGCGG AGCTTACCGC CTGCGTCATT | 27350 |
| ACCCAGGGCC ACATTCTTGG CCAATTGCAA GCCATCAACA AAGCCCGCCA | 27400 |
| AGAGTTTCTG CTACGAAAGG GACGGGGGGT TTACTTGGAC CCCCAGTCCG | 27450 |
| GCGAGGAGCT CAACCCAATC CCCCCGCCGC CGCAGCCCTA TCAGCAGCAG | 27500 |
| CCGCGGGCCC TTGCTTCCCA GGATGGCACC CAAAAAGAAG CTGCAGCTGC | 27550 |
| CGCCGCCACC CACGGACGAG GAGGAATACT GGGACAGTCA GGCAGAGGAG | 27600 |
| GTTTTGGACG AGGAGGAGGA GGACATGATG GAAGACTGGG AGAGCCTAGA | 27650 |
| CGAGGAAGCT TCCGAGGTCG AAGAGGTGTC AGACGAAACA CCGTCACCCT | 27700 |

-continued

| | |
|---|---|
| CGGTCGCATT CCCCTCGCCG GCGCCCCAGA AATCGGCAAC CGGTTCCAGC | 27750 |
| ATGGCTACAA CCTCCGCTCC TCAGGCGCCG CCGGCACTGC CCGTTCGCCG | 27800 |
| ACCCAACCGT AGATGGGACA CCACTGGAAC CAGGGCCGGT AAGTCCAAGC | 27850 |
| AGCCGCCGCC GTTAGCCCAA GAGCAACAAC AGCGCCAAGG CTACCGCTCA | 27900 |
| TGGCGCGGGC ACAAGAACGC CATAGTTGCT TGCTTGCAAG ACTGTGGGGG | 27950 |
| CAACATCTCC TTCGCCCGCC GCTTTCTTCT CTACCATCAC GGCGTGGCCT | 28000 |
| TCCCCCGTAA CATCCTGCAT TACTACCGTC ATCTCTACAG CCCATACTGC | 28050 |
| ACCGGCGGCA GCGGCAGCGG CAGCAACAGC AGCGGCCACA CAGAAGCAAA | 28100 |
| GGCGACCGGA TAGCAAGACT CTGACAAAGC CCAAGAAATC CACAGCGGCG | 28150 |
| GCAGCAGCAG GAGGAGGAGC GCTGCGTCTG GCGCCCAACG AACCCGTATC | 28200 |
| GACCCGCGAG CTTAGAAACA GGATTTTTCC CACTCTGTAT GCTATATTTC | 28250 |
| AACAGAGCAG GGGCCAAGAA CAAGAGCTGA AAATAAAAAA CAGGTCTCTG | 28300 |
| CGATCCCTCA CCCGCAGCTG CCTGTATCAC AAAAGCGAAG ATCAGCTTCG | 28350 |
| GCGCACGCTG GAAGACGCGG AGGCTCTCTT CAGTAAATAC TGCGCGCTGA | 28400 |
| CTCTTAAGGA CTAGTTTCGC GCCCTTTCTC AAATTTAAGC GCGAAAACTA | 28450 |
| CGTCATCTCC AGCGGCCACA CCCGGCGCCA GCACCTGTCG TCAGCGCCAT | 28500 |
| TATGAGCAAG GAAATTCCCA CGCCCTACAT GTGGAGTTAC CAGCCACAAA | 28550 |
| TGGGACTTGC GGCTGGAGCT GCCCAAGACT ACTCAACCCG AATAAACTAC | 28600 |
| ATGAGCGCGG GACCCCACAT GATATCCCGG GTCAACGGAA TCCGCGCCCA | 28650 |
| CCGAAACCGA ATTCTCTTGG AACAGGCGGC TATTACCACC ACACCTCGTA | 28700 |
| ATAACCTTAA TCCCCGTAGT TGGCCCGCTG CCCTGGTGTA CCAGGAAAGT | 28750 |
| CCCGCTCCCA CCACTGTGGT ACTTCCCAGA GACGCCCAGG CCGAAGTTCA | 28800 |
| GATGACTAAC TCAGGGCGCG AGCTTGCGGG CGGCTTTCGT CACAGGGTGC | 28850 |
| GGTCGCCCGG GCAGGGTATA ACTCACCTGA CAATCAGAGG GCGAGGTATT | 28900 |
| CAGCTCAACG ACGAGTCGGT GAGCTCCTCG CTTGGTCTCC GTCCGGACGG | 28950 |
| GACATTTCAG ATCGGCGGCG CCGGCCGTCC TTCATTCACG CCTCGTCAGG | 29000 |
| CAATCCTAAC TCTGCAGACC TCGTCCTCTG AGCCGCGCTC TGGAGGCATT | 29050 |
| GGAACTCTGC AATTTATTGA GGAGTTTGTG CCATCGGTCT ACTTTAACCC | 29100 |
| CTTCTCGGGA CCTCCCGGCC ACTATCCGGA TCAATTTATT CCTAACTTTG | 29150 |
| ACGCGGTAAA GGACTCGGCG GACGGCTACG ACTGAATGTT AAGTGGAGAG | 29200 |
| GCAGAGCAAC TGCGCCTGAA ACACCTGGTC CACTGTCGCC GCCACAAGTG | 29250 |
| CTTTGCCCGC GACTCCGGTG AGTTTTGCTA CTTTGAATTG CCCGAGGATC | 29300 |
| ATATCGAGGG CCCGGCGCAC GGCGTCCGGC TTACCGCCCA GGGAGAGCTT | 29350 |
| GCCCGTAGCC TGATTCGGGA GTTTACCCAG CGCCCCCTGC TAGTTGAGCG | 29400 |
| GGACAGGGGA CCCTGTGTTC TCACTGTGAT TTGCAACTGT CCTAACCTTG | 29450 |
| GATTACATCA AGATCTTTGT TGCCATCTCT GTGCTGAGTA TAATAAATAC | 29500 |
| AGAAATTAAA ATATACTGGG GCTCCTATCG CCATCCTGTA AACGCCACCG | 29550 |
| TCTTCACCCG CCCAAGCAAA CCAAGGCGAA CCTTACCTGG TACTTTTAAC | 29600 |
| ATCTCTCCCT CTGTGATTTA CAACAGTTTC AACCCAGACG GAGTGAGTCT | 29650 |

| | |
|---|---|
| ACGAGAGAAC CTCTCCGAGC TCAGCTACTC CATCAGAAAA AACACCACCC | 29700 |
| TCCTTACCTG CCGGGAACGT ACGAGTGCGT CACCGGCCGC TGCACCACAC | 29750 |
| CTACCGCCTG ACCGTAAACC AGACTTTTTC CGGACAGACC TCAATAACTC | 29800 |
| TGTTTACCAG AACAGGAGGT GAGCTTAGAA AACCCTTAGG GTATTAGGCC | 29850 |
| AAAGGCGCAG CTACTGTGGG GTTTATGAAC AATTCAAGCA ACTCTACGGG | 29900 |
| CTATTCTAAT TCAGGTTTCT CTAGAATCGG GGTTGGGGTT ATTCTCTGTC | 29950 |
| TTGTGATTCT CTTTATTCTT ATACTAACGC TTCTCTGCCT AAGGCTCGCC | 30000 |
| GCCTGCTGTG TGCACATTTG CATTTATTGT CAGCTTTTA AACGCTGGGG | 30050 |
| TCGCCACCCA AGATGATTAG GTACATAATC CTAGGTTTAC TCACCCTTGC | 30100 |
| GTCAGCCCAC GGTACCACCC AAAAGGTGGA TTTTAAGGAG CCAGCCTGTA | 30150 |
| ATGTTACATT CGCAGCTGAA GCTAATGAGT GCACCACTCT TATAAAATGC | 30200 |
| ACCACAGAAC ATGAAAAGCT GCTTATTCGC CACAAAAACA AAATTGGCAA | 30250 |
| GTATGCTGTT TATGCTATTT GGCAGCCAGG TGACACTACA GAGTATAATG | 30300 |
| TTACAGTTTT CCAGGGTAAA AGTCATAAAA CTTTTATGTA TACTTTTCCA | 30350 |
| TTTTATGAAA TGTGCGACAT TACCATGTAC ATGAGCAAAC AGTATAAGTT | 30400 |
| GTGGCCCCCA CAAAATTGTG TGGAAAACAC TGGCACTTTC TGCTGCACTG | 30450 |
| CTATGCTAAT TACAGTGCTC GCTTTGGTCT GTACCCTACT CTATATTAAA | 30500 |
| TACAAAAGCA GACGCAGCTT TATTGAGGAA AAGAAAATGC CTTAATTTAC | 30550 |
| TAAGTTACAA AGCTAATGTC ACCACTAACT GCTTTACTCG CTGCTTGCAA | 30600 |
| AACAAATTCA AAAAGTTAGC ATTATAATTA GAATAGGATT TAAACCCCCC | 30650 |
| GGTCATTTCC TGCTCAATAC CATTCCCCTG AACAATTGAC TCTATGTGGG | 30700 |
| ATATGCTCCA GCGCTACAAC CTTGAAGTCA GGCTTCCTGG ATGTCAGCAT | 30750 |
| CTGACTTTGG CCAGCACCTG TCCCGCGGAT TTGTTCCAGT CCAACTACAG | 30800 |
| CGACCCACCC TAACAGAGAT GACCAACACA ACCAACGCGG CCGCCGCTAC | 30850 |
| CGGACTTACA TCTACCACAA ATACACCCCA AGTTTCTGCC TTTGTCAATA | 30900 |
| ACTGGGATAA CTTGGGCATG TGGTGGTTCT CCATAGCGCT TATGTTTGTA | 30950 |
| TGCCTTATTA TTATGTGGCT CATCTGCTGC CTAAAGCGCA AACGCGCCCG | 31000 |
| ACCACCCATC TATAGTCCCA TCATTGTGCT ACACCCAAAC AATGATGGAA | 31050 |
| TCCATAGATT GGACGGACTG AAACACATGT TCTTTTCTCT TACAGTATGA | 31100 |
| TTAAATGAGA CATGATTCCT CGAGTTTTTA TATTACTGAC CCTTGTTGCG | 31150 |
| CTTTTTTGTG CGTGCTCCAC ATTGGCTGCG GTTTCTCACA TCGAAGTAGA | 31200 |
| CTGCATTCCA GCCTTCACAG TCTATTTGCT TTACGGATTT GTCACCCTCA | 31250 |
| CGCTCATCTG CAGCCTCATC ACTGTGGTCA TCGCCTTTAT CCAGTGCATT | 31300 |
| GACTGGGTCT GTGTGCGCTT TGCATATCTC AGACACCATC CCCAGTACAG | 31350 |
| GGACAGGACT ATAGCTGAGC TTCTTAGAAT TCTTTAATTA TGAAATTTAC | 31400 |
| TGTGACTTTT CTGCTGATTA TTTGCACCCT ATCTGCGTTT TGTTCCCCGA | 31450 |
| CCTCCAAGCC TCAAAGACAT ATATCATGCA GATTCACTCG TATATGGAAT | 31500 |
| ATTCCAAGTT GCTACAATGA AAAAAGCGAT CTTTCCGAAG CCTGGTTATA | 31550 |
| TGCAATCATC TCTGTTATGG TGTTCTGCAG TACCATCTTA GCCCTAGCTA | 31600 |
| TATATCCCTA CCTTGACATT GGCTGGAAAC GAATAGATGC CATGAACCAC | 31650 |

-continued

| | |
|---|---|
| CCAACTTTCC CCGCGCCCGC TATGCTTCCA CTGCAACAAG TTGTTGCCGG | 31700 |
| CGGCTTTGTC CCAGCCAATC AGCCTCGCCC CACTTCTCCC ACCCCCACTG | 31750 |
| AAATCAGCTA CTTTAATCTA ACAGGAGGAG ATGACTGACA CCCTAGATCT | 31800 |
| AGAAATGGAC GGAATTATTA CAGAGCAGCG CCTGCTAGAA AGACGCAGGG | 31850 |
| CAGCGGCCGA GCAACAGCGC ATGAATCAAG AGCTCCAAGA CATGGTTAAC | 31900 |
| TTGCACCAGT GCAAAAGGGG TATCTTTTGT CTGGTAAAGC AGGCCAAAGT | 31950 |
| CACCTACGAC AGTAATACCA CCGGACACCG CCTTAGCTAC AAGTTGCCAA | 32000 |
| CCAAGCGTCA GAAATTGGTG GTCATGGTGG GAGAAAAGCC CATTACCATA | 32050 |
| ACTCAGCACT CGGTAGAAAC CGAAGGCTGC ATTCACTCAC CTTGTCAAGG | 32100 |
| ACCTGAGGAT CTCTGCACCC TTATTAAGAC CCTGTGCGGT CTCAAAGATC | 32150 |
| TTATTCCCTT TAACTAATAA AAAAAAATAA TAAAGCATCA CTTACTTAAA | 32200 |
| ATCAGTTAGC AAATTTCTGT CCAGTTTATT CAGCAGCACC TCCTTGCCCT | 32250 |
| CCTCCCAGCT CTGGTATTGC AGCTTCCTCC TGGCTGCAAA CTTTCTCCAC | 32300 |
| AATCTAAATG GAATGTCAGT TTCCTCCTGT TCCTGTCCAT CCGCACCCAC | 32350 |
| TATCTTCATG TTGTTGCAGA TGAAGCGCGC AAGACCGTCT GAAGATACCT | 32400 |
| TCAACCCCGT GTATCCATAT GACACGGAAA CCGGTCCTCC AACTGTGCCT | 32450 |
| TTTCTTACTC CTCCCTTTGT ATCCCCCAAT GGGTTTCAAG AGAGTCCCCC | 32500 |
| TGGGGTACTC TCTTTGCGCC TATCCGAACC TCTAGTTACC TCCAATGGCA | 32550 |
| TGCTTGCGCT CAAAATGGGC AACGGCCTCT CTCTGGACGA GGCCGGCAAC | 32600 |
| CTTACCTCCC AAAATGTAAC CACTGTGAGC CCACCTCTCA AAAAAACCAA | 32650 |
| GTCAAACATA AACCTGGAAA TATCTGCACC CCTCACAGTT ACCTCAGAAG | 32700 |
| CCCTAACTGT GGCTGCCGCC GCACCTCTAA TGGTCGCGGG CAACACACTC | 32750 |
| ACCATGCAAT CACAGGCCCC GCTAACCGTG CACGACTCCA AACTTAGCAT | 32800 |
| TGCCACCCAA GGACCCCTCA CAGTGTCAGA AGGAAAGCTA GCCCTGCAAA | 32850 |
| CATCAGGCCC CCTCACCACC ACCGATAGCA GTACCCTTAC TATCACTGCC | 32900 |
| TCACCCCCTC TAACTACTGC CACTGGTAGC TTGGGCATTG ACTTGAAAGA | 32950 |
| GCCCATTTAT ACACAAAATG GAAAACTAGG ACTAAAGTAC GGGGCTCCTT | 33000 |
| TGCATGTAAC AGACGACCTA AACACTTTGA CCGTAGCAAC TGGTCCAGGT | 33050 |
| GTGACTATTA ATAATACTTC CTTGCAAACT AAAGTTACTG GAGCCTTGGG | 33100 |
| TTTTGATTCA CAAGGCAATA TGCAACTTAA TGTAGCAGGA GGACTAAGGA | 33150 |
| TTGATTCTCA AAACAGACGC CTTATACTTG ATGTTAGTTA TCCGTTTGAT | 33200 |
| GCTCAAAACC AACTAAATCT AAGACTAGGA CAGGGCCCTC TTTTTATAAA | 33250 |
| CTCAGCCCAC AACTTGGATA TTAACTACAA CAAAGGCCTT TACTTGTTTA | 33300 |
| CAGCTTCAAA CAATTCCAAA AAGCTTGAGG TTAACCTAAG CACTGCCAAG | 33350 |
| GGGTTGATGT TTGACGCTAC AGCCATAGCC ATTAATGCAG GAGATGGGCT | 33400 |
| TGAATTTGGT TCACCTAATG CACCAAACAC AAATCCCCTC AAAACAAAAA | 33450 |
| TTGGCCATGG CCTAGAATTT GATTCAAACA AGGCTATGGT TCCTAAACTA | 33500 |
| GGAACTGGCC TTAGTTTTGA CAGCACAGGT GCCATTACAG TAGGAAACAA | 33550 |
| AAATAATGAT AAGCTAACTT TGTGGACCAC ACCAGCTCCA TCTCCTAACT | 33600 |

```
GTAGACTAAA TGCAGAGAAA GATGCTAAAC TCACTTTGGT CTTAACAAAA        33650

TGTGGCAGTC AAATACTTGC TACAGTTTCA GTTTTGGCTG TTAAAGGCAG        33700

TTTGGCTCCA ATATCTGGAA CAGTTCAAAG TGCTCATCTT ATTATAAGAT        33750

TTGACGAAAA TGGAGTGCTA CTAAACAATT CCTTCCTGGA CCCAGAATAT        33800

TGGAACTTTA GAAATGGAGA TCTTACTGAA GGCACAGCCT ATACAAACGC        33850

TGTTGGATTT ATGCCTAACC TATCAGCTTA TCCAAAATCT CACGGTAAAA        33900

CTGCCAAAAG TAACATTGTC AGTCAAGTTT ACTTAAACGG AGACAAAACT        33950

AAACCTGTAA CACTAACCAT TACACTAAAC GGTACACAGG AAACAGGAGA        34000

CACAACTCCA AGTGCATACT CTATGTCATT TTCATGGGAC TGGTCTGGCC        34050

ACAACTACAT TAATGAAATA TTTGCCACAT CCTCTTACAC TTTTTCATAC        34100

ATTGCCCAAG AATAAAGAAT CGTTTGTGTT ATGTTTCAAC GTGTTTATTT        34150

TTCAATTGCA GAAAATTTCA AGTCATTTTT CATTCAGTAG TATAGCCCCA        34200

CCACCACATA GCTTATACAG ATCACCGTAC CTTAATCAAA CTCACAGAAC        34250

CCTAGTATTC AACCTGCCAC CTCCCTCCCA ACACACAGAG TACACAGTCC        34300

TTTCTCCCCG GCTGGCCTTA AAAAGCATCA TATCATGGGT AACAGACATA        34350

TTCTTAGGTG TTATATTCCA CACGGTTTCC TGTCGAGCCA AACGCTCATC        34400

AGTGATATTA ATAAACTGGC GGCGATATAA AATGCAAGGT GCTGCTCAAA        34450

AAATCAGGCA AAGCCTCGCG CAAAAAAGAA AGCACATCGT AGTCATGCTC        34500

ATGCAGATAA AGGCAGGTAA GCTCCGGAAC CACCACAGAA AAAGCACCA         34550

TTTTTCTCTC AAACATGTCT GCGGGTTTCT GCATAAACAC AAAATAAAAT        34600

AACAAAAAAA CATTTAAACA TTAGAAGCCT GTCTTACAAC AGGAAAAACA        34650

ACCCTTATAA GCATAAGACG GACTACGGCC ATGCCGGCGT GACCGTAAAA        34700

AAACTGGTCA CCGTGATTAA AAAGCACCAC CGACAGCTCC TCGGTCATGT        34750

CCGGAGTCAT AATGTAAGAC TCGGTAAACA CATCAGGTTG ATTCATCGGT        34800

CAGTGCTAAA AAGCGACCGA ATAGCCCGG GGGAATACAT ACCCGCAGGC         34850

GTAGAGACAA CATTACAGCC CCCATAGGAG GTATAACAAA ATTAATAGGA        34900

GAGAAAAACA CATAAACACC TGAAAAACCC TCCTGCCTAG GCAAAATAGC        34950

ACCCTCCCGC TCCAGAACAA CATACAGCGC TTCACAGCGG CAGCCTAACA        35000

GTCAGCCTTA CCAGTAAAAA AGAAAACCTA TTAAAAAAAC ACCACTCGAC        35050

ACGGCACCAG CTCAATCAGT CACAGTGTAA AAAAGGGCCA AGTGCAGAGC        35100

GAGTATATAT AGGACTAAAA AATGACGTAA CGGTTAAAGT CCACAAAAAA        35150

CACCCAGAAA ACCGCACGCG AACCTACGCC CAGAAACGAA AGCCAAAAAA        35200

CCCACAACTT CCTCAAATCG TCACTTCCGT TTTCCCACGT TACGTAACTT        35250

CCCATTTTAA GAAAACTACA ATTCCCAACA CATACAAGTT ACTCCGCCCT        35300

AAAACCTACG TCACCCGCCC CGTTCCCACG CCCCGCGCCA CGTCACAAAC        35350

TCCACCCCCT CATTATCATA TTGGCTTCAA TCCAAAATAA GGTATATTAT        35400

TGATGATG                                                     35408
```

(2) INFORMATION FOR SEQ ID NO:4:

(i) SEQUENCE CHARACTERISTICS:
        (A) LENGTH: 8509 base pairs (B) TYPE: nucleic acid
    (C) STRANDEDNESS: double
    (D) TOPOLOGY: Not Relevant (ii) MOLECULE TYPE: cDNA (xi) SEQUENCE DESCRIPTION: SEQ ID NO:4:

| | | |
|---|---|---|
| GCCCAATACG | CAAACCGCCT CTCCCCGCGC GTTGGCCGAT TCATTAATGC | 50 |
| AGCTGCGCGC | TCGCTCGCTC ACTGAGGCCG CCCGGGCAAA GCCCGGGCGT | 100 |
| CGGGCGACCT | TTGGTCGCCC GGCCTCAGTG AGCGAGCGAG CGCGCAGAGA | 150 |
| GGGAGTGGCC | AACTCCATCA CTAGGGGTTC CTTGTAGTTA ATGATTAACC | 200 |
| CGCCATGCTA | CTTATCTACG TAGCCATTCT CTAGCCCCTG CAGGTCGTTA | 250 |
| CATAACTTAC | GGTAAATGGC CCGCCTGGCT GACCGCCCAA CGACCCCGC | 300 |
| CCATTGACGT | CAATAATGAC GTATGTTCCC ATAGTAACGC CAATAGGGAC | 350 |
| TTTCCATTGA | CGTCAATGGG TGGAGTATTT ACGGTAAACT GCCCACTTGG | 400 |
| CAGTACATCA | AGTGTATCAT ATGCCAAGTA CGCCCCCTAT TGACGTCAAT | 450 |
| GACGGTAAAT | GGCCCGCCTG GCATTATGCC CAGTACATGA CCTTATGGGA | 500 |
| CTTTCCTACT | TGGCAGTACA TCTACGTATT AGTCATCGCT ATTACCATGG | 550 |
| TGATGCGGTT | TTGGCAGTAC ATCAATGGGC GTGGATAGCG GTTTGACTCA | 600 |
| CGGGGATTTC | CAAGTCTCCA CCCCATTGAC GTCAATGGGA GTTTGTTTTG | 650 |
| GCACCAAAAT | CAACGGGACT TTCCAAAATG TCGTAACAAC TCCGCCCCAT | 700 |
| TGACGCAAAT | GGGCGGTAGG CGTGTACGGT GGGAGGTCTA TATAAGCAGA | 750 |
| GCTCGTTTAG | TGAACCGTCA GATCGCCTGG AGACGCCATC CACGCTGTTT | 800 |
| TGACCTCCAT | AGAAGACACC GGGACCGATC CAGCCTCCGG ACTCTAGAGG | 850 |
| ATCCGGTACT | CGAGGAACTG AAAAACCAGA AAGTTAACTG GTAAGTTTAG | 900 |
| TCTTTTTGTC | TTTTATTTCA GGTCCCGGAT CCGGTGGTGG TGCAAATCAA | 950 |
| AGAACTGCTC | TCAGTGGAT GTTGCCTTTA CTTCTAGGCC TGTACGGAAG | 1000 |
| TGTTACTTCT | GCTCTAAAAG CTGCGGAATT GTACCCGCGG CCGCAATTCC | 1050 |
| CGGGGATCGA | AAGAGCCTGC TAAAGCAAAA AAGAAGTCAC CATGTCGTTT | 1100 |
| ACTTTGACCA | ACAAGAACGT GATTTTCGTT GCCGGTCTGG GAGGCATTGG | 1150 |
| TCTGGACACC | AGCAAGGAGC TGCTCAAGCG CGATCCCGTC GTTTTACAAC | 1200 |
| GTCGTGACTG | GGAAAACCCT GGCGTTACCC AACTTAATCG CCTTGCAGCA | 1250 |
| CATCCCCCTT | TCGCCAGCTG GCGTAATAGC GAAGAGGCCC GCACCGATCG | 1300 |
| CCCTTCCCAA | CAGTTGCGCA GCCTGAATGG CGAATGGCGC TTTGCCTGGT | 1350 |
| TTCCGGCACC | AGAAGCGGTG CCGGAAAGCT GGCTGGAGTG CGATCTTCCT | 1400 |
| GAGGCCGATA | CTGTCGTCGT CCCCTCAAAC TGGCAGATGC ACGGTTACGA | 1450 |
| TGCGCCCATC | TACACCAACG TAACCTATCC CATTACGGTC AATCCGCCGT | 1500 |
| TTGTTCCCAC | GGAGAATCCG ACGGGTTGTT ACTCGCTCAC ATTTAATGTT | 1550 |
| GATGAAAGCT | GGCTACAGGA AGGCCAGACG CGAATTATTT TTGATGGCGT | 1600 |
| TAACTCGGCG | TTTCATCTGT GGTGCAACGG GCGCTGGGTC GGTTACGGCC | 1650 |
| AGGACAGTCG | TTTGCCGTCT GAATTTGACC TGAGCGCATT TTTACGCGCC | 1700 |
| GGAGAAAACC | GCCTCGCGGT GATGGTGCTG CGTTGGAGTG ACGGCAGTTA | 1750 |
| TCTGGAAGAT | CAGGATATGT GGCGGATGAG CGGCATTTTC CGTGACGTCT | 1800 |

-continued

| | |
|---|---|
| CGTTGCTGCA TAAACCGACT ACACAAATCA GCGATTTCCA TGTTGCCACT | 1850 |
| CGCTTTAATG ATGATTTCAG CCGCGCTGTA CTGGAGGCTG AAGTTCAGAT | 1900 |
| GTGCGGCGAG TTGCGTGACT ACCTACGGGT AACAGTTTCT TTATGGCAGG | 1950 |
| GTGAAACGCA GGTCGCCAGC GGCACCGCGC CTTTCGGCGG TGAAATTATC | 2000 |
| GATGAGCGTG GTGGTTATGC CGATCGCGTC ACACTACGTC TGAACGTCGA | 2050 |
| AAACCCGAAA CTGTGGAGCG CCGAAATCCC GAATCTCTAT CGTGCGGTGG | 2100 |
| TTGAACTGCA CACCGCCGAC GGCACGCTGA TTGAAGCAGA AGCCTGCGAT | 2150 |
| GTCGGTTTCC GCGAGGTGCG GATTGAAAAT GGTCTGCTGC TGCTGAACGG | 2200 |
| CAAGCCGTTG CTGATTCGAG GCGTTAACCG TCACGAGCAT CATCCTCTGC | 2250 |
| ATGGTCAGGT CATGGATGAG CAGACGATGG TGCAGGATAT CCTGCTGATG | 2300 |
| AAGCAGAACA ACTTTAACGC CGTGCGCTGT TCGCATTATC CGAACCATCC | 2350 |
| GCTGTGGTAC ACGCTGTGCG ACCGCTACGG CCTGTATGTG GTGGATGAAG | 2400 |
| CCAATATTGA AACCCACGGC ATGGTGCCAA TGAATCGTCT GACCGATGAT | 2450 |
| CCGCGCTGGC TACCGGCGAT GAGCGAACGC GTAACGCGAA TGGTGCAGCG | 2500 |
| CGATCGTAAT CACCCGAGTG TGATCATCTG GTCGCTGGGG AATGAATCAG | 2550 |
| GCCACGGCGC TAATCACGAC GCGCTGTATC GCTGGATCAA ATCTGTCGAT | 2600 |
| CCTTCCCGCC CGGTGCAGTA TGAAGGCGGC GGAGCCGACA CCACGGCCAC | 2650 |
| CGATATTATT TGCCCGATGT ACGCGCGCGT GGATGAAGAC CAGCCCTTCC | 2700 |
| CGGCTGTGCC GAAATGGTCC ATCAAAAAAT GGCTTTCGCT ACCTGGAGAG | 2750 |
| ACGCGCCCGC TGATCCTTTG CGAATACGCC CACGCGATGG GTAACAGTCT | 2800 |
| TGGCGGTTTC GCTAAATACT GGCAGGCGTT TCGTCAGTAT CCCCGTTTAC | 2850 |
| AGGGCGGCTT CGTCTGGGAC TGGGTGGATC AGTCGCTGAT TAAATATGAT | 2900 |
| GAAAACGGCA ACCCGTGGTC GGCTTACGGC GGTGATTTTG GCGATACGCC | 2950 |
| GAACGATCGC CAGTTCTGTA TGAACGGTCT GGTCTTTGCC GACCGCACGC | 3000 |
| CGCATCCAGC GCTGACGGAA GCAAAACACC AGCAGCAGTT TTTCCAGTTC | 3050 |
| CGTTTATCCG GGCAAACCAT CGAAGTGACC AGCGAATACC TGTTCCGTCA | 3100 |
| TAGCGATAAC GAGCTCCTGC ACTGGATGGT GGCGCTGGAT GGTAAGCCGC | 3150 |
| TGGCAAGCGG TGAAGTGCCT CTGGATGTCG CTCCACAAGG TAAACAGTTG | 3200 |
| ATTGAACTGC CTGAACTACC GCAGCCGGAG AGCGCCGGGC AACTCTGGCT | 3250 |
| CACAGTACGC GTAGTGCAAC CGAACGCGAC CGCATGGTCA GAAGCCGGGC | 3300 |
| ACATCAGCGC CTGGCAGCAG TGGCGTCTGG CGGAAAACCT CAGTGTGACG | 3350 |
| CTCCCCGCCG CGTCCCACGC CATCCCGCAT CTGACCACCA GCGAAATGGA | 3400 |
| TTTTTGCATC GAGCTGGGTA ATAAGCGTTG GCAATTTAAC CGCCAGTCAG | 3450 |
| GCTTTCTTTC ACAGATGTGG ATTGGCGATA AAAAACAACT GCTGACGCCG | 3500 |
| CTGCGCGATC AGTTCACCCG TGCACCGCTG GATAACGACA TTGGCGTAAG | 3550 |
| TGAAGCGACC CGCATTGACC CTAACGCCTG GGTCGAACGC TGGAAGGCGG | 3600 |
| CGGGCCATTA CCAGGCCGAA GCAGCGTTGT TGCAGTGCAC GGCAGATACA | 3650 |
| CTTGCTGATG CGGTGCTGAT TACGACCGCT CACGCGTGGC AGCATCAGGG | 3700 |
| GAAAACCTTA TTTATCAGCC GGAAAACCTA CCGGATTGAT GGTAGTGGTC | 3750 |

```
AAATGGCGAT TACCGTTGAT GTTGAAGTGG CGAGCGATAC ACCGCATCCG        3800
GCGCGGATTG GCCTGAACTG CCAGCTGGCG CAGGTAGCAG AGCGGGTAAA        3850
CTGGCTCGGA TTAGGGCCGC AAGAAAACTA TCCCGACCGC CTTACTGCCG        3900
CCTGTTTTGA CCGCTGGGAT CTGCCATTGT CAGACATGTA TACCCCGTAC        3950
GTCTTCCCGA GCGAAAACGG TCTGCGCTGC GGGACGCGCG AATTGAATTA        4000
TGGCCCACAC CAGTGGCGCG GCGACTTCCA GTTCAACATC AGCCGCTACA        4050
GTCAACAGCA ACTGATGGAA ACCAGCCATC GCCATCTGCT GCACGCGGAA        4100
GAAGGCACAT GGCTGAATAT CGACGGTTTC CATATGGGGA TTGGTGGCGA        4150
CGACTCCTGG AGCCCGTCAG TATCGGCGGA ATTACAGCTG AGCGCCGGTC        4200
GCTACCATTA CCAGTTGGTC TGGTGTCAAA ATAATAATA  ACCGGGCAGG        4250
CCATGTCTGC CCGTATTTCG CGTAAGGAAA TCCATTATGT ACTATTTAAA        4300
AAACACAAAC TTTTGGATGT TCGGTTTATT CTTTTTCTTT TACTTTTTTA        4350
TCATGGGAGC CTACTTCCCG TTTTTCCCGA TTTGGCTACA TGACATCAAC        4400
CATATCAGCA AAAGTGATAC GGGTATTATT TTTGCCGCTA TTTCTCTGTT        4450
CTCGCTATTA TTCCAACCGC TGTTTGGTCT GCTTTCTGAC AAACTCGGCC        4500
TCGACTCTAG GCGGCCGCGG GGATCCAGAC ATGATAAGAT ACATTGATGA        4550
GTTTGGACAA ACCACAACTA GAATGCAGTG AAAAAAATGC TTTATTTGTG        4600
AAATTTGTGA TGCTATTGCT TTATTTGTAA CCATTATAAG CTGCAATAAA        4650
CAAGTTAACA ACAACAATTG CATTCATTTT ATGTTTCAGG TTCAGGGGGA        4700
GGTGTGGGAG GTTTTTTCGG ATCCTCTAGA GTCGACCTGC AGGGGCTAGA        4750
ATGGCTACGT AGATAAGTAG CATGGCGGGT TAATCATTAA CTACAAGGAA        4800
CCCCTAGTGA TGGAGTTGGC CACTCCCTCT CTGCGCGCTC GCTCGCTCAC        4850
TGAGGCCGGG CGACCAAAGG TCGCCCGACG CCCGGGCTTT GCCCGGGCGG        4900
CCTCAGTGAG CGAGCGAGCG CGCAGCTGGC GTAATAGCGA AGAGGCCCGC        4950
ACCGATCGCC CTTCCCAACA GTTGCGCAGC CTGAATGGCG AATGGAATTC        5000
CAGACGATTG AGCGTCAAAA TGTAGGTATT TCCATGAGCG TTTTTCCTGT        5050
TGCAATGGCT GGCGGTAATA TTGTTCTGGA TATTACCAGC AAGGCCGATA        5100
GTTTGAGTTC TTCTACTCAG GCAAGTGATG TTATTACTAA TCAAAGAAGT        5150
ATTGCGACAA CGGTTAATTT GCGTGATGGA CAGACTCTTT TACTCGGTGG        5200
CCTCACTGAT TATAAAAACA CTTCTCAGGA TTCTGGCGTA CCGTTCCTGT        5250
CTAAAATCCC TTTAATCGGC CTCCTGTTTA GCTCCCGCTC TGATTCTAAC        5300
GAGGAAAGCA CGTTATACGT GCTCGTCAAA GCAACCATAG TACGCGCCCT        5350
GTAGCGGCGC ATTAAGCGCG GCGGGTGTGG TGGTTACGCG CAGCGTGACC        5400
GCTACACTTG CCAGCGCCCT AGCGCCCGCT CCTTTCGCTT TCTTCCCTTC        5450
CTTTCTCGCC ACGTTCGCCG GCTTTCCCCG TCAAGCTCTA AATCGGGGGC        5500
TCCCTTTAGG GTTCCGATTT AGTGCTTTAC GGCACCTCGA CCCCAAAAAA        5550
CTTGATTAGG GTGATGGTTC ACGTAGTGGG CCATCGCCCT GATAGACGGT        5600
TTTTCGCCCT TTGACGTTGG AGTCCACGTT CTTTAATAGT GGACTCTTGT        5650
TCCAAACTGG AACAACACTC AACCCTATCT CGGTCTATTC TTTTGATTTA        5700
TAAGGGATTT TGCCGATTTC GGCCTATTGG TTAAAAAATG AGCTGATTTA        5750
```

```
ACAAAAATTT AACGCGAATT TTAACAAAAT ATTAACGTTT ACAATTTAAA        5800

TATTTGCTTA TACAATCTTC CTGTTTTTGG GGCTTTTCTG ATTATCAACC        5850

GGGGTACATA TGATTGACAT GCTAGTTTTA CGATTACCGT TCATCGATTC        5900

TCTTGTTTGC TCCAGACTCT CAGGCAATGA CCTGATAGCC TTTGTAGAGA        5950

CCTCTCAAAA ATAGCTACCC TCTCCGGCAT GAATTTATCA GCTAGAACGG        6000

TTGAATATCA TATTGATGGT GATTTGACTG TCTCCGGCCT TTCTCACCCG        6050

TTTGAATCTT TACCTACACA TTACTCAGGC ATTGCATTTA AAATATATGA        6100

GGGTTCTAAA AATTTTTATC CTTGCGTTGA AATAAAGGCT TCTCCCGCAA        6150

AAGTATTACA GGGTCATAAT GTTTTTGGTA CAACCGATTT AGCTTTATGC        6200

TCTGAGGCTT TATTGCTTAA TTTTGCTAAT TCTTTGCCTT GCCTGTATGA        6250

TTTATTGGAT GTTGGAATTC CTGATGCGGT ATTTTCTCCT TACGCATCTG        6300

TGCGGTATTT CACACCGCAT ATGGTGCACT CTCAGTACAA TCTGCTCTGA        6350

TGCCGCATAG TTAAGCCAGC CCCGACACCC GCCAACACCC GCTGACGCGC        6400

CCTGACGGGC TTGTCTGCTC CCGGCATCCG CTTACAGACA AGCTGTGACC        6450

GTCTCCGGGA GCTGCATGTG TCAGAGGTTT TCACCGTCAT CACCGAAACG        6500

CGCGAGACGA AAGGGCCTCG TGATACGCCT ATTTTTATAG GTTAATGTCA        6550

TGATAATAAT GGTTTCTTAG ACGTCAGGTG GCACTTTTCG GGGAAATGTG        6600

CGCGGAACCC CTATTTGTTT ATTTTTCTAA ATACATTCAA ATATGTATCC        6650

GCTCATGAGA CAATAACCCT GATAAATGCT TCAATAATAT TGAAAAAGGA        6700

AGAGTATGAG TATTCAACAT TTCCGTGTCG CCCTTATTCC CTTTTTTGCG        6750

GCATTTTGCC TTCCTGTTTT TGCTCACCCA GAAACGCTGG TGAAAGTAAA        6800

AGATGCTGAA GATCAGTTGG GTGCACGAGT GGGTTACATC GAACTGGATC        6850

TCAACAGCGG TAAGATCCTT GAGAGTTTTC GCCCCGAAGA ACGTTTTCCA        6900

ATGATGAGCA CTTTTAAAGT TCTGCTATGT GGCGCGGTAT TATCCCGTAT        6950

TGACGCCGGG CAAGAGCAAC TCGGTCGCCG CATACACTAT TCTCAGAATG        7000

ACTTGGTTGA GTACTCACCA GTCACAGAAA AGCATCTTAC GGATGGCATG        7050

ACAGTAAGAG AATTATGCAG TGCTGCCATA ACCATGAGTG ATAACACTGC        7100

GGCCAACTTA CTTCTGACAA CGATCGGAGG ACCGAAGGAG CTAACCGCTT        7150

TTTTGCACAA CATGGGGGAT CATGTAACTC GCCTTGATCG TTGGGAACCG        7200

GAGCTGAATG AAGCCATACC AAACGACGAG CGTGACACCA CGATGCCTGT        7250

AGCAATGGCA ACAACGTTGC GCAAACTATT AACTGGCGAA CTACTTACTC        7300

TAGCTTCCCG GCAACAATTA ATAGACTGGA TGGAGGCGGA TAAAGTTGCA        7350

GGACCACTTC TGCGCTCGGC CCTTCCGGCT GGCTGGTTTA TTGCTGATAA        7400

ATCTGGAGCC GGTGAGCGTG GGTCTCGCGG TATCATTGCA GCACTGGGGC        7450

CAGATGGTAA GCCCTCCCGT ATCGTAGTTA TCTACACGAC GGGGAGTCAG        7500

GCAACTATGG ATGAACGAAA TAGACAGATC GCTGAGATAG GTGCCTCACT        7550

GATTAAGCAT TGGTAACTGT CAGACCAAGT TTACTCATAT ATACTTTAGA        7600

TTGATTTAAA ACTTCATTTT TAATTTAAAA GGATCTAGGT GAAGATCCTT        7650

TTTGATAATC TCATGACCAA AATCCCTTAA CGTGAGTTTT CGTTCCACTG        7700
```

```
AGCGTCAGAC CCCGTAGAAA AGATCAAAGG ATCTTCTTGA GATCCTTTTT      7750

TTCTGCGCGT AATCTGCTGC TTGCAAACAA AAAAACCACC GCTACCAGCG      7800

GTGGTTTGTT TGCCGGATCA AGAGCTACCA ACTCTTTTTC CGAAGGTAAC      7850

TGGCTTCAGC AGAGCGCAGA TACCAAATAC TGTCCTTCTA GTGTAGCCGT      7900

AGTTAGGCCA CCACTTCAAG AACTCTGTAG CACCGCCTAC ATACCTCGCT      7950

CTGCTAATCC TGTTACCAGT GGCTGCTGCC AGTGGCGATA AGTCGTGTCT      8000

TACCGGGTTG GACTCAAGAC GATAGTTACC GGATAAGGCG CAGCGGTCGG      8050

GCTGAACGGG GGGTTCGTGC ACACAGCCCA GCTTGGAGCG AACGACCTAC      8100

ACCGAACTGA GATACCTACA GCGTGAGCTA TGAGAAAGCG CCACGCTTCC      8150

CGAAGGGAGA AAGGCGGACA GGTATCCGGT AAGCGGCAGG GTCGGAACAG      8200

GAGAGCGCAC GAGGGAGCTT CCAGGGGGAA ACGCCTGGTA TCTTTATAGT      8250

CCTGTCGGGT TTCGCCACCT CTGACTTGAG CGTCGATTTT TGTGATGCTC      8300

GTCAGGGGGG CGGAGCCTAT GGAAAAACGC CAGCAACGCG GCCTTTTTAC      8350

GGTTCCTGGC CTTTTGCTGG CCTTTTGCTC ACATGTTCTT TCCTGCGTTA      8400

TCCCCTGATT CTGTGGATAA CCGTATTACC GCCTTTGAGT GAGCTGATAC      8450

CGCTCGCCGC AGCCGAACGA CCGAGCGCAG CGAGTCAGTG AGCGAGGAAG      8500

CGGAAGAGC                                                   8509

(2) INFORMATION FOR SEQ ID NO:5:

(i) SEQUENCE CHARACTERISTICS:
        (A) LENGTH: 8299 base pairs
        (B) TYPE: nucleic acid
        (C) STRANDEDNESS: double
        (D) TOPOLOGY: Not Relevant (ii) MOLECULE TYPE: cDNA (xi) SEQUENCE DESCRIPTION: SEQ ID NO:5:

GCCCAATACG CAAACCGCCT CTCCCCGCGC GTTGGCCGAT TCATTAATGC        50

AGCTGCGCGC TCGCTCGCTC ACTGAGGCCG CCCGGGCAAA GCCCGGGCGT       100

CGGGCGACCT TTGGTCGCCC GGCCTCAGTG AGCGAGCGAG CGCGCAGAGA       150

GGGAGTGGCC AACTCCATCA CTAGGGGTTC CTTGTAGTTA ATGATTAACC       200

CGCCATGCTA CTTATCTACA TCATCGATGA ATTCGAGCTT GCATGCCTGC       250

AGGTCGTTAC ATAACTTACG GTAAATGGCC CGCCTGGCTG ACCGCCCAAC       300

GACCCCCGCC CATTGACGTC AATAATGACG TATGTTCCCA TAGTAACGCC       350

AATAGGGACT TTCCATTGAC GTCAATGGGT GGAGTATTTA CGGTAAACTG       400

CCCACTTGGC AGTACATCAA GTGTATCATA TGCCAAGTAC GCCCCCTATT       450

GACGTCAATG ACGGTAAATG GCCCGCCTGG CATTATGCCC AGTACATGAC       500

CTTATGGGAC TTTCCTACTT GGCAGTACAT CTACGTATTA GTCATCGCTA       550

TTACCATGGT GATGCGGTTT TGGCAGTACA TCAATGGGCG TGGATAGCGG       600

TTTGACTCAC GGGGATTTCC AAGTCTCCAC CCCATTGACG TCAATGGGAG       650

TTTGTTTTGG CACCAAAATC AACGGGACTT TCCAAAATGT CGTAACAACT       700

CCGCCCCATT GACGCAAATG GGCGGTAGGC GTGTACGGTG GGAGGTCTAT       750

ATAAGCAGAG CTCGTTTAGT GAACCGTCAG ATCGCCTGGA GACGCCATCC       800
```

-continued

| | |
|---|---|
| ACGCTGTTTT GACCTCCATA GAAGACACCG GGACCGATCC AGCCTCCGGA | 850 |
| CTCTAGAGGA TCCGGTACTC GACCCGAGCT CGGATCCACT AGTAACGGCC | 900 |
| GCCAGTGTGC TGGAATTCTG CACTCCAGGC TGCCCGGGTT TGCATGCTGC | 950 |
| TGCTGCTGCT GCTGCTGGGC CTGAGGCTAC AGCTCTCCCT GGGCATCATC | 1000 |
| CTAGTTGAGG AGGAGAACCC GGACTTCTGG AACCGCGAGG CAGCCGAGGC | 1050 |
| CCTGGGTGCC GCCAAGAAGC TGCAGCCTGC ACAGACAGCC GCCAAGAACC | 1100 |
| TCATCATCTT CCTGGGCGAT GGGATGGGGG TGTCTACGGT GACAGCTGCC | 1150 |
| AGGATCCTAA AAGGGCAGAA GAAGGACAAA CTGGGGCCTG AGATACCCCT | 1200 |
| GGCCATGGAC CGCTTCCCAT ATGTGGCTCT GTCCAAGACA TACAATGTAG | 1250 |
| ACAAACATGT GCCAGACAGT GGAGCCACAG CCACGGCCTA CCTGTGCGGG | 1300 |
| GTCAAGGGCA ACTTCCAGAC CATTGGCTTG AGTGCAGCCG CCCGCTTTAA | 1350 |
| CCAGTGCAAC ACGACACGCG GCAACGAGGT CATCTCCGTG ATGAATCGGG | 1400 |
| CCAAGAAAGC AGGGAAGTCA GTGGGAGTGG TAACCACCAC ACGAGTGCAG | 1450 |
| CACGCCTCGC CAGCCGGCAC CTACGCCCAC ACGGTGAACC GCAACTGGTA | 1500 |
| CTCGGACGCC GACGTGCCTG CCTCGGCCCG CCAGGAGGGG TGCCAGGACA | 1550 |
| TCGCTACGCA GCTCATCTCC AACATGGACA TTGATGTGAT CCTAGGTGGA | 1600 |
| GGCCGAAAGT ACATGTTTCG CATGGGAACC CCAGACCCTG AGTACCCAGA | 1650 |
| TGACTACAGC CAAGGTGGGA CCAGGCTGGA CGGGAAGAAT CTGGTGCAGG | 1700 |
| AATGGCTCGG CGAACGCCAG GGTGCCCGGT ACGTGTGGAA CCGCACTGAG | 1750 |
| CTCATGCAGG CTTCCCTGGA CCCGTCTGTG ACCCATCTCA TGGGTCTCTT | 1800 |
| TGAGCCTGGA GACATGAAAT ACGAGATCCA CCGAGACTCC ACACTGGACC | 1850 |
| CCTCCCTGAT GGAGATGACA GAGGCTGCCC TGCGCCTGCT GAGCAGACAC | 1900 |
| CCCCGCGGCT TCTTCCTCTT CGTGGAGGGT GGTCGCATCG ACCATGGTCA | 1950 |
| TCATGAAAGC AGGGCTTACC GGGCACTGAC TGAGACGATC ATGTTCGACG | 2000 |
| ACGCCATTGA GAGGGCGGGC CAGCTCACCA GCGAGGAGGA CACGCTGAGC | 2050 |
| CTCGTCACTG CCGACCACTC CCACGTCTTC TCCTTCGGAG GCTACCCCCT | 2100 |
| GCGAGGGAGC TCCTTCATCG GGCTGGCCGC TGGCAAGGCC CGGGACAGGA | 2150 |
| AGGCCTACAC GGTCCTCCTA TACGGAAACG GTCCAGGCTA TGTGCTCAAG | 2200 |
| GACGGCGCCC GGCCGGATGT TACCGAGAGC GAGAGCGGGA GCCCCGAGTA | 2250 |
| TCGGCAGCAG TCAGCAGTGC CCCTGGACGA AGAGACCCAC GCAGGCGAGG | 2300 |
| ACGTGGCGGT GTTCGCGCGC GGCCCGCAGG CGCACCTGGT TCACGGCGTG | 2350 |
| CAGGAGCAGA CCTTCATAGC GCACGTCATG GCCTTCGCCG CCTGCCTGGA | 2400 |
| GCCCTACACC GCCTGCGACC TGGCGCCCCC CGCCGGCACC ACCGACGCCG | 2450 |
| CGCACCCGGG GCGGTCCGTG GTCCCCGCGT TGCTTCCTCT GCTGGCCGGG | 2500 |
| ACCCTGCTGC TGCTGGAGAC GGCCACTGCT CCCTGAGTGT CCCGTCCCTG | 2550 |
| GGGCTCCTGC TTCCCCATCC CGGAGTTCTC CTGCTCCCCA CCTCCTGTCG | 2600 |
| TCCTGCCTGG CCTCCAGCCC GAGTCGTCAT CCCCGGAGTC CCTATACAGA | 2650 |
| GGTCCTGCCA TGGAACCTTC CCCTCCCCGT GCGCTCTGGG GACTGAGCCC | 2700 |
| ATGACACCAA ACCTGCCCCT TGGCTGCTCT CGGACTCCCT ACCCCAACCC | 2750 |
| CAGGGACTGC AGGTTGTGCC CTGTGGCTGC CTGCACCCCA GGAAAGGAGG | 2800 |

| | |
|---|---|
| GGGCTCAGGC CATCCAGCCA CCACCTACAG CCCAGTGGGG TCGAGACAGA | 2850 |
| TGGTCAGTCT GGAGGATGAC GTGGCGTGAA GCTGGCCGCG GGGATCCAGA | 2900 |
| CATGATAAGA TACATTGATG AGTTTGGACA AACCACAACT AGAATGCAGT | 2950 |
| GAAAAAAATG CTTTATTTGT GAAATTTGTG ATGCTATTGC TTTATTTGTA | 3000 |
| ACCATTATAA GCTGCAATAA ACAAGTTAAC AACAACAATT GCATTCATTT | 3050 |
| TATGTTTCAG GTTCAGGGGG AGGTGTGGGA GGTTTTTTCG GATCCTCTAG | 3100 |
| AGTCGACTCT AGANNNNNNN NNNNNNNNNN NNNNNNNNNN NNNNNNNNNN | 3150 |
| NNNNNNNNNN NNNNNNNNNN NNNNNNNNNN NNNNNNNNNN NNNNNNNNNN | 3200 |
| NNNNNNNNNN NNNNNNNNNN NNNNNNNNNN NNNNNNNNNN NNNNNNNNNN | 3250 |
| NNNNNNNNNN NNNNNNNNNN NNNNNNNNNN NNNNNNNNNN NNNNNNNNNN | 3300 |
| NNNNNNNNNN NNNNNNNNNN NNNNNNNNNN NNNNNNNNNN NNNNNNNNNN | 3350 |
| NNNNNNNNNN NNNNNNNNNN NNNNNNNNNN NNNNNNNNNN NNNGGATCCC | 3400 |
| CATGACTACG TCCGGCGTTC CATTTGGCAT GACACTACGA CCAACACGAT | 3450 |
| CTCGGTTGTC TCGGCGCACT CCGTACAGTA GGGATCGTCT ACCTCCTTTT | 3500 |
| GAGACAGAAA CCCGCGCTAC CATACTGGAG GATCATCCGC TGCTGCCCGA | 3550 |
| ATGTAACACT TTGACAATGC ACAACGTGAG TTACGTGCGA GGTCTTCCCT | 3600 |
| GCAGTGTGGG ATTTACGCTG ATTCAGGAAT GGGTTGTTCC CTGGGATATG | 3650 |
| GTTCTAACGC GGGAGGAGCT TGTAATCCTG AGGAAGTGTA TGCACGTGTG | 3700 |
| CCTGTGTTGT GCCAACATTG ATATCATGAC GAGCATGATG ATCCATGGTT | 3750 |
| ACGAGTCCTG GGCTCTCCAC TGTCATTGTT CCAGTCCCGG TTCCCTGCAG | 3800 |
| TGTATAGCCG GCGGGCAGGT TTTGGCCAGC TGGTTTAGGA TGGTGGTGGA | 3850 |
| TGGCGCCATG TTTAATCAGA GGTTTATATG GTACCGGGAG GTGGTGAATT | 3900 |
| ACAACATGCC AAAAGAGGTA ATGTTTATGT CCAGCGTGTT TATGAGGGGT | 3950 |
| CGCCACTTAA TCTACCTGCG CTTGTGGTAT GATGGCCACG TGGGTTCTGT | 4000 |
| GGTCCCCGCC ATGAGCTTTG GATACAGCGC CTTGCACTGT GGGATTTTGA | 4050 |
| ACAATATTGT GGTGCTGTGC TGCAGTTACT GTGCTGATTT AAGTGAGATC | 4100 |
| AGGGTGCGCT GCTGTGCCCG GAGGACAAGG CGCCTTATGC TGCGGGCGGT | 4150 |
| GCGAATCATC GCTGAGGAGA CCACTGCCAT GTTGTATTCC TGCAGGACGG | 4200 |
| AGCGGCGGCG GCAGCAGTTT ATTCGCGCGC TGCTGCAGCA CCACCGCCCT | 4250 |
| ATCCTGATGC ACGATTATGA CTCTACCCCC ATGTAGGGAT CCCCATCACT | 4300 |
| AGTGCGGCCG CGGGGATCCA GACATGATAA GATACATTGA TGAGTTTGGA | 4350 |
| CAAACCACAA CTAGAATGCA GTGAAAAAAA TGCTTTATTT GTGAAATTTG | 4400 |
| TGATGCTATT GCTTTATTTG TAACCATTAT AAGCTGCAAT AAACAAGTTA | 4450 |
| ACAACAACAA TTGCATTCAT TTTATGTTTC AGGTTCAGGG GGAGGTGTGG | 4500 |
| GAGGTTTTTT CGGATCCTCT AGAGTCGACC TGCAGGCATG CAAGCTGTAG | 4550 |
| ATAAGTAGCA TGGCGGGTTA ATCATTAACT ACAAGGAACC CCTAGTGATG | 4600 |
| GAGTTGGCCA CTCCCTCTCT GCGCGCTCGC TCGCTCACTG AGGCCGGGCG | 4650 |
| ACCAAAGGTC GCCCGACGCC CGGGCTTTGC CCGGGCGGCC TCAGTGAGCG | 4700 |
| AGCGAGCGCG CAGCTGGCGT AATAGCGAAG AGGCCCGCAC CGATCGCCCT | 4750 |

-continued

| | |
|---|---|
| TCCCAACAGT TGCGCAGCCT GAATGGCGAA TGGAANTTCC AGACGATTGA | 4800 |
| GCGTCAAAAT GTAGGTATTT CCATGAGCGT TTTTCCTGTT GCAATGGCTG | 4850 |
| GCGGTAATAT TGTTCTGGAT ATTACCAGCA AGGCCGATAG TTTGAGTTCT | 4900 |
| TCTACTCAGG CAAGTGATGT TATTACTAAT CAAAGAAGTA TTGCGACAAC | 4950 |
| GGTTAATTTG CGTGATGGAC AGACTCTTTT ACTCGGTGGC CTCACTGATT | 5000 |
| ATAAAAACAC TTCTCAGGAT CTGGCGTAC CGTTCCTGTC TAAAATCCCT | 5050 |
| TTAATCGGCC TCCTGTTTAG CTCCCGCTCT GATTCTAACG AGGAAAGCAC | 5100 |
| GTTATACGTG CTCGTCAAAG CAACCATAGT ACGCGCCCTG TAGCGGCGCA | 5150 |
| TTAAGCGCGG CGGGTGTGGT GGTTACGCGC AGCGTGACCG CTACACTTGC | 5200 |
| CAGCGCCCTA GCGCCCGCTC CTTTCGCTTT CTTCCCTTCC TTTCTCGCCA | 5250 |
| CGTTCGCCGG CTTTCCCCGT CAAGCTCTAA ATCGGGGGCT CCCTTTAGGG | 5300 |
| TTCCGATTTA GTGCTTTACG GCACCTCGAC CCCAAAAAAC TTGATTAGGG | 5350 |
| TGATGGTTCA CGTAGTGGGC CATCGCCCTG ATAGACGGTT TTTCGCCCTT | 5400 |
| TGACGTTGGA GTCCACGTTC TTTAATAGTG GACTCTTGTT CCAAACTGGA | 5450 |
| ACAACACTCA ACCCTATCTC GGTCTATTCT TTTGATTTAT AAGGGATTTT | 5500 |
| GCCGATTTCG GCCTATTGGT TAAAAAATGA GCTGATTTAA CAAAAATTTA | 5550 |
| ACGCGAATTT TAACAAAATA TTAACGTTTA CAATTTAAAT ATTTGCTTAT | 5600 |
| ACAATCTTCC TGTTTTTGGG GCTTTTCTGA TTATCAACCG GGGTACATAT | 5650 |
| GATTGACATG CTAGTTTTAC GATTACCGTT CATCGATTCT CTTGTTTGCT | 5700 |
| CCAGACTCTC AGGCAATGAC CTGATAGCCT TTGTAGAGAC CTCTCAAAAA | 5750 |
| TAGCTACCCT CTCCGGCATG AATTTATCAG CTAGAACGGT TGAATATCAT | 5800 |
| ATTGATGGTG ATTTGACTGT CTCCGGCCTT TCTCACCCGT TTGAATCTTT | 5850 |
| ACCTACACAT TACTCAGGCA TTGCATTTAA AATATATGAG GGTTCTAAAA | 5900 |
| ATTTTTATCC TTGCGTTGAA ATAAAGGCTT CTCCCGCAAA AGTATTACAG | 5950 |
| GGTCATAATG TTTTTGGTAC AACCGATTTA GCTTTATGCT CTGAGGCTTT | 6000 |
| ATTGCTTAAT TTTGCTAATT CTTTGCCTTG CCTGTATGAT TTATTGGATG | 6050 |
| TTGGAANTTC CTGATGCGGT ATTTTCTCCT TACGCATCTG TGCGGTATTT | 6100 |
| CACACCGCAT ATGGTGCACT CTCAGTACAA TCTGCTCTGA TGCCGCATAG | 6150 |
| TTAAGCCAGC CCCGACACCC GCCAACACCC GCTGACGCGC CCTGACGGGC | 6200 |
| TTGTCTGCTC CCGGCATCCG CTTACAGACA AGCTGTGACC GTCTCCGGGA | 6250 |
| GCTGCATGTG TCAGAGGTTT TCACCGTCAT CACCGAAACG CGCGAGACGA | 6300 |
| AAGGGCCTCG TGATACGCCT ATTTTTATAG GTTAATGTCA TGATAATAAT | 6350 |
| GGTTTCTTAG ACGTCAGGTG GCACTTTTCG GGGAAATGTG CGCGGAACCC | 6400 |
| CTATTTGTTT ATTTTTCTAA ATACATTCAA ATATGTATCC GCTCATGAGA | 6450 |
| CAATAACCCT GATAAATGCT TCAATAATAT TGAAAAAGGA AGAGTATGAG | 6500 |
| TATTCAACAT TTCCGTGTCG CCCTTATTCC CTTTTTTGCG GCATTTTGCC | 6550 |
| TTCCTGTTTT TGCTCACCCA GAAACGCTGG TGAAAGTAAA AGATGCTGAA | 6600 |
| GATCAGTTGG GTGCACGAGT GGGTTACATC GAACTGGATC TCAACAGCGG | 6650 |
| TAAGATCCTT GAGAGTTTTC GCCCCGAAGA ACGTTTTCCA ATGATGAGCA | 6700 |
| CTTTTAAAGT TCTGCTATGT GGCGCGGTAT TATCCCGTAT TGACGCCGGG | 6750 |

```
CAAGAGCAAC TCGGTCGCCG CATACACTAT TCTCAGAATG ACTTGGTTGA           6800

GTACTCACCA GTCACAGAAA AGCATCTTAC GGATGGCATG ACAGTAAGAG           6850

AATTATGCAG TGCTGCCATA ACCATGAGTG ATAACACTGC GGCCAACTTA           6900

CTTCTGACAA CGATCGGAGG ACCGAAGGAG CTAACCGCTT TTTTGCACAA           6950

CATGGGGGAT CATGTAACTC GCCTTGATCG TTGGGAACCG GAGCTGAATG           7000

AAGCCATACC AAACGACGAG CGTGACACCA CGATGCCTGT AGCAATGGCA           7050

ACAACGTTGC GCAAACTATT AACTGGCGAA CTACTTACTC TAGCTTCCCG           7100

GCAACAATTA ATAGACTGGA TGGAGGCGGA TAAAGTTGCA GGACCACTTC           7150

TGCGCTCGGC CCTTCCGGCT GGCTGGTTTA TTGCTGATAA ATCTGGAGCC           7200

GGTGAGCGTG GGTCTCGCGG TATCATTGCA GCACTGGGGC CAGATGGTAA           7250

GCCCTCCCGT ATCGTAGTTA TCTACACGAC GGGGAGTCAG GCAACTATGG           7300

ATGAACGAAA TAGACAGATC GCTGAGATAG GTGCCTCACT GATTAAGCAT           7350

TGGTAACTGT CAGACCAAGT TTACTCATAT ATACTTTAGA TTGATTTAAA           7400

ACTTCATTTT TAATTTAAAA GGATCTAGGT GAAGATCCTT TTTGATAATC           7450

TCATGACCAA AATCCCTTAA CGTGAGTTTT CGTTCCACTG AGCGTCAGAC           7500

CCCGTAGAAA AGATCAAAGG ATCTTCTTGA GATCCTTTTT TTCTGCGCGT           7550

AATCTGCTGC TTGCAAACAA AAAAACCACC GCTACCAGCG GTGGTTTGTT           7600

TGCCGGATCA AGAGCTACCA ACTCTTTTTC CGAAGGTAAC TGGCTTCAGC           7650

AGAGCGCAGA TACCAAATAC TGTCCTTCTA GTGTAGCCGT AGTTAGGCCA           7700

CCACTTCAAG AACTCTGTAG CACCGCCTAC ATACCTCGCT CTGCTAATCC           7750

TGTTACCAGT GGCTGCTGCC AGTGGCGATA AGTCGTGTCT TACCGGGTTG           7800

GACTCAAGAC GATAGTTACC GGATAAGGCG CAGCGGTCGG GCTGAACGGG           7850

GGGTTCGTGC ACACAGCCCA GCTTGGAGCG AACGACCTAC ACCGAACTGA           7900

GATACCTACA GCGTGAGCTA TGAGAAAGCG CCACGCTTCC CGAAGGGAGA           7950

AAGGCGGACA GGTATCCGGT AAGCGGCAGG GTCGGAACAG GAGAGCGCAC           8000

GAGGGAGCTT CCAGGGGGAA ACGCCTGGTA TCTTTATAGT CCTGTCGGGT           8050

TTCGCCACCT CTGACTTGAG CGTCGATTTT TGTGATGCTC GTCAGGGGGG           8100

CGGAGCCTAT GGAAAAACGC CAGCAACGCG GCCTTTTTAC GGTTCCTGGC           8150

CTTTTGCTGG CCTTTTGCTC ACATGTTCTT TCCTGCGTTA TCCCCTGATT           8200

CTGTGGATAA CCGTATTACC GCCTTTGAGT GAGCTGATAC CGCTCGCCGC           8250

AGCCGAACGA CCGAGCGCAG CGAGTCAGTG AGCGAGGAAG CGGAAGAGC            8299
```

RECOMBINANT ADENOVIRUS AND ADENO-ASSOCIATED VIRUS, CELL LINES, AND METHODS OF PRODUCTION AND USE THEREOF

CROSS-REFERENCE TO RELATED APPLICATIONS

This application is a national phase filing, pursuant to 35 USC §371, of PCT/US96/10245, filed Jun. 4, 1996, which is a C-I-P U.S. patent application No. 08/549,489, filed Oct. 27, 1995, which is a C-I-P U.S. patent application No. 08/462,014, filed Jun. 5, 1995, now U.S. Pat. No. 5,756,283.
+gi This invention was supported by the National Institute of Health Grant Nos. HD32649-01, DK47757 and DK49136. The United States government has rights in this invention.

FIELD OF THE INVENTION

The present invention relates generally to the field of somatic gene therapy, and specifically to methods and compositions useful in the treatment of genetic disorders.

BACKGROUND OF THE INVENTION

Adenoviruses are eukaryotic DNA viruses that can be modified to efficiently deliver a therapeutic or reporter transgene to a variety of cell types [see, e.g., M. S. Horwitz et al, "Adenoviridae and Their Replication", *Virology*, second edition, pp. 1712, ed. B. N. Fields et al, Raven Press Ltd., New York (1990)]. Recombinant adenoviruses (rAds) are capable of providing extremely high levels of transgene delivery to virtually all cell types, regardless of the mitotic state. The efficacy of this system in delivering a therapeutic transgene in vivo that complements a genetic imbalance has been demonstrated in animal models of various disorders [K. F. Kozarsky et al, *Somatic Cell Mol. Genet.*, 19:449–458 (1993) ("Kozarsky et al I"); K. F. Kozarsky et al, *J. Biol. Chem.*, 269:13695–13702 (1994) ("Kozarsky et al II) and others]. The use of recombinant adenoviruses in the transduction of genes into hepatocytes in vivo has previously been demonstrated in rodents and rabbits [see, e.g., Kozarsky II, cited above, and S. Ishibashi et al, *J. Clin. Invest.*, 92:883–893 (1993)].

The first-generation recombinant, replication-deficient adenoviruses which have been developed for gene therapy contain deletions of the entire E1a and part of the E1b regions. This replication-defective virus is grown on an adenovirus-transforned, complementation human embryonic kidney cell line containing a functional adenovirus E1a gene which provides a transacting E1a protein, the 293 cell [ATCC CRL1573]. E1-deleted viruses are capable of replicating and producing infectious virus in the 293 cells, which provide E1a and E1b region gene products in trans. The resulting virus is capable of infecting many cell types and can express the introduced gene (providing it carries its own promoter), but cannot replicate in a cell that does not carry the E1 region DNA unless the cell is infected at a very high multiplicity of infection.

Adeno-associated virus (AAV) in an integrating human DNA parvovirus which has been proposed for use as a gene delivery vehicle for somatic gene therapy [B. J. Carter, in "Handbook of Parvoviruses", ed., P. Tijsser, CRC Press, pp.155–168 (1990)]. This small non-enveloped virus contains a 4.6 kb single stranded (ss) DNA genome that encodes sets of regulatory and capsid genes called rep and cap. Rep polypeptides (rep78, rep68, rep62 and rep40) are involved in replication, rescue and integration of the AAV genome. The cap proteins (VP1, VP2 and VP3) form the virion capsid. Flanking the rep and cap open reading frames at the 5' and 3' ends are 145 bp inverted terminal repeats (ITRs), the first 125 bp of which are capable of forming Y- or T-shaped duplex structures.

Recombinant forms of AAV (rAAV) have been developed as vectors by replacing all viral open reading frames with a therapeutic minigene, while retaining the necessary cis elements contained in the ITRs. [See, e.g., U.S. Pat. Nos. 4,797,368; 5,153,414; 5,139,941; 5,252,479; and 5,354,678; and International Publication Nos. WO 91/18088 published Nov. 28, 1991; WO 93/24641 published Dec. 9, 1993 and W094/13788 published Jun. 23, 1994]. However, progress towards establishing AAV as a transducing vehicle for gene therapy has been slow for a variety of reasons. For example, the integrated provirus preferentially targets specific sites in chromosome 19. Additionally, difficulties surround large-scale production of replication defective recombinants. The cells employed to produce rAAV must also be infected with adenovirus or herpesvirus to provide the necessary helper functions, thereby producing problems in purifying recombinant AAV (rAAV) from contaminating virus in culture. Practical experience with purified recombinant AAV as a gene therapy vector has been disappointing, because the more purified the AAV is from co-infection with its helper virus in culture, the lower the gene transduction efficiencies that the rAAV displays.

There remains a need in the art for additional recombinant adenoviruses and rAAV, therapeutic compositions and methods which enable effective use of these recombinant viruses in the treatment of disorders and diseases by gene therapy.

SUMMARY OF THE INVENTION

In one aspect of this invention, a packaging cell line is provided which expresses adenovirus genes E1a, E1b and E4, or functional fragments thereof, e.g., the E4 open reading frame (ORF) 6.

In another aspect, the invention provides a rAd comprising the DNA of at least a portion of the genome of an adenovirus having functional deletions of the E1 and E4 gene regions; a suitable gene operatively linked to regulatory sequences directing its expression, and an adenovirus capsid, the rAd capable of infecting a mammalian cell and expressing the gene product in the cell in vivo or in vitro. The invention also provides a mammalian cell infected with the rAd described above.

In still another aspect, the invention provides a rAd shuttle vector comprising the DNA of at least a portion of the genome of an adenovirus having functional deletions of the E1 and E4 gene regions.

In a further aspect, the invention provides a method for producing the above-described recombinant Ad and a method for delivering a selected gene into a mammalian cell using the recombinant Ad described above.

In another aspect, the invention provides a method for enhancing the efficiency of transduction of a recombinant AAV into a target cell. The method operates, in brief, by infecting a target cell with a ss recombinant adeno-associated virus (rAAV) which comprises a transgene operatively linked to regulatory sequences directing its expression, and contacting the infected cells with an agent which facilitates the conversion of ss rAAV to its double stranded (ds) form. Conversion of ss rAAV to ds rAAV occurs in the target cell, resulting in enhanced transduction of the rAAV into the target cell. The agent may be a helper virus which carries a selected gene or functional fragment thereof encoding a polypeptide capable of enhancing the conversion of the ss rAAV to ds rAAV and which is co-infected into the same target cell. The agent may also be a drug or chemical composition which accomplishes the same function and is applied to the infected target cell. This method can operate both in an ex vivo setting and in vivo.

In yet another aspect, the invention provides a novel recombinant AAV, which contains both the transgene intended for use in treating a genetic disease or disorder and at least one additional gene operatively linked to inducible or constitutive regulatory sequences. The additional gene(s) encodes a polypeptide capable of facilitating, alone or in concert with other additional genes, the conversion of ss rAAV to its ds form upon expression. In a preferred embodiment, the additional gene is adenovirus E4 or a functional fragment thereof. Also disclosed is a method for enhancing the efficiency of transduction of the novel rAAV into a target cell.

The novel rAAV and methods of this invention are also useful in pharmaceutical compositions for use in ex vivo and in vivo gene therapy treatment protocols for treating inherited diseases, cancer, and other genetic dysfunctions.

Other aspects and advantages of the present invention are described further in the following detailed description of the preferred embodiments thereof.

DETAILED DESCRIPTION OF THE INVENTION

Figure 1:
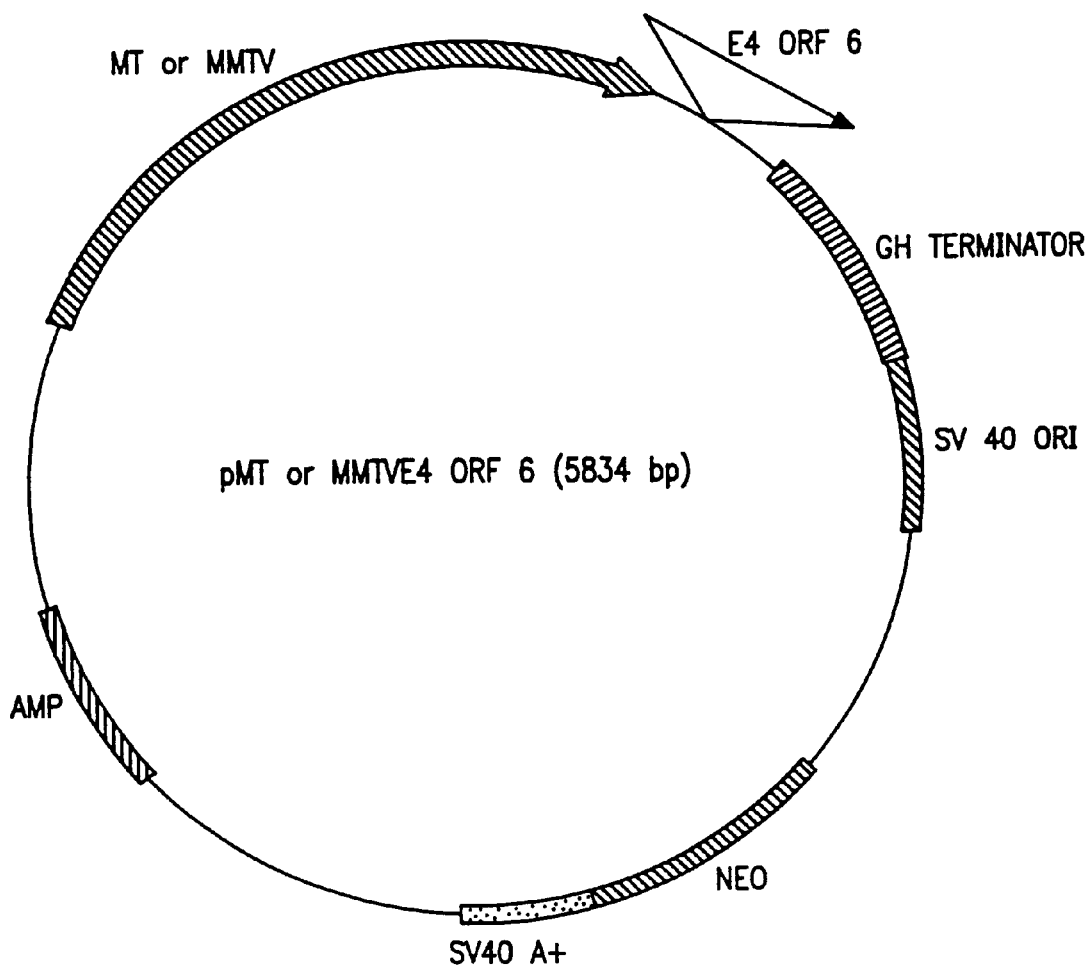
FIG. 1 is a schematic drawing of an exemplary plasmid pMMTVE4ORF6 [SEQ ID NO: 1] or pMTE4ORF6, which contains an MMTV or sheep MT promoter, respectively, in control of a human E4 ORF 6 gene sequence, a growth hormone gene terminator sequence (GH), an SV40 ori, pBR322-based plasmid sequences including a neo$^R$ gene, an SV40 polyA site and amp$^R$ gene.

The present invention provides packaging cell lines, which enable the production of recombinant adenoviruses (rAd) functionally deleted in both the E1 and E4 genes. These rAd and methods which enable the therapeutic treatment of disorders with such rAds are disclosed. Novel "second generation" recombinant adeno-associated virus (rAAV) and methods for enhancing the transduction efficiency of rAAV containing a transgene for expression in a somatic gene therapy protocol are also provided. The methods and compositions of this invention are useful in ex vivo applications of gene therapy, such as in the transduction of bone marrow cells with desirable hematopoietic stem cell progenitor genes prior to bone marrow transplantation. The embodiments of the invention are also useful in pharmaceutical compositions for direct in vivo treatment of patients by gene therapy vectors, including the transduction of desirable genes in patients with genetic disorders, such as cystic fibrosis (CF).

I. Packaging Cell Lines

To increase the transgene capacity and decrease immune response of rAds, as many viral genes as possible should be deleted to inactivate the adenovirus. However, it is crucial to generate complementing cell lines for construction and propagation of such deleted Ad. The method and compositions of the present invention overcome several problems previously identified in the gene therapy for first generation E1 deleted adenoviruses and display advantages in administration particularly to muscle tissue.

Early region 4 (E4) of Ad serotype 5 consists of 7 ORFs believed to be involved in viral DNA replication, host cell shut-off, and late mRNA accumulation. To generate rAd deleted in E4, the function of the E4 region must be supplied to the rAd by a helper virus or packaging cell line. However, useful packaging cell lines have not been available previously because normally the continuous expression of functioning Ad E1 and functional E4 in a single cell line are toxic to the cell. Such cells are therefore not useful for the growth and replication of rAds. Further, the DNA encoding the functional Ad E1 and Ad E4 genes, when present in a packaging cell line, can increase the chances of recombination with a rAd virus to cause the virus to revert to a wildtype Ad virus.

The present invention avoids these problems by providing a packaging cell line which contains the Ad5 E1 gene and only the ORF 6 of the Ad5 E4 gene. ORF6 of E4 alone can provide the requirements for E4 in the viral life cycle.

According to this invention, the ORF6 is preferably under the transcriptional control of an inducible promoter. The mouse mammary tumor virus (MMTV) promoter, inducible by a glucocorticoid, particularly, dexamethasone, is presently preferred. The DNA sequence of the MMTV promoter spans nucleotides 1-1506 of SEQ ID NO: 1. Another inducible promoter is the sheep metallothionine (MT) promoter, inducible by zinc [M. G. Peterson et al, Eur. J. Biochem., 174:417–424 (1988)]. However, the zinc sulfate inducer of the MT promoter can itself be toxic to the cells. Other inducible promoters, such as those identified in International patent application WO95/13392, published May 18, 1995, and incorporated by reference herein may also be used in the production of packaging cell lines according to this invention. Constitutive promoters, such as the constitutive Ad5 E4 region promoter, LTR, may be employed in control of the expression of ORF6.

The packaging cell line of the invention which utilizes an inducible promoter permits one to control the development of toxicity by regulating the expression of the E4 ORF6 gene. After the desired shuttle vector containing the Ad sequences is transfected into the cell line, expression of the E4 ORF6 can be induced by the appropriate inducer. The packaging cell is thus able to provide both Ad E1 and Ad E4 ORF6 gene products to the rAd for a sufficient period to allow productive infection and recovery of the rAd, before the cell becomes toxic. At present, the time period before the cell experiences toxicity is about 10 days.

In its most preferred form, the packaging cell line is a human embryonic kidney (HERK) 293 E1 expressing cell line into which is introduced the E4 ORF 6 sequence under the control of the inducible promoter. It should be understood by one of skill in the art that another parent cell line may be selected for the generation of a novel cell line expressing the E1a, E1b, and E4 ORF6 genes of a selected adenovirus serotype. Among such parent cell lines may be included HeLa [CCL 2], A549 [CCL 185], KB [CCL 17], Detroit [e.g., Detroit 510, CCL 72] and WI-38 [ATCC CCL 75] calls. These cell lines are all available from the American Type Culture Collection, 12301 Parklawn Drive, Rockville, Md., USA. Other suitable parent call lines may be obtained from other sources. If such parent cell lines were selected for modification, the cell line would need to be further supplied with the E1a and E1b gene functions, e.g., such as by transfection with a plasmid containing these genes or functional fragments thereof under a suitable promoter, as well as with the ORF6 gene as described herein.

Example 1 teaches construction of packaging cell lines containing only the ORF 6 of Ad5 E4 region or, for functional comparisons, the entire E4 region. Briefly described, the entire E4 region and an ORF6 sequence of Ad 5 E4 gene were obtained by known techniques [see, e.g., Sambrook et al., "Molecular Cloning. A Laboratory Manual.", 2d edit., Cold Spring Harbor Laboratory, New York (1989) and references cited therein]. To isolate the ORF6 region, the anchored PCR technique was used to amplify the ORF6 sequence from its initiation codon to its termination codon. Primers selected from the published sequence of ORF6 were used to amplify the ORF sequence and insert restriction sites onto the end of the sequence. The E4 ORF6 sequence itself is reproduced as nucleotides 1523 through 2408 of SEQ ID NO: 1. The entire E4 gene sequence is published in the Genbank sequence of Ad5 [Genbank Accession No. M73260].

A minigene was constructed that placed the ORF6 sequence under the control of a selected promoter. By "minigene" as used here is meant the combination of the desired sequence to be expressed (in this particular instance, the ORF6 sequence) and the other regulatory elements necessary to transcribe the desired sequence and express the gene product in a cell containing that minigene. The ORF6 sequence gene is operatively linked to regulatory components in a manner which permits its transcription. Such components include conventional regulatory elements, such as a promoter to drive ORF6 expression. One inducible promoter was the $Zn^{+2}$ inducible MT promoter; the other was the dexamethasone-inducible MMTV promoter of SEQ ID NO: 1.

The minigene also contains nucleic acid sequences heterologous to the ORF6 viral sequence, including sequences providing signals required for efficient polyadenylation of the transcript (poly-A or pA). A common poly-A sequence which is employed in this invention is that derived from the growth hormone (GH) gene terminator sequence (nuc. 2409–3654 of SEQ ID NO: 1). The poly-A sequence generally is inserted in the minigene following the ORF6 sequence. The polyA sequence employed in the MMTV-ORF6 minigene described in Example 1 [SEQ ID NO: 1] is supplied by the GH gene terminator and an SV40 origin of replication (ori). A similar minigene differing in promoter sequence, polyA sequence and/or SV40 ori can also be designed by one of skill in the art to transfer the E4 ORF6 sequence to a shuttle plasmid. Selection of these and other common vector elements are conventional [see, e.g., Sambrook et al, cited above, and references cited therein] and many such sequences are available from commercial and industrial sources as well as from Genbank.

The ORF6-containing minigene was subcloned into a pBR322-based shuttle plasmid that contained a neomycin resistance gene, resulting in the shuttle vector of FIG. 1. Any of the many known bacterial shuttle vectors may be employed to carry the minigene, providing that the vector contains a reporter gene or selectable marker of which many, e.g., neo, amp or puromycin, are known in the art. It is expected that one of skill in the art can develop other suitable shuttle vectors using other plasmid components which are similarly capable of transferring the ORF6 minigene into the chromosome of a cell transfected with the plasmid.

As further described in Example 1, other shuttle vectors were designed for comparative purposes, which contain the complete or substantially complete Ad5 E4 region under the control of the constitutive retroviral MLV LTR sequence in the presence or absence of the endogenous E4 promoter. The shuttle plasmid carrying the ORF6 minigene (or the entire E4 region) was introduced into HEK 293 cells which express the Ad E1 gene products. Complementing cell lines were generated that express these Ad E4 or ORF6 genes from either their endogenous promoters or heterologous inducible promoters. These cell lines are further characterized by their genetic constitution, E4 protein synthesis, recombinant AAV helper function, relative plaque efficiency of H5dl1004 virus, and growth kinetics of recombinant E1/E4 deleted adenovirus. These characteristics of exemplary E1/E4 expressing packaging cell lines are discussed in detail in the following examples.

II. Recombinant Adenovirus

The E1/E4 expressing cell line is useful in constructing E1/E4 deleted rAds which can deliver a suitable gene to mammalian cells and tissues. These rAds are functionally deleted in at least the E1a, E1b and E4 Ad gene regions. By the term "functionally deleted" is meant that a sufficient amount of the gene region is removed or otherwise damaged, e.g., by mutation or modification, so that the gene region is no longer capable of producing the products of gene expression. If desired, the entire gene region may be removed. In in vivo experiments with the rAd grown in the packaging cell lines, the E1/E4 deleted rAd demonstrated utility particularly in transferring a transgene to a muscle cell.

The adenovirus sequences used in the construction of the shuttle vectors, helper viruses, if needed, and rAd, and other components and sequences employed in the construction of the vectors and viruses described herein may be readily obtained from commercial or academic sources based on previously published and described sequences. Viral materials may also be obtained from an individual patient. The viral sequences and vector components may be generated by resort to the teachings and references contained herein, coupled with standard recombinant molecular cloning techniques known and practiced by those skilled in the art. Modifications of existing nucleic acid sequences forming the vectors, including sequence deletions, insertions, and other mutations taught by this specification may be generated using standard techniques. Similarly, the methods employed for the selection of viral sequences useful in a vector, the cloning and construction of the "minigene" and its insertion into a desired viral shuttle vector and the production of a recombinant infectious virus are within the skill in the art given the teachings provided herein.

A. Construction of the Transgene

A "minigene" in this context is defined as above, except that the components of this minigene are designed to express the gene product ex vivo or in vivo. Such components include conventional regulatory elements necessary to drive expression of the transgene in a cell transfected with the rAd. For this minigene, a selected promoter is operatively linked to the transgene and located, with other regulatory elements, within the selected viral sequences of the recombinant vector. Selection of the promoter is a routine matter and is not a limitation of this invention. Useful promoters may be constitutive promoters or regulated (inducible) promoters, which will enable control of the amount of the transgene to be expressed. For example, a desirable promoter is that of the cytonegalovirus (CMV) immediate early promoter/enhancer [see, e.g., Boshart et al, *Cell*, 41:521–530 (1985)]. Another desirable promoter includes the Rous sarcoma virus LTR promoter/enhancer. Still another promoter/enhancer sequence is the chicken cytoplasmic β-actin (CB) promoter [T. A. Kost et al, *Nucl. Acids Res.*, 11(23):8287 (1983)]. Other suitable promoters may be selected by one of skill in the art.

The minigene may also desirably contain nucleic acid sequences heterologous to the viral vector sequences including poly-A sequences and introns with functional splice donor and acceptor sites, as described above. The poly-A sequence generally is inserted in the minigene following the transgene sequences and before the 3' adenovirus sequences. A minigene of the present invention may also contain an intron, desirably located between the promoter/enhancer sequence and the transgene. Selection of these and other common vector elements are conventional as described above and many such sequences are available from commercial and industrial sources as well as from Genbank.

As above stated, the minigene is located in the site of any selected deletion in the rAd. In the E1/E4 deleted rAd H5.001CBLacZ, the transgene is located in the deleted E1 gene region. However, the transgene may be located elsewhere in the adenovirus sequence, as desired.

B. Production of Recombinant Adenovirus

Adenovirus sequences useful in this invention may include the DNA sequences of a number of adenovirus types, which are available from Genbank, including type Ad5 [Genbank Accession No. M73260]. The adenovirus sequences may be obtained from any known adenovirus serotype, such as serotypes 2, 3, 4, 7, 12 and 40, and further including any of the presently identified 41 human types

[see, e.g., Horwitz, cited above]. Similarly adenoviruses known to infect other animals may also be employed in the vector constructs of this invention. The selection of the adenovirus type is not anticipated to limit the following invention. A variety of adenovirus strains are available from the American Type Culture Collection, Rockville, Md., or available by request from a variety of commercial and institutional sources. In the following exemplary embodiment an adenovirus, type 5 (Ad5) is used for convenience.

However, it is desirable to obtain a variety of adenovirus shuttle vectors based on different human adenovirus serotypes. It is anticipated that a library of such plasmids and the resulting rAds would be useful in a therapeutic regimen to evade cellular, and possibly humoral, immunity, and lengthen the duration of transgene expression, as well as improve the success of repeat therapeutic treatments. Additionally the use of various serotypes is believed to produce rAds with different tissue targeting specificities. Additionally, the absence of adenoviral genes E1 and E4 in the rAd of this invention should reduce or eliminate adverse CTL responses which normally cause destruction of rAds deleted of only the E1 gene.

rAds of this invention are recombinant, defective adenoviruses (i.e., E1 deleted) which are also deleted completely or functionally of the E4 gene region. Functional deletions of E4 gene regions may be assessed by assays of Examples 2 and 3, among other assays. rAds useful in this invention may optionally bear other mutations, e.g., temperature sensitive (ts) mutations in the E2a gene region, and deletions in the E3 gene regions.

An adenovirus of this invention contains a functional deletion of the adenoviral early immediate early gene E1a (which spans mu 1.3 to 4.5) and delayed early gene E1b (which spans mu 4.6 to 11.2). Similarly the adenovirus has a functional deletion of the whole E4 region (which spans mu 92 to 97.2), or of at least ORF6 of the E4 region. Gene regions which may be optionally deleted in the E1/E4 deleted rAd of this invention include all or a portion of the adenovirus delayed early gene E3 (which spans Mu 76.6 to 86.2). The function of E3 is irrelevant to the function and production of the rAd.

The rAd of this invention may also have a mutation which results in reduced expression of adenoviral protein and/or reduced viral replication. For example, a ts mutation may be introduced into the adenovirus delayed early gene E2a (which spans mu 67.9 to 61.5). Among such mutations include the incorporation of the missense ts mutation in the (DBP)E2a region found in the Ad5 H5ts125 strain [P. Vander Vliet et al, *J. Virol.*, 15:348–354 (1975)] at 62.5 mu. A single amino acid substitution (62.5 mu) at the carboxy end of the 72 kd protein produced from the E2a gene in this strain produces a protein product which is a ss DNA binding protein and is involved in the replication of adenoviral genomic DNA. At permissive temperatures (approximately 32° C.) the ts strain is capable of full life cycle growth on HeLa cells, while at non-permissive temperatures (approximately 38° C.) no replication of adenoviral DNA is seen. In addition, at non-permissive temperatures, decreased immunoreactive 72 kd protein is seen in HeLa cells. See, e.g., J. F. Engelhardt et al, *Hum. Gene Ther.*, 5:1217–1229 (1994); J. F. Engelhardt et al, *Proc. Natl. Acad. Sci., USA*, 91:6196–6200 (1994) and International patent application WO95/13392, published May 18, 1995, incorporated by reference herein.

However, it should be understood that other deletions in the adenovirus genome as previously described in the art or otherwise may also occur in the rAds of this invention. One minimal type of rAd can contain adenovirus genomic sequences from which all viral genes are deleted. More specifically, the adenovirus sequences may be only the cis-acting 5' and 3' inverted terminal repeat (ITR) sequences of an adenovirus (which function as oris) and the native 5' packaging/enhancer domain, that contains sequences necessary for packaging linear Ad genomes and enhancer elements for the E1 promoter. The adenovirus 5' sequence containing the 5' ITR and packaging/enhancer region (Ad5 mu 0–1 or bp 1–360) can be employed as the 51 adenovirus sequence in rAd of this invention. The 3' adenovirus sequences including the right terminal (3') ITR sequence of the adenoviral genome spanning about bp 35,353—end of the adenovirus genome, or map units ⁻98.4–100 may be desirably employed as the 3' sequence of the rAd. These sequences, which are clearly devoid of the E1 and E4 genes, can flank, or be operatively associated with the minigene in a rAd. Any other necessary Ad gene products will then be supplied by helper viruses and the E1/E4 ORF6 expressing packaging cell of this invention.

Exemplary rAds for use in this invention, for example, may be obtained by homologous recombination of desired fragments from various rAds, a technique which has been commonly employed to generate other rAds for gene therapy use. In the examples below, a representative rAd, H5.001CBLacZ, is constructed by homologous recombination between the adenovirus dl1004 (also H5dl1004) viral backbone and pAdCBLacZ minigene DNA. HSdl1004 is an Ad5 virus deleted of from about map unit 92.1 through map unit 98, i.e. substantially the entire E4 gene. The dl1004 virus is described in Bridge and Ketner, *J. Virol.*, 632 (2):631–638 (February 1989).

The pAdCBLacZ vector is a cDNA plasmid containing Ad m.u. 0-1, an E1 deletion into which is inserted a bacterial β-galactosidase gene under the control of a chicken β-actin promoter, with other regulatory elements as described below, and flanked by Ad m.u. 9–16 and plassid sequence.

The production of the E1/E4 rAd of this invention in the packaging cell line of this invention utilizes conventional techniques. Such techniques include conventional cloning techniques of cDNA such as those described in texts [Sambrook et al, cited above], use of overlapping oligonucleotide sequences of the adenovirus genomes, PCR and any suitable method which provides the desired nucleotide sequence. Standard transfection and co-transfection techniques are employed, e.g., $CaPO_4$ transfaction techniques using the complementation 293 cell line. Other conventional methods employed include homologous recombination of the viral genomes, plaquing of viruses in agar overlay, methods of measuring signal generation, and the like.

For example, following the construction and assembly of the desired minigene-containing plasmid vector pAdCBLacZ, the E1/E4 expressing packaging cell line of this invention is infected with the helper virus H5dl1004. The infected cell line is then subsequently transfected with an adenovirus plasmid vector by conventional methods. Homologous recombination occurs between the E4-deleted H5dl1004 helper and the pAdCBLacZ vector, which permits the adenovirus-transgene sequences in the vector to be replicated and packaged into virion capsids, resulting in the rAd. About 30 or more hours post-transfection, the cells are harvested, an extract prepared and the rAd containing the LacZ transgene is purified by buoyant density ultracentrifugation in a CsCl gradient.

III. Use of the Recombinant Virus in Gene Therapy

The rAd containing the transgene produced by cooperation of the adenovirus vector and E4 deleted helper virus and packaging cell line, as described above, provides an efficient gene transfer vehicle which can deliver the transgene in a pharmaceutical composition to a patient in vivo or ex vivo and provide for integration of the gene into a mammalian cell.

The rAds are administered to humans in a conventional manner for gene therapy and serve as an alternative or supplemental gene therapy for the disorder to which the transgene is directed. A rAd of this invention may be administered to a patient, preferably suspended in a biologically compatible solution or pharmaceutically acceptable delivery vehicle. A suitable vehicle includes sterile saline. Other aqueous and non-aqueous isotonic sterile injection solutions and aqueous and non-aqueous sterile suspensions known to be pharmaceutically acceptable carriers and well known to those of skill in the art may be employed for this purpose.

The rAds are administered in sufficient amounts to transfect the desired target cells, e.g., muscle, liver, epithelial, etc. and provide sufficient levels of transfer and expression of the transgene to provide a therapeutic benefit without undue adverse or with medically acceptable physiological effects which can be determined by those skilled in the medical arts. Conventional and pharmaceutically acceptable routes of administration include direct delivery to the muscle or other selected cell, intranasal, intravenous, intramuscular, subcutaneous, intradermal, oral and other parental routes of administration. Routes of administration may be combined, if desired.

Dosages of rAd will depend primarily on factors such as the condition being treated, the age, weight and health of the patient, and may thus vary among patients. For example, a therapeutically effective human dose of the rAd is generally in the range of from about 20 to about 100 ml of saline solution containing concentrations of from about $1 \times 10^9$ to $1 \times 10^{11}$ pfu/ml virus. A preferred human dose is estimated to be about 50 ml saline solution at $2 \times 10^{10}$ pfu/ml. The dose will be adjusted to balance the therapeutic benefit against any side effects. The levels of expression of the transgene can be monitored to determine the frequency of administration.

An optional method step involves the co-administration to the patient, either concurrently with, or before or after administration of the rAd of a suitable amount of a short acting immune modulator. The selected immune modulator is defined herein as an agent capable of inhibiting the formation of neutralizing antibodies directed against the recombinant vector of this invention or capable of inhibiting or substantially delaying cytolytic T lymphocyte (CTL) elimination of the vector. Among desirable immune modulators are interleukin-12 [European Patent Application No. 441,900]; gamma interferon [S. C. Morris et al, *J. Immunol.*, 152:1047 (1994)]; interleukin-4 [U.S. Pat. No. 5,017,691]; antibody to the CD4 protein, such as anti-OKT 3+ [see, e.g., U.S. Pat. No. 4,658,019] or antibody GK1.5 (ATCC Accession No. TIB207); a soluble CD40 molecule or an antibody to CD40 ligand (Bristol-Myers Squibb Co) [European patent application 555,880, published Aug. 18, 1993]; a soluble form of B7 or an antibody to CD28 or CTLA4 [CTLA4-Ig (Bristol-Myers Squibb Co), European patent application 606,217, published Jul. 20, 1994], or agents such as cyclosporin A or cyclophosphamide. Thus, the pharmaceutical compositions and methods of this invention provide a desirable gene therapy treatment.

IV. Recombinant Adeno-Associated Virus

In the following context the term "transgene" means a nucleic acid sequence or reverse transcript thereof, heterologous to the AAV sequence, which encodes a polypeptide or protein of interest. The transgene may be operatively linked to regulatory components in a manner which permits transgene transcription, i.e., the transgene is placed into operative association with a promoter, as well as other regulatory sequences, such as SV40 introns or polyA sequences, useful for its regulation. The composite association of the tranagene with its regulatory sequences in referred to herein as a minicassette or minigene.

The composition of the transgene or minicassette sequence will depend upon the use to which the resulting rAAV will be put. For example, one type of transgene sequence includes a reporter sequence, which upon expression produces a detectable signal. Such reporter sequences include without limitation, an *E. coli* β-galactosidase (LacZ) cDNA, an alkaline phosphatase gene (ALP) and a green fluorescent protein gene. These sequences, when associated with regulatory elements which drive their expression, provide signals detectable by conventional means, e.g., ultraviolet wavelength absorbance, visible color change, etc.

Another type of transgene sequence includes a therapeutic gene which expresses a desired gene product in a host cell. These therapeutic nucleic acid sequences typically encode products for administration and expression in a patient In vivo or ex vivo to replace or correct an inherited or non-inherited genetic defect or treat an epigenetic disorder or disease. Such transgenes may be readily selected by one of skill in this art and the design of the transgene or the minicassette for insertion into the rAAV is not a limitation of this invention.

The term "rAAV" encompasses any recombinant AAV gene therapy vehicle of the prior art, including the AdAAV hybrid virus described in published International Patent Application No. W096/13598, published May 9, 1996. More specifically, rAAV defines a rAAV comprising: (a) the DNA of at least a portion of the genome of an AAV, which portion is capable of transducing into a target cell at least one selected gene in the absence of cell division; and (b) at least one selected gene (or transgene) operatively linked to regulatory sequences directing its expression, the gene flanked by the DNA of (a) and capable of expression in the target cell in vivo or in vitro.

Other rAAVs have been described in the art, The method of this invention is not limited by the precise nature of the AAV sequences used in the rAAV, provided that at a minimum both the 5' and 3' AAV inverted terminal repeats are present. Thus the rAAV may be selected by one of skill in the art, and is not itself a limitation on this invention. The rAAVS specifically disclosed herein are illustrative.

By the term "transduction" is meant that the rAAV produced by practice of the invention is capable of infecting a desired target cell and expressing the transgene in the cell by harnessing the cell's machinery. Transduction may include stably integrating the viral DNA into a chromosome of the target cell. "Enhanced transduction" is defined as the ability of the rAAV in the presence of a conversion agent to transduce the target cell, either in vitro, or vivo or in vivo, at an efficiency greater than a typical prior art rAAV produced in, and purified from, a culture co-infected with an adenovirus or herpesvirus helper.

This method is based on the observation that the limiting step in rAAV mediated transduction of cells for gene therapy is not the internalization or transfer of the ss viral genome, but rather the subsequent conversion of the single-stranded (ss) viral genome to a transcriptionally active double-stranded (ds) form. Formation of ds DNA intermediates is necessary for recombinant gene expression, which is likely to be modulated by viral and cellular factors through post-transcriptional mechanisms. The inventors have designed a method to overcoxe this rate-limiting step, thereby enhancing transduction ability of an rAAV and ultimately the use of rAAV in gene therapy protocols.

This method of the present invention may employ a conventionally prepared as rAAV containing a transgene. The prior art produces as rAAV by co-infection in culture with a helper adenovirus or herpesvirus, followed by purifying the rAAV from the culture contaminants including the helper virus, and infecting the target cell with the rAAV alone. The present invention provides for infecting a target cell with a ss rAAV. However, once the target cell is infected, the infected cell is contacted with an agent which facilitates the conversion of the ss rAAV to the ds form of rAAV. The action of this "facilitating agent" or "conversion agent" causes the ss to ds conversion to occur in the target cell, resulting in enhanced transduction of the recombinant AAV into the target cell. By facilitating the conversion of ss to ds rAAV in the target cell, the method of this invention may also result in both transduction and stable chromosomal integration of the rAAV into the chromosome of said host cell.

Preferably, for use of this invention the "facilitating or conversion agent" may take several forms.

A. The Conversion Agent Is a Helper Virus

In one embodiment, the agent is a helper virus and the method includes an additional step of co-infecting the target cell with the helper virus. The helper virus useful in this method contains a selected gene which can facilitate the conversion of ss rAAV to ds rAAV. The selected gene may encode a gene product or polypeptide (or a functional fragment of the polypeptide which shares the biological activity of the full-length polypeptide) which enhances the conversion. Alternatively, the selected gene may express an antisense or ribozyme which functions in the cell to block or inhibit a cellular gone that normally prevents as to ds conversion of the rAAV. These genes may also be employed in the second generation rAAV described below.

The helper virus is capable of expressing the selected gene product in the target cell in the absence of cell division. The helper virus may be a wild-type or mutant adenovirus. The helper virus may alternatively be a wild-type or mutant herpesvirus. Preferably, for use as facilitating agents, such viruses are mutants deleted of several normal genes so that the helper viruses and/or their expressed gene products will not cause disease in a patient.

For example, a helper adenovirus useful in this invention may express only a gene product of a single adenoviral early gene. Exposure of the ss rAAV to an Ad early gene product is sufficient to substantially enhance the formation of ds rAAV genome with a coordinate increase in transduction efficiency. The Ad early genes which are useful in producing this effect are E1, E2a, E4 and functional fragments thereof. However, as demonstrated by the examples below, adenovirus substantially enhances recombinant AAV transduction in vitro in a way that is dependent on expression of the E1 and E4 genes of adenovirus and is directly proportional to the appearance of ds replicative forms of rAAV.

One example of a helper virus is an adenovirus deleted of most of its wild-type early genes and which is capable of expressing only its E4 gene or a functional fragment thereof in the target cell. Among such functional fragments is the ORF 6 of the E4 gene. As described below in the examples, experiments in cell lines indicate that the ORF6 of the adenoviral E4 gene locus is sufficient to significantly enhance rAAV transduction. Selective expression of the E4-ORF6 product of adenovirus accomplishes an increase in transduction efficiency similar to, but somewhat attenuated, compared to that produced by exposure to the E1 and E4 gene products in combination. That is, the ORF6 product of E4 is sufficient to enhance the augmentation of rAAV transduction; but this effect is amplified substantially by E1 gene products.

Thus, more preferably, exposure of the rAAV to both the expressed E1 and E4 gene products produces a substantial enhancement of the above-described rate limiting step. Therefore, another exemplary helper virus may also contain more than one gene which, upon expression, facilitates the ss to ds conversion. An example of such a helper virus is an adenovirus which expresses both the E1 and E4 genes, or functional fragments thereof. Still other Ad genes may be expressed by the helper virus, provided that the virus is sufficiently crippled so that it does not cause disease in the patient contributing the target cells.

Where the agent which facilitates conversion of as to ds rAAV is a helper virus, the method of the invention comprises co-infecting the target cell with the rAAV and the helper virus. Such co-infection may occur in the context of ex vivo therapy, i.e., manipulations performed on cells extracted from the patient, which cells are reinserted into the patient after the method is performed. Alternatively, the patient may be directly co-infected with the two viruses by conventional means. Delivery of the two viruses to the patient may be directed to a specific organ, or to the general circulatory system. Such delivery methods are described in the art for gene therapy of, e.g., cystic fibrosis [see, e.g., U.S. Pat. No. 5,240,846].

B. The Conversion Agent Is a Chemical, Drug or Other Entity that Can Activate rAAV Transduction In another embodiment of the method of this invention, the conversion agent which contacts the cells infected with the rAAV may be selected from the following classes of known compounds or methods: 1) inhibitors of DNA synthesis such as hydroxyurea, hydrogen peroxide, and other direct or indirect inhibitors of DNA polymerase; 2) chemotherapeutic agents that induce DNA damage, such as cyclophosphamide, alkylating agents, purine analogs, e.g., 6-thioguanine, etc.; 3) drugs that interfere with DNA modifying enzymes, such as inhibitors of topoisomerase, DNA ligase exonucleases and endonucleases; and 4) agents that nonspecifically enhance transcription, such as sodium butyrate, or agents that stabilize cells, such as DMSO. Also, genotoxic agents such as carcinogens may be employed as the conversion agent. Other methods of inducing disruption or damage to DNA may also be useful as agents capable of facilitating ss to ds conversion of rAAV and maybe selected by one of skill in the art, including physical methods, such as irradiation. These classes of compounds or methods are believed to result in the conversion from ss to ds rAAV.

According to this embodiment of the method of the invention, the rAAV is again produced conventionally, but not co-infected with a helper virus. The ss rAAV is infected into the target cell, and the infected cell is contacted by the agent in an appropriate manner depending on the identity of the agent. These conversion enhancing agents can be employed in ex vivo treatment of the target cells infected by the rAAV by application directly to the cells. Such application can occur substantially simultaneously, or consecutively, with application of the rAAV gene therapy vehicle. For example, the infected target cell may be subjected to one of the above-listed compounds or drugs for a desired time period. The parameters for contacting the infected cells with the agent may readily be determined by one of skill in the art. These parameters will depend upon whether the method is performed ex vivo or in vivo. For example, the number of ex vivo infected cells to be treated will be considered for the dosage, and timing of such treatment.

Similarly, the physical status of the patient can determine the parameters of delivery of the agent to the patient in vivo. The dosage and amount of the damaging agent may therefore be adjusted by one of skill in the art. Where the agents are typical chemotherapeutic drugs approved for use in humans or animals, such enhanced conversion of rAAV may also occur in vivo by the co-administration of the agent, i.e., the chemotherapeutic drug, and the rAAV gene therapy vehicle to the patient. According to this aspect of the invention, the chemotherapeutic drug would be administered only when the rAAV is administered. Appropriate dosages and amounts of chemotherapeutic drugs and recombinant gene therapy vehicles and means for determining such amounts are within the skill of the art. However, because the effect of the chemotherapeutic drug will enhance the as to ds conversion of the rAAV and thus enhance its efficiency of transduction into the target cells, it is anticipated that lower dosages than the conventional dosages of either or both the drug and the rAAV could be effectively administered.

C. Conversion Agent May Be Part of the rAAV

In still another embodiment of this invention, a novel "second generation" rAAV may be designed to incorporate the conversion agent into the virus, so that both the transgene and the conversion agent are co-expressed in the target cell. Such a novel recombinant adeno-associated virus comprises the following components:

(a) the DNA of at least a portion of the genome of an adeno-associated virus which portion is capable of transducing at least two selected genes or functional fragments thereof into a target cell in the absence of cell division; (b) a first selected gene, i.e., the desired transgene, operatively linked to regulatory sequences directing its expression, and (c) a second selected gene, i.e., the "conversion gene" operatively linked to regulatory sequences capable of directing expression of said second gene. The "conversion gene" upon expression is capable of facilitating the conversion of the as rAAV to its ds form upon expression. The first and second genes in this rAAV are flanked by the AAV DNA, preferably the 5' and 3' ITRs. An embodiment of such a second generation rAAV is provided schematically in FIG. 11. Its DNA sequence is provided in SEQ ID NO: 5.

Another embodiment of such a novel rAAV may include more than one gene which upon expression has the ability to facilitate conversion of ss to ds rAAV in the target cell. For example, the novel rAAV described above may also contain an additional selected gene operatively linked to regulatory sequences capable of directing its expression, the additional gene and said second "conversion" gene described above being capable of jointly facilitating the conversion of ss rAAV to its ds form upon expression of both the second and additional genes. In this rAAV, all three genes, i.e., the transgene, the second "conversion" gene and the additional gene are flanked by the AAV DNA.

In one desirable embodiment of a novel rAAV, the AAV ITRs flank a selected transgene, and a conversion gene, which is the adenovirus E4 gene or a functional fragment thereof (e.g., the ORF6 sequence). In another embodiment, the novel recombinant expresses three genes, the transgene, the adenovirus E4 gene or a functional fragment thereof and the adenovirus E1 gene or a functional fragment thereof. The E4 and E1 gene products expressed in the target cell with the transgene, together act to facilitate conversion of the ss to ds form of rAAV.

In still another embodiment of the novel rAAV and its use, the regulatory sequences directing expression of the conversion gene, e.g., whether it be a single second gene or more than a single additional gene, may include an inducible promoter. Thus, expression of the conversion gene occurs only in the presence of an inducing agent. Many inducible promoters and companion inducing agents, e.g., steroids such as glucocorticoids, are known to the art and may be readily selected for incorporation into the rAAV and methods of this invention by one of skill in the art with resort to this description.

The method of the invention employing such "second generation" rAAVs which carry at least one "conversion gene" provides for infecting the target cell with this ss rAAV. Where the promoters directing expression of both the transgene and the conversion gene are constitutive, the infected target cell machinery will direct the expression of the transgene product and conversion gene product. Co-expression in the target cell of the transgene and the "conversion gene" facilitates the conversion of ss rAAV to ds rAAV in the cell, and increases the transduction efficiency, and perhaps stable chromosomal integration, without further method steps.

When the second generation rAAV employed in the method contains the "conversion gene(s)" under the control of inducible promoter(s), the method is slightly altered. Following infection of the target cell by the rAAV, the infected target cell is contacted with a suitable inducing agent, which triggers the inducible promoter to "turn on" production of the conversion gene product. When the inducing agent is removed or stopped, the expression of the conversion gene product is "turned off".

As described above, any prior art rAAV containing a transgene for gene therapy may be used in at least one embodiment of the above methods. The sources, selection and assembly of the various components to generate the rAAV, including the novel rAAV described above, are now conventional and readily accessible to one of skill in this art, given the disclosure contained herein. Such methods employ conventional genetic engineering techniques [See, e.g. Sambrook et al, cited above].

The novel rAAV viruses and the methods of this invention provide efficient gene transfer vehicles for somatic gene therapy and are suitable in pharmaceutical compositions for ex vivo applications and in vivo use. When rAAV contain a therapeutic gene, e.g., in place of the LacZ transgene illustrated in the exemplary rAAV, AV.CMVLacZ, by use of the rAAV and the methods described herein, the therapeutic transgene can be delivered to a patient in vivo or ex vivo to provide for efficient transduction, and possibly stable integration, of the desired gene into the target cell. Thus, these novel rAAV and the methods described herein can be employed to correct genetic deficiencies or defects. The potential of AAV to efficiently integrate its genome into nondividing cells is currently being exploited in the development of gene therapies based on ex vivo transduction of hematopoietic stem cells. In vivo application of rAAV is primarily being developed for the treatment of CF where purified stocks of virus are instilled into the airway to transduce the terminally differentiated epithelial cells of the conducting airway. The methods and compositions described herein can be used with both types of gene therapy. Another condition suitable for such use includes transduction of the low density lipoprotein (LDL) receptor gene into hepatocytes for the treatment of familial hypercholesterolemia. One of skill in the art can generate any number of rAAV which can be used via the above methods for the treatment of these and other disorders.

For ex vivo or for in vivo therapy, the rAAV may be used to infect the target cells by suspending the virus particles in a biologically compatible solution or pharmaceutically acceptable delivery vehicle. A suitable vehicle includes sterile saline. Other aqueous and non-aqueous isotonic sterile injection solutions and aqueous and non-aqueous sterile suspensions known to be pharmaceutically acceptable carriers and well known to those of skill in the art may be employed for this purpose.

The rAAVs are administered in sufficient amounts to transfect the desired cells and provide sufficient levels of expression of the selected transgene to provide a therapeutic benefit without undue adverse, or with medically acceptable, physiological effects which can be determined by those skilled in the medical arts. Conventional and pharmaceutically acceptable routes of in vivo administration include direct delivery to the target organ, tissue or site, intranasal, intravenous, intramuscular, subcutaneous, intradermal, oral and other parental routes of administration. Routes of administration may be combined, if desired.

Dosages of the rAAV for the infecting step of the method will depend primarily on factors such as the therapeutic environment, i.e., ex vivo or in vivo; the condition being treated, the selected gene, the age, weight and health of the patient, and may thus vary among patients. A therapeutically effective dosage of the rAAV for ex vivo treatment will be based upon the multiplicity of infection, which is likely to range from between about 1 to about 10 transducing particles/cell. A therapeutically effective human dosage of the rAAV for in vivo infection according to the present invention is believed to be in the range of from about 20 to about 50 ml of saline solution containing concentrations of from about $1 \times 10^7$ to $1 \times 10^{10}$ transducing viral particles/ml virus. A preferred human dosage is about 20 ml saline solution at the above concentrations. The dosage will be adjusted to balance the therapeutic benefit against any side effects. The levels of expression of the selected gene can be monitored to determine the selection, adjustment or frequency of dosage administration.

The effective amount of the facilitating agent to be administered is within the skill of the art to determine and will depend upon the identity of the agent. Known dosages of certain of the classes of chemicals and pharmaceuticals described above may be employed in this method to damage the DNA and facilitate ss to ds conversion of the rAAV. Where the agent is a gene expressed by a helper virus, the amounts of infecting virus should be similar to those amounts described above for the rAAV. Of course, where the agent is a gene present in a second generation rAAV, the identical dosages described above for the rAAV will apply.

Several embodiments of the above-described methods of this invention were confirmed in murine models of rAAV mediated gene transfer to both lung and liver. These experiments demonstrated similarly low levels of gene transfer In vivo by rAAV, which was increased several orders of magnitude by coinfection with E1 and E4 expressing adenovirus.

In summary, experiments were conducted to demonstrate that adenovirus enhances rAAV transduction in cultured cells. During the production and characterization of a lacZ recombinant AAV generated in 293 cells that were coinfected with an E1 deleted virus, it was observed that purification of rAAV from lysates was associated with substantial loss of lacZ transducing activity when assayed on 293 cells. This drop in rAAV activity was particularly evident in the final step where residual contaminating helper adenovirus was removed by heat inactivation. LacZ transducing activity was recovered by adding adenovirus back to the purified stock of rAAV. These data provided the first indication that adenovirus could substantially enhance the transduction efficiency of rAAV.

Figure 5A:
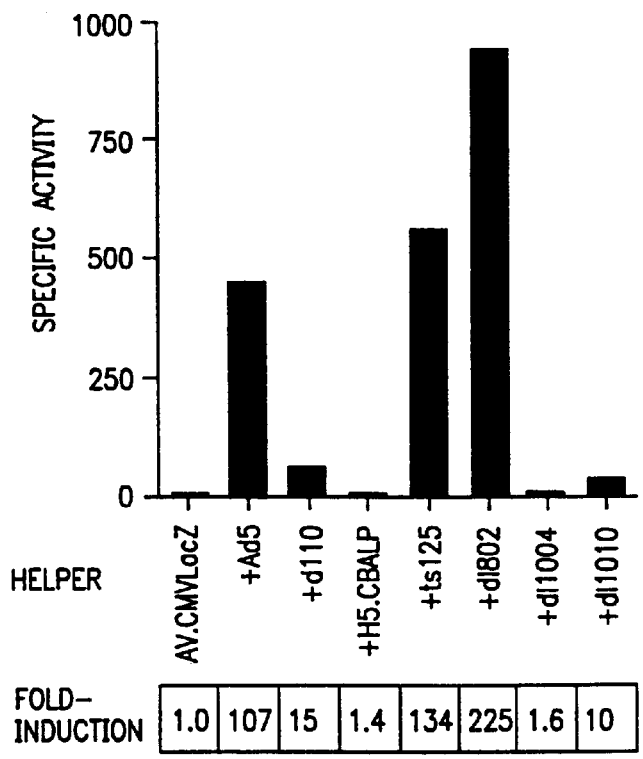
FIG. 5A is a bar graph plotting β-galactosidase enzyme activity in lysates from infected Hela cells. The horizontal axis indicates the adenoviruses infected into the HeLa cells, with the symbol "+" indicating the addition of the adenovirus to the rAAV, AV.CMVLaCZ. The vertical axis indicates intracellular β-galactosidase specific activity (mUnits/mg protein) using ONPG. Below each bar, the fold-induction in specific activity relative to cells that received the AV.CMVLacZ vector alone is given.

As described in Example 10, a series of complementation groups were generated by mixing different adenovirus early gene mutants with purified LacZ rAAV, referred to as AV.CMVLacZ (see Example 2). These defined mixtures of viruses were analyzed for LacZ transduction on Hela cells (See Examples 12 and 13). An E1 deletion rAd H5.CBALP and the E4 deletion mutant dl1004 provided no significant increase in AV.CMVLacZ transduction (FIG. 5A). However, partial activity could be achieved with E1 and E4 mutants that carried less severe deletions. Both dl110 (E1B-55 kDa deleted) and dl1010 (ORF6 deleted) enhanced transduction to levels that approached those of Ad5, ts125, and d1802 in terms of the number of positive blue cells, but total β-galactosidase activity was substantially lower (FIG. 5A). These results implicate early regions E1 and E4 in the augmentation of rAAV transduction.

The experiments described below also demonstrate that the novel rAAV which incorporates as its conversion gene, an Ad gene, such as E4, can increase transduction efficiency of the rAAV in the absence of a helper virus. As described in more detail in Example 15 below, 293 cells were stably transfected with a genomic fragment of Ad5 spanning E4. This E1/E4 expressing cell line and the parent E1 expressing cell line (293) were infected with rAAV and analyzed for transduction. These experiments demonstrated the significance of the combined expression of E1 and E4(ORF6) in the adenovirus mediated augmentation of rAAV transduction.

In the presence of E1 and E4 expression, rAAV transduction was invariably accompanied by the appearance of ds RF monomers and dimers (Example 14). Importantly, the tight correlation between rAAV vector transduction and the accumulation of duplex forms could be achieved in two different experimental settings; cells infected with E1/E4 expressing adenovirus (FIGS. 8A and 8B), or complementing cell lines (FIG. 8C).

The following examples illustrate the construction and testing of the novel packaging cell lines, the E1/E4 deleted rAd of the present invention and the use thereof, improved methods and second generation recombinant AAV production for gene therapy of the present invention. These examples are illustrative only, and do not limit the scope of the present invention.

Example 1

Novel E1a/E1b and E4 Expressina Packaging Cell Lines

A. Construction of E4 ORF 6 Expressing Plasmids

The entire E4 region from Ads or an ORF6 minigene were subcloned into a shuttle plasmid that contained a neomycin resistance gene. Two versions of ORP6 minigene were developed that differed in the promoter element. The first used a Zn+2 inducible sheep metallothionine (MT) promoter to drive ORF 6 expression. The second used a dexamethasone-inducible mouse mammary tumor virus (MMTV) promoter.

An exemplary plasmid useful for the construction of a packaging cell line of this invention is pMMTVE4ORF6. The minigene contained in this plasmid is set out in SEQ ID NO: 1, and contains a mouse mammary tumor virus promoter (MMTV) (nucleotides 1–1506 of SEQ ID NO:1) in transcriptional control of a human E4 ORF 6 gene sequence (nucleotides 1523–2408 of SEQ ID NO: 1), a growth hormone terminator (GH) (nucleotides 2409–3654 of SEQ ID NO: 1), an SV40 origin of replication, plasmid sequences from plasmid pBR322, including a neomycin resistance gene, and an ampicillin resistance gene. The amino acid sequence of ORF 6 is indicated in SEQ ID NO: 2. The various functional fragments of this plasmid may be readily replaced with other conventionally used sequences and are not critical to the design of the plasmid.

Another plasmid useful for the construction of a packaging cell line of this invention is pMTE40RF6. The DNA sequence of the minigene contained in this plasmid is similar to that of SEQ ID NO: 1, except that the promoter is a sheep metallothionine promoter (MT promoter) [M. G. Peterson et al, cited above].

A plasmid used as a control for the construction of a packaging cell line of this invention is pLTR.E4(−). This plasmid contains the endogenous constitutive retroviral MLV LTR and most of the Ad E4 gene region except that the endogenous E4 promoter and a portion of E4 ORF1 are missing. The other plasmid sequences remain the same as described above.

Still another plasmid useful for the study of the methods of this invention is pLTR.E4, which contains the constitutive MLV LTR and endogenous E4 promoter and an intact E4 gene. The other plasmid sequences remain the same as described above.

To determine whether ORF6 expression was sufficient to enhance rAAV transduction, the inducible metallothionein (MT)-0RF6 minigene was stably transfected into HeLa cells. This new cell line, HeLa(MT-ORF6) was evaluated for LacZ rAAV transduction in response to ORF6 induction as described below. The cell line 293 (MT-ORF6) expresses ORF-6 of the E4 gene of AdS from the metallothionine promoter which is relatively inactive at baseline but can be induced with divalent cations. These 293 cells were included to establish the baseline transduction efficiency.

B. Transfections and Selection of Clones

Each of the above-described plasmids was transfected by the calcium phosphate precipitation technique into the human embryonic kidney cell line 293 [ATCC CRL1573] which expresses the product of the adenovirus E1 genes, or into HeLa cells, seeded on 100 mm plates (10 µg plasaid/plate). Twenty four hours post-transfection, cells were harvested and seeded at varying dilutions (1:10–1:100) in 100 mm plates for about 10 days. Seeding media contain G418 (Geneticin, BRL) at 1 mg/ml. Resistant colonies that developed were selected using the following assays and expanded. Preliminary analysis of clones was based on enhanced transduction efficiency of a recombinant adeno-associated virus, AV.CMVLacZ, and immunofluorescence localization of Ad E4 protein as described in the following examples.

Example 2

Recombinant AAV and AV.CMBLaCZ Transduction Enhancement Assay

E1 and E4 Ad gene products are needed for recombinant adeno-associated virus (AAV) function. This primary assay involves seeding the packaging cell lines of Example 1 in 96 well 35 mm culture plates ($2 \times 10^6$ cells/well) and infecting the cells with purified, heat-treated AV.CMVLacZ at an MOI of 1000 virus particles/cell.

A. Preparation of Recombinant AV.CMVLacZ

Figure 10:
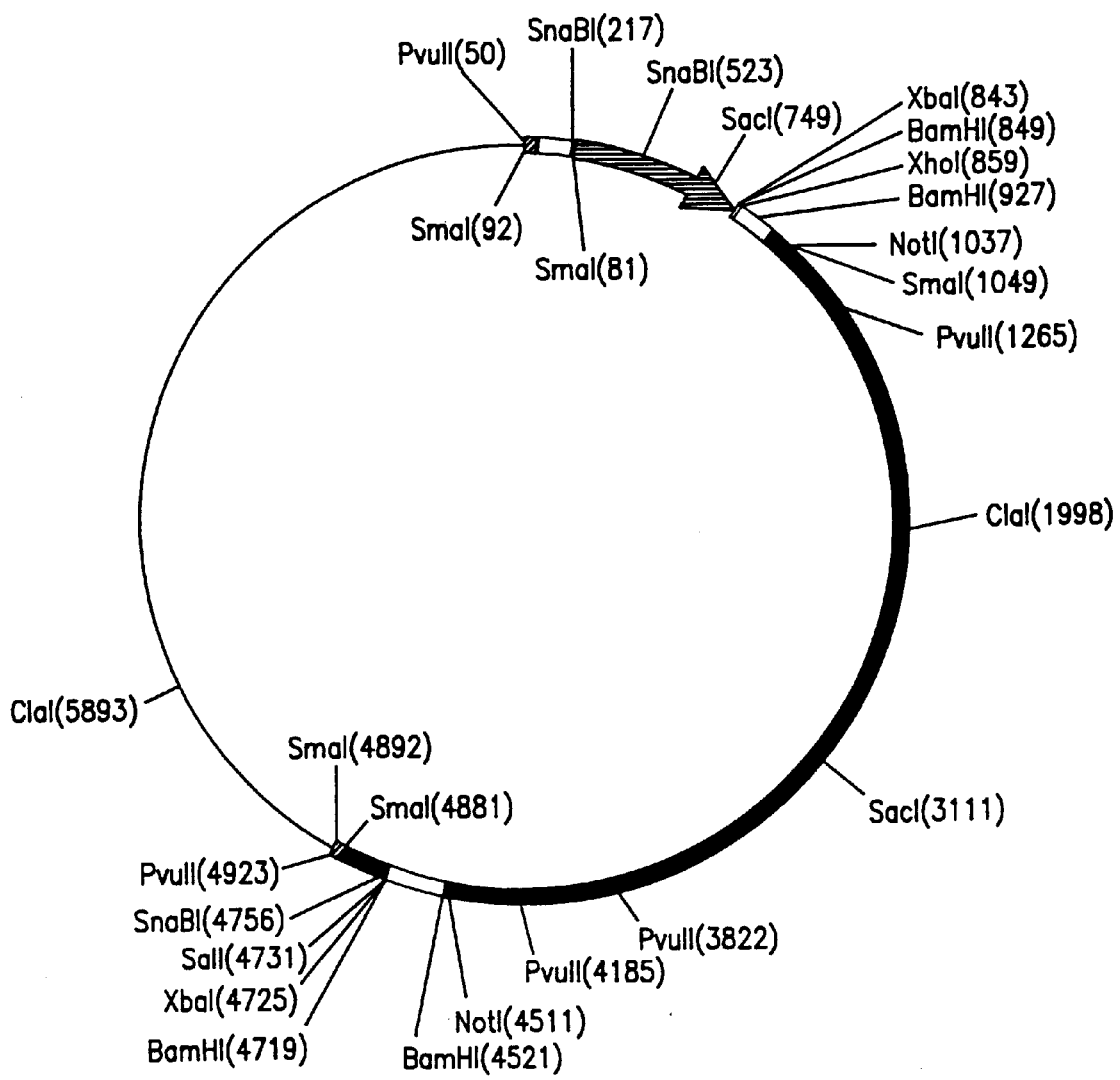
FIG. 10 is a schematic of the plasmid pAV.CMVLaCZ [SEQ ID NO: 4].

A recombinant AAV virus was prepared by conventional genetic engineering techniques for the purposes of this experiment. Recombinant AAV was generated by plasmid transfections in the presence of helper adenovirus [Samulski et al, *J. Virol.*, 63:3822–3828 (1989)]. A cis-acting plasmid pAV.CMVLacZ [SEQ ID NO: 4] (see FIG. 10) was derived from psub201 [Samulski et al, *J. Virol.*, 61:3096–3101 (1987)] and contains an *E. coli* β-galactosidase minigene in place of AAV Rep and Cap genes. The 5' to 3' organization of the recombinant AV.CMVLacZ genome (4.9 kb) [SEQ ID NO: 4] includes (a) the 5' AAV ITR (bp 1–173) was obtained by PCR using pAV2 [C. A. Laughlin et al, *Gene*, 23: 65–73 (1983)] as template [nuc. 53–219];

(b) a CMV immediate early enhancer/promoter [Boshart et al, *Cell*, 41:521–530 (1985)] (nuc. 246–839);

(c) an SV40 intron (nuc. 856–987);

(d) *E. coli* β-galactosidase cDNA (nuc. 1039–4512);

(e) an SV40 polyadenylation signal (a 237 Ban HI-BclI restriction fragment containing the cleavage/poly-A signals from both the early and late transcription units (nuc. 4522–4719) and (f) 3'AAV ITR, obtained from pAV2 as a SnaBI-BglII fragment (nuc. 4759–4925). All other nucleotides are plasmid derived.

Rep and Cap genes were provided by a transacting plasmid pAAV/Ad [Samulski et al, cited above].

Monolayers of 293 cells grown to 90% confluency in 150 mm culture dishes ($5 \times 10^7$ cells/plate) were infected with H5.CBALP at an MOI of 10. H5.CBALP (also called H5.010ALP) is a rAd that contains an alkaline phosphatase minigene in place of adenovirus E1a and E1b gene sequences (map units 1–9.2 of the Ad5 sequence of GenBank [Accession No. M73260]). The alkaline phosphatase cDNA is under the transcriptional control of a CMV-enhanced β-actin promoter in this virus. This helper virus is described in Goldman et al, *Hum. Gene Ther.*, 6:839–851 (July, 1995); Engelhardt et al, *Hum. Gene Ther.*, 5:1217–1229 (October, 1994); and references cited therein.

Infections were done in Dulbecco's Modified Eagles Media (DMEM) supplemented with 2% fetal bovine serum (FBS) at 20 ml media/150 mm plate. Two hours post-infection, 50 µg plasmid DNA (37.5 µg trans-acting and 12.5 µg cis-acting) in 2.5 ml of transfection cocktail was added to each plate and evenly distributed. Transfections were calcium phosphate based as described [B. Cullen, Meth. Enzymol., 152:684–704 (1987)]. Cells were left in this condition for 10–14 hours after which the infection/transfection media was replaced with 20 ml fresh DMEM/2% FBS. Forty to fifty hours post-transfection, cells were harvested, suspended in 10 mM Tris-Cl (pH 8.0) buffer (0.5 ml/150 mm plate) and a lysate prepared by sonication. The lysate was brought to 10 mM manganese chloride, after which bovine pancreatic DNase I (20,000 units) and RNase (0.2 mg/ml final concentration) were added, and the reaction incubated at 37° C. for 30 minutes. Sodium deoxycholate was added to a final concentration of 1% and incubated at 37° C. for an additional 10 minutes.

The treated lysate was chilled on ice for 10 minutes and solid CsCl added to a final density of 1.3 g/ml. The lysate was brought to a final volume of 60 ml with 1.3 g/ml CsCl solution in 10 N Tris-Cl (pH 8.0) and divided into three equal aliquots. Each 20 ml sample was layered onto a CsCl step gradient composed of two 9.0 ml tiers with densities 1.45 g/ml and 1.60 g/ml.

Centrifugation was performed at 25,000 rpm in a Beckman SW-28 rotor for 24 hours at 4° C. One ml fractions were collected from the bottom of the tube and analyzed on 293 or 293(E4) cells for LaCZ transduction. Fractions containing peak titers of functional AV.CMVLacZ virus were combined and subjected to three sequential rounds of equilibrium sedimentation in CsCl. Rotor selection included a Beckman NVT-90 (80,000 rpm for 4 hours) and SW-41 (35,000 rpm for 20 hours). At equilibrium, AV.CMVLacZ appeared as an opalescent band at 1.40–1.41 g/ml CsCl. Densities were calculated from refractive index measurements. Purified vector was exchanged to 20 mM HEPES buffer (pH7.8) containing 150 mM NaCl (HBS) by dialysis and stored frozen at −80° C. in the presence of 10% glycerol or as a liquid stock at −20° C. in HBS/40% glycerol.

Purified virus was tested for contaminating H5.CBALP helper virus and AV.CMVLacZ titers. Helper virus was monitored by histochemical staining for reporter alkaline phosphatase activity. A sample of purified virus representing 1.0% of the final product was added to a growing monolayer of 293 cells seeded in a 60 mm plate. Forty-eight hours later, cells were fixed in 0.5% glutaraldehyde/phosphate buffered saline (PBS) for 10 minutes at room temperature, washed in PBS (3×10 minutes) and incubated at 65° C. for 40 minutes to inactivate endogenous alkaline phosphatase activity. The monolayer was allowed to cool to room temperature, rinsed once briefly in 100 m Tris-Cl (pH9.5)/100 mM NaCl/5 mM MgCl, and incubated at 37° C. for 30 minutes in the same buffer containing 0.33 mg/ml nitroblue tetrazolium chloride (NBT) and 0.165 mg/ml 5-bromo-4-chloro-3-indolylphosphate p-toluidine salt (BCIP). Color development was stopped by washing the monolayer in 10 mM Tris-Cl (pH 8.0)/5 mM EDTA. Routinely the purification scheme described above removed all detectable H5.CBALP helper virus by the third round of buoyant density ultracentrifugation.

AV.CMVLacZ titers were measured according to genome copy number (virus particles/ml), absorbance at 260 nm ($A_{260}$ particles/ml) and LacZ Forming Units (LFU/ml). Virus particle concentrations were based on Southern blotting. Briefly, a sample of purified AV.CMVLacZ was treated with capsid digestion buffer (50 mM Tris-Cl, pH 8.0/1.0 mM EDTA, pH 8.0/0.5% SDS/Proteinase K 1.0 mg/ml) at 50° C. for one hour to release virus DNA. The reactions were allowed to cool to room temperature, loading dye was added and electrophoresed through a 1.2% agarose gel. Standard quantities of ds AV.CMVLacZ genome were also resolved on the gel.

DNAs were electroblotted onto a nylon membrane, hybridized with a $^{32}P$ random primer labeled restriction fragment, and the resulting blot scanned on a PhosphorImager 445 SI (Molecular Dynamics). A standard curve was generated from the duplex forms and used to extrapolate the number of virus genomes in the sample. LFU titers were generated by infecting indicator cells with limiting dilutions of virus sample. Indicator cells included HeLa and 293 and 293 (E4) lines (described in Example 10 below). Twenty-four hours later, cells were fixed in glutaraldehyde and cells were histochemically stained for *E. coli* β-galactosidase (LacZ) activity as described in J. M. Wilson et al, *Proc. Natl. Acad. Sci. USA*, 85:3014–3018 (1988). One LFU is described as the quantity of virus that is sufficient to cause visually detectable β-galactosidase expression in one cell 24 hours post-infection.

B. Induction of ORF6 Expression

Induction of ORF6 expression with 10 µM dexamethasone or 150 µM zinc sulfate (for negative control, no inducer used) was initiated 2 hours before the addition of virus and continued throughout the duration of the experiment. Twenty-four hours after the addition of virus, cells were harvested, lysates were generated by sonication and analyzed for the β-galactosidase expression (i.e., β-galactosidase activity) and virus DNA as described above. Hirt extracts were prepared from low molecular weight DNA from cell extracts. The preparation of the Hirt extracts and subsequent analysis by Southern hybridization were performed by resort to conventional procedures known to one of skill in the art.

In the absence of the inducers, the packaging cell lines generate lower levels of β-galactosidase in rAAV infected cells. Induction of ORF6 expression with the inducer dexamethasone results in a concomitant rise in AV.CNVLaCZ cell transduction to a level that was such greater than the parent 293 line. Expression of E1 alone was insufficient to have an effect in the adenovirus mediated augmentation of rAAV transduction.

Results are demonstrated for certain positive clones in the Table I below (see Example 4). However, for 30 cell lines having an MTV promoter and ORF6 sequence, 4 demonstrated over 90% blue cells illustrative of LacZ production in the presence of dexamethasone, i.e., 293-27-6, 293-27-17, 293-27-18 and 293-27-28.

Example 3

Immunofluorescence Localization of Ad5 Late Protein

Positive clones from the assay of Example 2 were infected with the recombinant E4 deleted adenovirus H5dl1004 and screened for E4 complementation using an immunofluorescence assay for late gene expression. The H5dl1004 virus was obtained from Dr. Ketner of Johns Hopkins University and is described in Bridge. and Ketner, *J. Virol.*, 632(2):631–638 (February 1989), incorporated by reference herein. Because ORF6 of E4 complements late Ad gene expression, specifically in the formation of the hexon and penton fibers of the adenovirus, cell lines containing ORF6 are able to bind with antibody against these proteins.

Each cell line of Example 1 is infected with E4 deleted virus H5dl1004 virus at an MOI of 0.1. The cells were treated with mouse anti-adenovirus FITC-labeled monoclonal antibody to either the hexon or penton fibers in a 1:10 dilution (Chemicon International Inc., Temecula, Calif.). Positive clones were identified by reaction with the antibody.

Example 4

Relative Plaguing Efficiency

The cell lines of Example 1, demonstrating strong complementation ability in Example 3, were screened for relative plaquing efficiency of H5dl1004 as compared to W162 cells (an E4-complementing Vero cell line which does not express E1) [Weinberg and Ketner, *Proc. Natl. Acad. Sci. USA*, 80(17):5383–5386 (1983)). In Table II below, RPE %, i.e., relative plaquing efficiency, represents the titer of H5dl1004 on tested cell lines/titer of H5dl1004 on W162 cells. For example, the RPE of 293 cells is 0.

The positive cell lines selected by all criteria are identified in Table I below, with the results of the assays of Examples 2, 3 and 4.

TABLE I

E1/E4 Double Complementing Cell Lines

| Cell Line | Trans-Gene | Promoter | IF/LP | AV. CMV LacZ | RPE % |
|---|---|---|---|---|---|
| 293-10-3 | ORF6 | MT | ++++ | ++++ | 246 |
| 293-39-11 | ORF6 | LTR | ++++ | +++ | 52 |
| 293-84-31 | E4– | LTR | ++++ | ++++ | 179 |
| 293-12-31 | whole E4 | LTR +E4 | ++++ | ++++ | 174 |
| 293-27-6 | ORF6 | MMTV | | +++++ | 327 |
| 293-27-17 | ORF6 | MMTV | | ++++ | 313 |
| 293-27-18 | ORF6 | MMTV | | +++++ | 339 |
| 293-27-28 | ORF6 | MMTV | | ++++ | 261 |

Example 5

Construction and Purification of H5.001CBLacZ

The plasmid pAd.CBLacZ was constructed as described in detail in K. Kozarsky et al, *Som. Cell Mol. Genet.*, 19(5):449–458 (1993), incorporated by reference herein. This plasmid contained a minigene comprising a 5' flanking NheI restriction site, followed by Ad5 sequence m.u. 0–1, followed by an E1 deletion into which is inserted a CMV enhancer/chicken β-actin promoter sequence [T. A. Kost et al, *Nucl. Acids Res.*, 11(23):8287 (1983)], which controls the transcription of the following bacterial β-galactosidase, followed by a poly A sequence and flanked 3' by Ad m.u. 9–16, and another NheI site. In the plasmid, the minigene was flanked on both sides by plasmid sequence containing drug resistance markers.

The plasmid pAd.CBLacZ was linearized with NheI and co-transfected by the calcium phosphate co-transfection method into the novel packaging cell line of Example 1 with ClaI digested H5dl1004 (an Ad5 sequence deleted of from about map unit 92.1 through map unit 98, corresponding to substantially the entire E4 gene).

Figure 2:
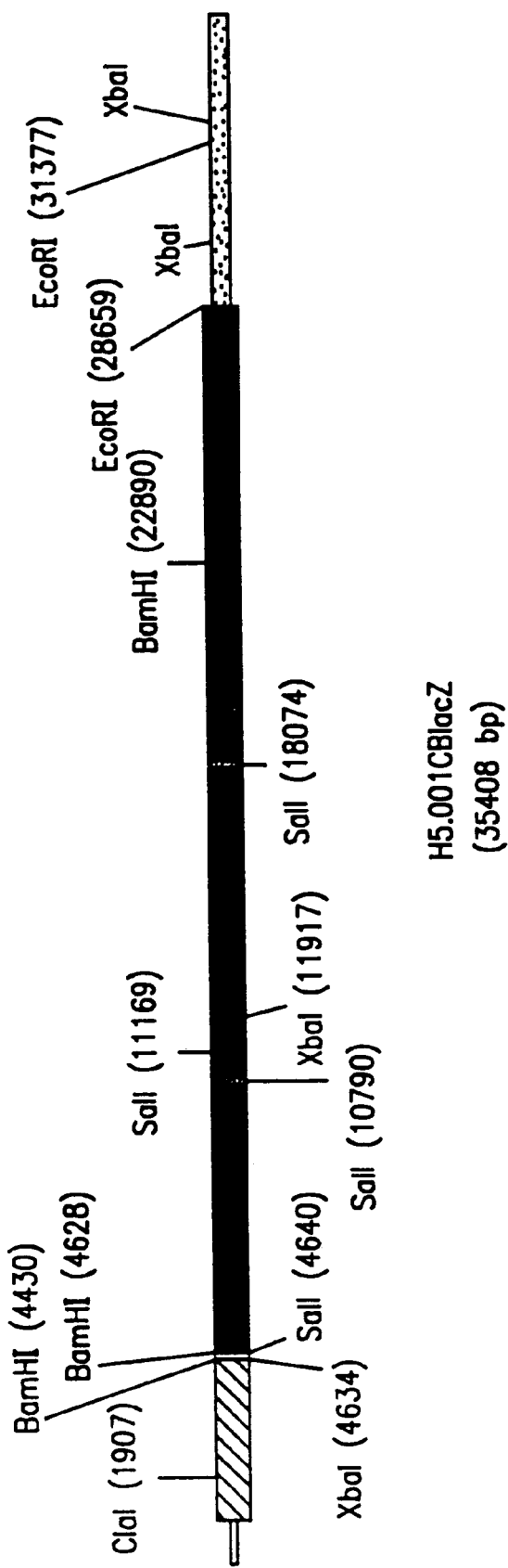
FIG. 2 is a schematic map of rAd H5.001CBLacZ [SEQ ID NO: 3] with indicated restriction endonuclease enzyme sites. The striated bar represents the CBLaCZ minigene; the black bar represents Ad5 viral backbone, the crosshatched bar represents Ad E4 deletion.

Homologous recombination occurs in the cell line between these two viral constructs between Ad map units 9–16, resulting in rAd, designated H5.001CBLacZ [SEQ ID NO: 3] (FIG. 2). This rAd contains the sequence from pAd.CBLacZ (including Ad map units 0–1 (nuc. 1–330); CMV enhancer/chicken β-actin promoter (CB) (nucs. 370–928); *E. coli* β-*galactosidase (nucs.* 945–4429); the polyA (nuc. 4429–4628); and Ad5 map units 9–92.1 and 97.3 to 100 from H5dl1004 (nucs. 4671–35408)). This rAd is thereby functionally deleted, and substantially structurally deleted, of the Ad E1 and E4 genes.

Viral plaques were selected and screened by the β-galactosidase assay (Wilson (1988), cited above] and H5.001CBLacZ was isolated following three rounds of plaque purification. The purified virus was also subjected to cesium chloride density centrifugation and large scale production.

For the following mouse experiments, virus was used after column purification and glycerol was added to a final concentration of 10% (v/v). Virus was stored at −70° C. until use.

Example 6

Growth Kinetics of H5.001CBLacZ in Packaging Cell Lines

Figure 3:
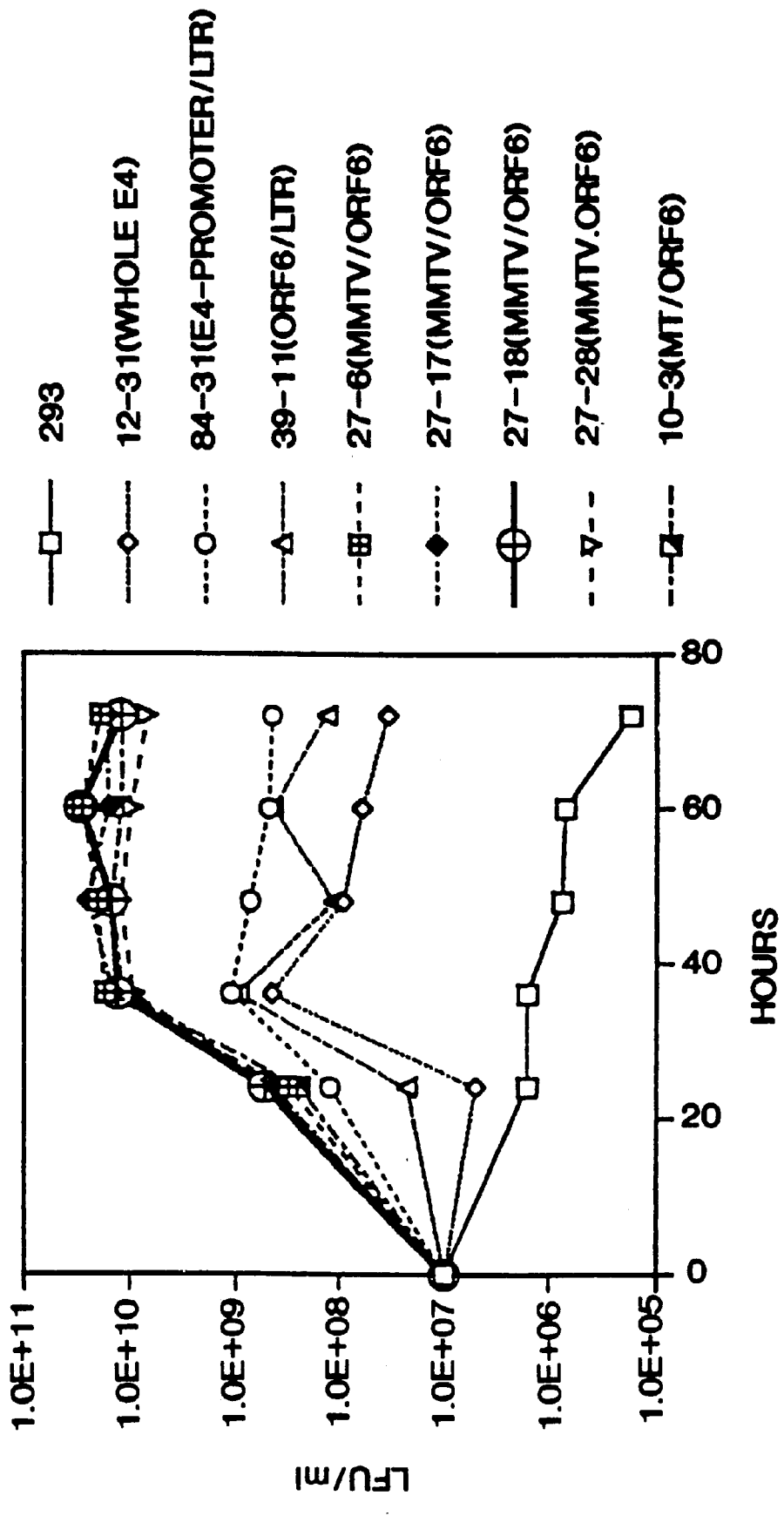
FIG. 3 plots LacZ forming units (LFU)/ml vs time (hours) for E4 complementing cell lines infected with H5.001CBLacZ.
Figure 4A:
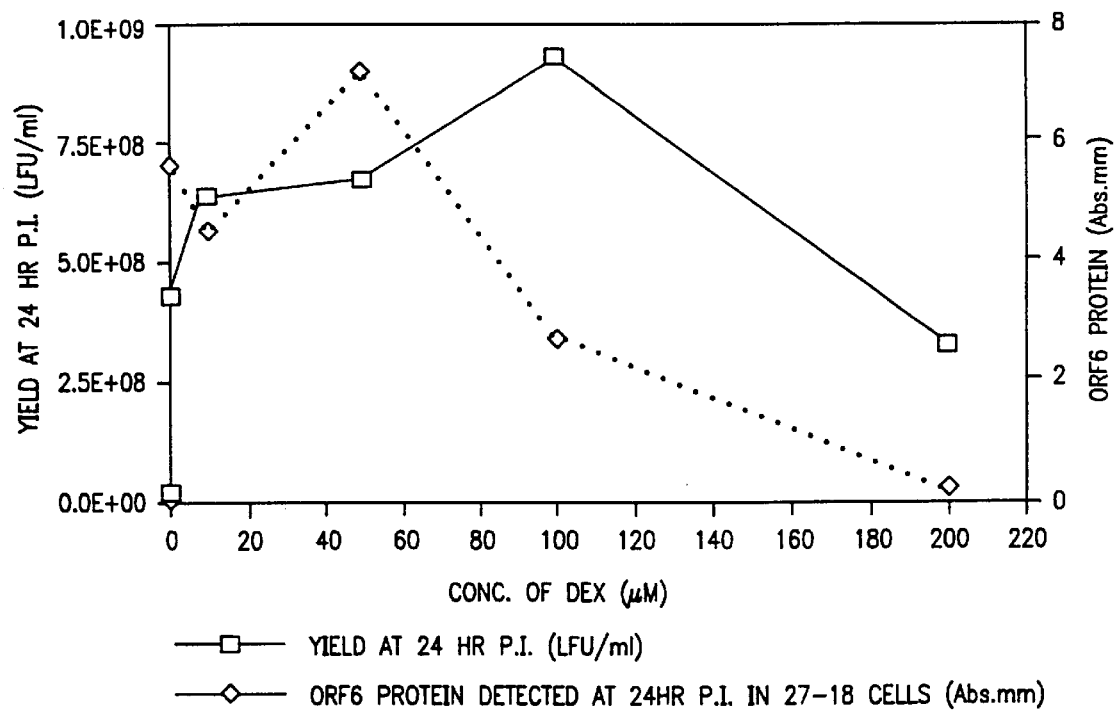
FIG. 4A is a graph of the induction, ORF6 expression and viral production in 293-27-18 packaging cells plotting yield at 24 hours post-infection (pi) in LFU/ml and ORF6 protein (abs.mm) vs. concentration of the inducer, dexamethasone ($\mu$M). Abs.mm is the intensity of the size of the protein band on a Western blot and reflects absorbance and protein size in mm$^2$. The square is yield at 24 hours pi. The diamond is ORF6 protein detected at 24 hours pi.
Figure 4B:
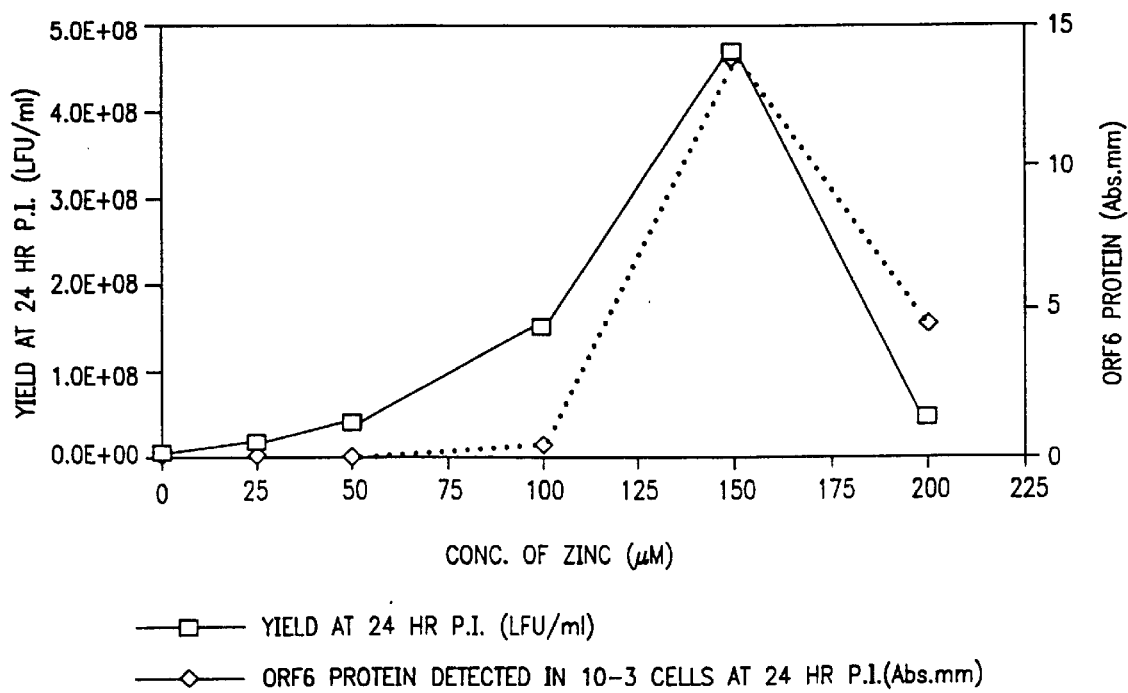
FIG. 4B is a similar graph to that of FIG. 4A, except that the packaging cells are 293-10-3 cells. The symbols are an described for FIG. 4A.

The cell lines identified in Table I were infected with recombinant H5.001CBLacZ at an MOI of 0.5. The growth kinetics of this virus in the E4 complementing cell lines are shown in FIG. 3. Maximum viral yield is reported as LFU/ml in Table II below.

TABLE II

| Cell Line | Maximum Viral Yield |
|---|---|
| 293-10-3 | $2.8 \times 10^{10}$ |
| 293-39-11 | $9.5 \times 10^{8}$ |
| 293-84-31 | $1.1 \times 10^{9}$ |
| 293-12-31 | $4.5 \times 10^{8}$ |
| 293-27-6 | $2.8 \times 10^{10}$ |
| 293-27-17 | $2.5 \times 10^{10}$ |
| 293-27-18 | $2.9 \times 10^{10}$ |
| 293-27-28 | $1.2 \times 10^{10}$ |

When grown in 293-27-18 cells (the E4 ORF6 cell line with MMTV promoter inducible by dexamethasone) the maximum yield of this virus is $2.9 \times 10^{10}$ LFU/ml. Several of the cell lines were passaged between 5 and 20 times and the viral production of the passages remained stable. However, RPE did fall following repeated passages of cells.

Example 7

Other Recombinant Adenoviruses

Other related rAds were prepared similarly to H5.001CBLacZ by homologous recombination between pAdCBLacZ and other helper viruses.

As one example, H5.000CBLacZ is a recombinant E1 deleted Ad5 which contains the same minigene as H5.001CBLacZ, but has an intact E4 gene. This rAd was prepared as described by homologous recombination between pAdCBLacZ and a wild-type Ad5.

As another example, H5.010CBLacZ contains the adenovirus map units 0–1, followed by a CMV enhanced, chicken cytoplasmic β-actin promoter, the *E. coli* β-galactosidase gene (lacZ), a polyadenylation signal (pA), and adenovirus type 5 map units 9–100, with a small deletion in the E3 gene (the Ad 5 sub360 backbone). This rAd may be prepared by homologous recombination between the pAdCBLacZ vector and Ad5 virus sub360, which contains a 150 bp deletion within the 14.6 kD protein of the E3 gene. See, e.g., J. F. Engelhardt et al, *Proc. Natl. Acad. Sci.. USA*, 21:6196–6200 (June 1994); and Engelhardt et al, *Hum. Gene Ther.*, 5:1217–1229 (October 1994), both incorporated by reference herein.

These rAds were isolated following transfection [Graham, *Virol.*, 52:456–467 (1974)], and were subjected to two rounds of plaque purification. Lysates were purified by cesium chloride density centrifugation as previously described [Englehardt et al, *Proc. Natl. Acad. Sci. USA*, 88:11192–11196 (1991)]. Cesium chloride was removed by passing the virus over a BioRad DG10 column using phosphate-buffered saline.

Example 8

LacZ Gene Transfer into Mouse

A. Transfer into Mouse Muscle

Five to six-week old male C57B/6 mice were anesthetized. Anterior tibialis muscles were exposed and directly injected with either rAd H5.000CBLaCZ, H5.010CBLacZ or H5.001CBLacZ as follows: 25 μL of purified viral suspension at a stock concentration of $5\times10^{11}$ virus particles/mL was injected by inserting the tip of the 33 gauge needle of a 100 μL Hamilton syringe into the belly of the muscle.

Animals were sacrificed on day 4, 14, 28 and 60 post injection. The muscles were dissected and frozen in liquid nitrogen cooled isopentane. Six μM sections were cut in a cryostat, fixed and stained for β-galactosidase activity for 6 hours at 37° C.

While the blue stained rAd was found for each virus in the day 4 and day 14 (most abundant) stains, by day 28, the H5.001CBLacZ clearly demonstrated more virus on day 28. By day 60, the only virus which stained positive was the H5.001CBLacZ.

B. Transfer into Mouse Lung and Circulation

RAd H5.001CBLacZ (control), and H5.001CBLacZ ($1\times10^{11}$ viral particles) were administered to six week old C57BL/6 female mice by tail vein injection and trachea installation. The animals were sacrificed and their liver and lung tissues were harvested at days 4, 9, 21, 28 and 35 post-administration. The transgene and viral late gene expression were compared.

At therapeutic doses of virus, there was diminished expression of late viral proteins at all time points in comparison with transgene.

C. Dose Responses in Liver

Dose responses of E4-deleted and E4 intact rAds in the liver of C57BL/6 mice were studied by tail vein administration of $1.5\times10^{11}$, $5\times10^{10}$, $1.7\times10^{10}$, $5.6\times10^{9}$, and $1.9\times10^{9}$ viral particles and comparing the transgene and viral late gene expression at day 4, 21, 28, 35, and 42 post administration.

At therapeutic doses of virus, there was diminished expression of late viral proteins at all time points in comparison with transgene.

Example 9

Other Gene Transfers

A. Human OTC Gene Transfer

The human OTC gene [A. L. Horwich et al, *Science*, 224:1068–174 (1984)] or the human CFTR gene [Riordan et al, *Science*, 245:1066–1073 (1989)) was used to replace the LacZ as the transgene in the recombinant E1/E4 deleted adenoviruses described above, using the techniques analogous for the construction of the above-described LacZ vectors.

The resulting human OTC-containing rAd were administered at an MOI of 10 to 30 to human hepatocytes. The E1/E4 deleted rAd demonstrated less replication and less late gene expression than when the E1/E4 deleted rAds are administered to muscle, as described in the example above. However, the results of this gene transfer are better than comparable transfers with rAds containing only a deletion in the E1 gene or a deletion in the E1 gene and a point mutation in the E2a gene.

Similar results are demonstrated when the transgene is CFTR and the method of administration is intratracheal into lungs.

Example 10

Transduction Efficiency of rAAV LacZ AV.CMVLacZ) in HeLa Cells Infected with Ad Mutants

A. Viruses

The following viruses were employed in this experiment:

(1) Wild-type Ad 5, propagated in 293 cells;

(2) Ad dlllo (an Ad which is deleted of the 55 kb E1B gene) [Babiss et al, *J. Virol.*, 52(2):389–395 (1984) and Babiss and Ginsberg, *J. Virol.*, 50(1):202–212 (1984)], propagated in 293 cells, (3) H5.CBALP (an Ad deleted of its E1A and E1B genes and containing a minigene that expresses alkaline phosphatase from a CMV enhanced β-actin promoter, as described above), propagated in 293 cells, (4) Ad ts125 (an Ad with a temperature sensitive mutation in the E2A gene which encodes the DNA binding protein) [Ensinger and Ginsberg, *J. Virol.*, 10(3):328–339 (1972)], propagated in 293 cells, (5) Ad d1802 (an Ad deleted of its E2a gene), grown in E2A-complementing gmDBP cells as described in Rice and Klessig, *J. Virol.*, 56(3):767–778 (1985);

(6) Ad dl1004 (an Ad deleted of the E4 gene), grown in E4-complementing Vero W162 cells [Weinberg and Ketner, *Proc. Natl. Acad. Sci USA*, 80(17):5383–5386 (1983)] and (7) Ad dl1010 (an Ad deleted of ORF6 of its E4 gene), grown in E4-complementing Vero W162 cells [Weinberg and Ketner, cited above].

All viruses were purified by two sequential rounds of buoyant density ultracentrifugation in CsCl.

B. Experimental Procedures

HeLa cells seeded in 6 well, 36 mm culture plates ($2\times10^6$ cells/well) were infected with wild-type Ad5 or an adenovirus early gene mutant as described in Part A at an MOI of 10 pfu/well. Infections were done in 1.0 ml DMEM/2%FBS. Six hours post-infection, monolayers were washed and 1.0 ml fresh DMEM/2% FBS media containing AV.CMVLacZ at $4\times10^9$ virus particles/ml were added. Although the AV.CMVLacZ virus lot used in these experiments was shown to be free of H5.CLALP helper virus by histochemical staining, the virus sample was subjected to heat treatment (60° C. for 20 minutes) prior to use to ensure the absence of contaminating adenovirus. Two hours later, 1.0 ml of DMEM/115% FBS was added to each well.

Twenty-four hours after the addition of AV.CVLacZ, cells were harvested. Each test condition was done in triplicate to enable virus transduction to be evaluated in terms of three outputs: histochemical staining for β-galactosidase activity (below), intracellular β-galactosidase specific activity (Example 11), and the molecular form of the virus DNA (Example 12).

HeLa cells were histochemically stained for *E. coli* β-galactosidase (LacZ) activity as described in J. M. Wilson et al, *Proc. Natl. Acad. Sci. USA*, 85:3014–3018 (1988). The different combinations that were tested included cells transfected with AAV vector alone (AV.CMVLacZ), vector plus wild-type Ads (+Ad5), vector plus dl110 (+dl110), vector plus Ad mutant H5.CBALP (+H5.CBALP), vector plus Ad mutant ts125 (+ts125), vector plus Ad mutant d1802 (+d1802), vector plus Ad mutant dl1004 (+dl1004), and vector plus Ad mutant dl1010 (+dl1010).

The results were observed in photomicrographs at magnification 10X (not pictured) of histochemical stains for recombinant β-galactosidase activity. The results indicated that wild-type Ad5 and the E2a mutants ts125 and d1802 caused a significant increase in LacZ rAAV transduction as measured by the number of positive blue cells and the degree of stain intensity. Both dl110 (E1B-55 kDa) and dl1010 (ORF6) enhanced transduction to levels that approached those of Ads, ts125, and d1802 in terms of the number of positive blue cells.

The E1 deletion recombinant H5.CBALP provided no significant increase in AV.CMVLacZ transduction. Expression of E1 alone was insufficient to have an effect in the adenovirus mediated augmentation of rAAV transduction as evidenced by lack of significant increase in transduction obtained with HeLa cells infected with the E4 deletion mutant dl1004. A significant drop in transduction occurred following removal of ORF6 from the E4 region from the coinfecting adenovirus (FIG. 5A).

It is believed that these results demonstrate that the adenoviral gene products, E4 and E1 indirectly promote the formation of ds DNA intermediates that are transcriptionally active.

Example 11

Quantitation of Enhanced Vector Transduction (A) A duplicate set of HeLa cells as described in Example 10B were used in this experiment. Twenty-four hours after the addition of AV.CMVLacZ recombinant, for intracellular β-galactosidase assays, cell pellets were suspended in 0.5 ml PBS and sonicated. Cell debris was removed by centrifugation (15,000Xg for 10 minutes) and the clarified extract assayed for total protein [M. Bradford, *Anal. Biochem.*, 72(1–2):248–254 (1976) and M. Bradford et al, *Fed. Proc.*, 35(3):274 (1976)] and β-galactosidase activity [Sambrook et al, cited above] using o-nitrophenyl β-D-galactopyranoside (ONPG) as substrate.

FIG. 5A demonstrates the transduction efficiency quantitated by measuring β-galactosidase enzyme activity in the lysates from infected Hela cells and also assayed for total protein. In FIG. 5A, the test condition is shown along the horizontal axis, and intracellular β-galactosidase specific activity (milliunits/mg protein) using ONPG as substrate is plotted on the vertical axis. Below each bar, the fold-induction in specific activity relative to cells that received the AV.CMVLacZ vector alone is given.

The results of FIG. 5A demonstrate that the E2a mutants ts125 and d1802 produced 134-fold and 225-fold increases in β-galactosidase activity, respectively, as compared to that achieved with purified rAAV alone. In comparison, cells infected with wt Ad5 generated 107-fold increase in β-galactosidase activity.

(B) In another experiment, HeLa cells ($2\times10^6$) were infected with increasing multiplicities of wild-type Ad5 or the E2 mutant d1802. Six hours post-infection, monolayers were washed and infected with AV.CMVLacZ at 1000 virus particles/cell. Twenty-four hours after the addition of AV.CMVLacZ, cells were harvested and assayed for total protein and β-galactosidase activity.

Figure 5B:
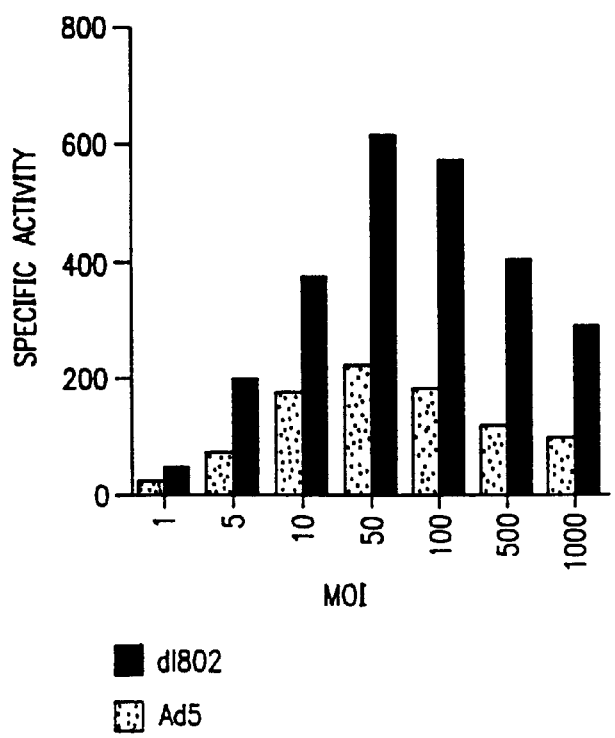
FIG. 5B is a bar graph plotting Ad multiplicity of infection (MOI) in Hela cells of wild-type Ad5 or the E2 mutant d1802, the cells co-infected with rAAV vs. intracellular β-galactosidase specific activity. See Example 11.

The results are illustrated in the bar graph of FIG. 5B, in which adenovirus MOI's are given along the horizontal axis, and intracellular β-galactosidase specific activity along the vertical axis. Enhancement of rAAV transduction was proportional to input helper adenovirus from MOIs of 1 to 50 for both wild type Ad5 and d1802. Higher doses of virus were cytopathic, leading to a fall in β-galactosidase expression. Enhanced transduction was achieved when the cells were infected prior to, or at the time of, rAAV infection. The E1 deletion recombinant H5.CBALP and the E4 deletion mutant dl1004 provided no significant increase in AV.CMVLaCZ transduction. Both cells infected with dl1110 (E1B-55 kDa) and with dl1010 (ORF6) demonstrated substantially lower total β-galactosidase activity than those infected with Ad5, ts125, or d1802.

Example 12

Analysis of Low Molecular Weight DNAs in AV.CMVLacZ Transduced Cells

Studies with these early gene mutants of adenovirus suggested that expression of adenoviral genes rather than the virion itself was responsible for enhancement of rAAV transduction. To further investigate these mechanisms and to determine if conversion of ss to ds genome limits the transduction efficiency of rAAV, the molecular state of the rAAV genome was characterized in the infected cells. The relationship between RFm formation and lacZ rAAV transduction was explored in experiments where the dose of coinfecting virus was varied (MOI=1, 5, or 10).

(A) A duplicate set of HeLa monolayers as described in Example 10 were harvested 24 hours after they were transduced with the recombinant AV.CMVLacZ and cultured with or without helper adenovirus.

Episomal DNA was extracted from cell pellets using a modification of the procedure originally described by B. Hirt, *J. Mol. Biol.*, 26:365–369 (1967). Briefly, cells were suspended in 320 ml Tris-Cl (pH8.0)/10 mM EDTA and SDS added to a final concentration of 1%. The mixture was incubated at 37° C. for 30 minutes. Pronase and proteinase X were added to final concentrations of 500 μg/ml and 20 μg/ml, respectively, and the reaction incubated at 37° C. for 2 hours. Sodium chloride was added to a final concentration of 1.1 M and incubated at 4° C. overnight. The precipitate that developed during the 4° C. incubation was pelleted at 20,000 xg for 30 minutes and the clear supernatant carefully removed. The supernatant was extracted once with phenol:chloroform:isoamyl alcohol (25:24:1) followed by chloroform:isoamyl alcohol (24:1). Nucleic acids were precipitated with ethanol. The final pellet was suspended in 50 ml Tris-Cl (pH 8.0)/1.0 mM EDTA.

These Hirt extracts were analyzed by Southern blot hybridization. Samples (5 μl) of each Hirt extract were resolved through a 1.2% agarose gel, electroblotted onto a nylon membrane and hybridized with a $^{32}$P random primer labeled cDNA of the SV40 polyA signal used in AV.CMV-LacZ.

An autoradiogram of the experiment of Example 12 (not pictured), identifies and labels bands corresponding to the ss AV.CMVLacZ genome (SS), a monomer replicative form (RFm), and concatomer replicative forms (RFd). Bands corresponding to the ss AV.CMVLacZ genome (SS), a monomer replicative form (RFm), and concatomer replicative forms (RFd) were identified and labeled. To reference the RFm band, a plasmid carrying AV.CNVLacZ was digested to release the entire genome. Autoradiogram exposure times were 14 hours and 69 hours.

In this autoradiogram, the full spectrum of molecular species present during a lytic infection was demonstrated in cells infected with both LacZ rAAV and wild type adenovirus. Both the input ss genome (SS) and monomeric and dimeric forms of ds replicative intermediates (RFm and RFd) are present. This contrasts with cells infected with purified rAAV alone, where ss genome is the sole molecular form detected. Analysis of cells coinfected with the adenovirus early gene mutants revealed a direct correlation between formation of ds forms of the rAAV genome and the enhancement of LacZ transduction. Mutant adenoviruses that were ineffective in enhancing rAAV transduction (i.e., the E1 deleted mutant H5.CBALP and the E4 deleted mutant dl1004) failed to promote the formation of ds forms of AAV.

Cells infected with adenovirus deleted of E2a (dl1802) or partially deleted of E1 (dl110) or E4 (dl1010) additionally demonstrated a band whose size was identical to the ds replicative monomer (RFm) of the lacZ rAAV genome and whose abundance correlated directly with the expression of β-galactosidase activity (compare results of Example 14 to these described results). Slower migrating concatomers, likely diners, of duplex rAAV were also detected in the autoradiogram described above.

In the presence of E1 and E4 expression, rAd transduction was invariably accompanied by the appearance of ds RP monomers and dimers.

The high molecular weight band in sample lane +H5.CBALP is helper virus DNA. Helper virus DNA is recognized by the SV40 probe because the CBALP minigene also utilizes the SV40 polyA signal.

(B) In another experiment, HeLa cells were infected with wt Ad5 or the E2 deleted mutant dl1802 as described in Example 10B. Monolayers were harvested 24 hours later and analyzed for β-galactosidase activity and RFm synthesis. Monomer bands similar to those shown in the autoradiogram described above were quantitated on a PhosphorImager 445 SI and assigned values (CPM).

Figure 6A:
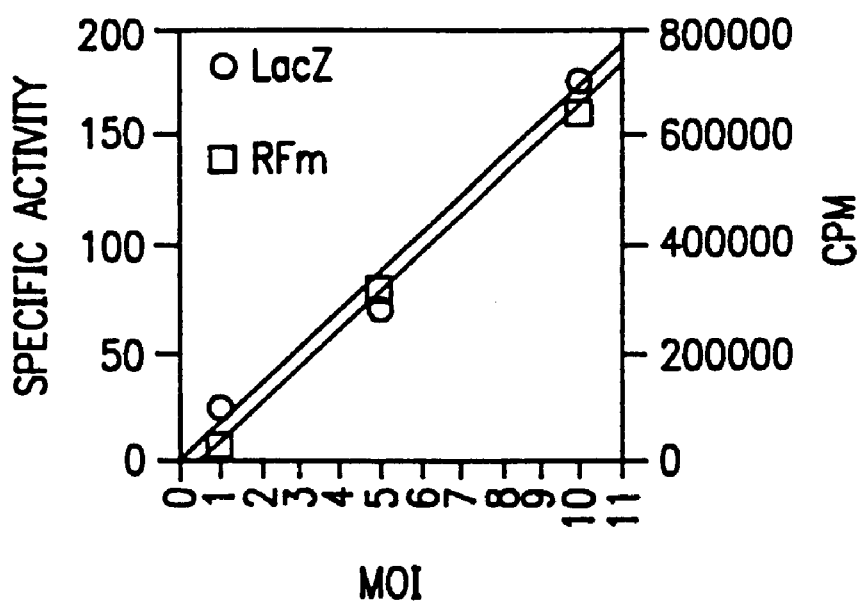
FIG. 6A is a graph in which β-galactosidase specific activity and counts per minute (CPM) are plotted along the vertical axis and adenovirus MOI's are on the horizontal axis for HeLa cells infected with wtAd5 and rAAV according to Example 12. Data obtained from low MOI (1, 5, and 10) infections are shown.
Figure 6B:
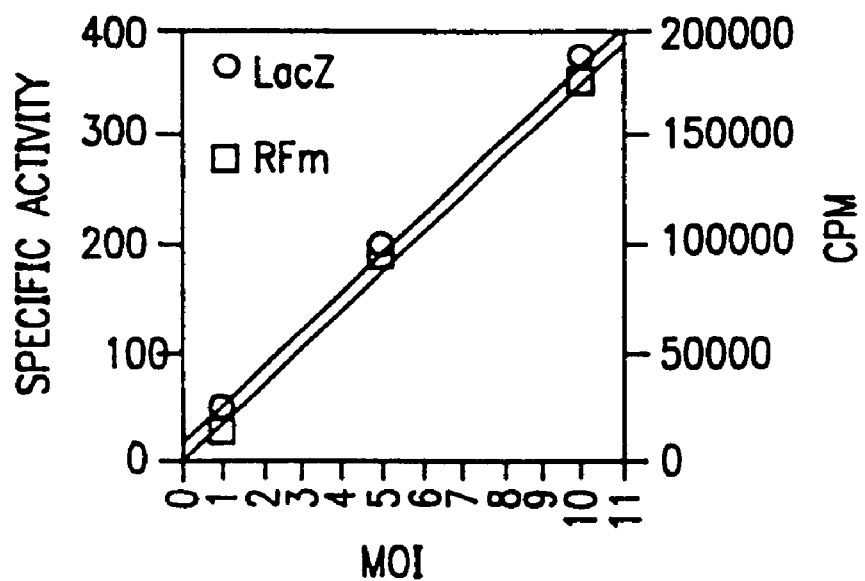
FIG. 6B is a graph similar to that of FIG. 6A except that the cells were infected with Ad mutant d1802.
Figure 8A:
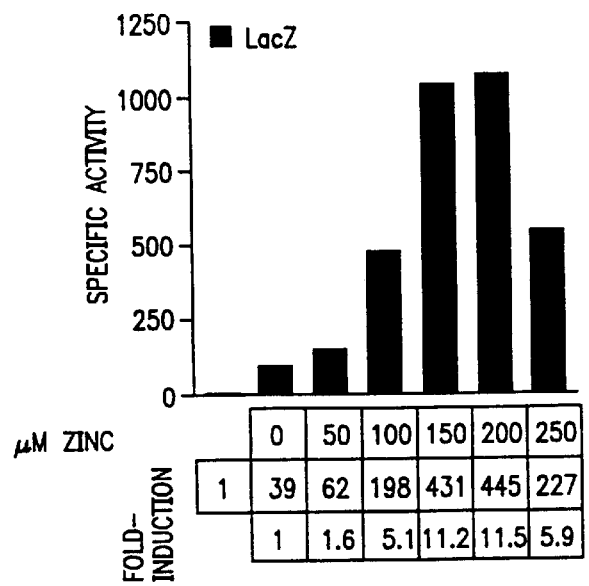
FIG. 8A is a bar graph plotting β-galactosidase specific activity (mUnits/mg protein) vs. increasing concentration of zinc ($\mu$M) inducer for cell line 293 (MT-ORF6) transduced with AVCMVLacZ (first row below each bar). Also provided is the fold-induction relative to 293 cells (second row below each bar), and the fold-induction relative to 293(ORF6) cells maintained in the absence of zinc (third row).
Figure 8B:
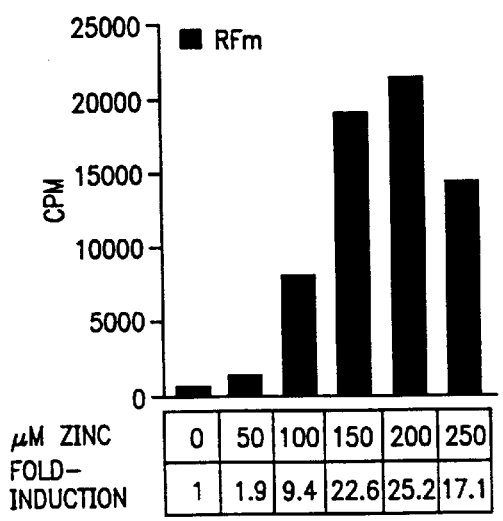
FIG. 8B is a bar graph plotting CPM of duplex monomer replicative form (RFm) of rAAV vs. the concentration of zinc ($\mu$M) used for induction and the fold-induction relative to 293(ORF6) cells maintained in 0 mM zinc below each bar.
Figure 8C:
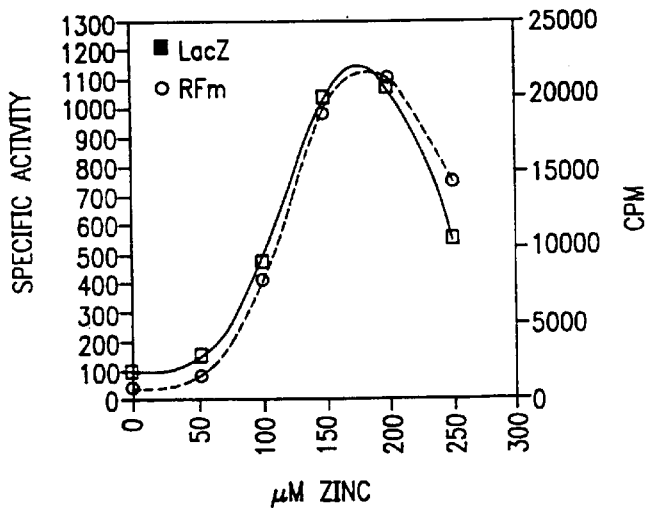
FIG. 8C is a graphical comparison of the induction profiles that describe AV.CMVLacZ transduction efficiency. Specific activity data from FIG. 8A and CPM data of AV.CMVLacZ RFm from FIG. 8B are plotted along the vertical axis, and concentration of zinc sulfate used during the experiment is shown along the horizontal axis.

The results are illustrated in the graphs of FIGS. 8A and 8B, in which β-galactosidase specific activity and CPM are plotted along the vertical axis of each figure. Adenovirus MOI's are given on the horizontal axis of each figure. Data obtained from low MOI infections (1, 5, and 10) are shown. Importantly, the tight correlation between rAAV vector transduction and the accumulation of duplex forms could be achieved in cells infected with E1/E4 expressing adenovirus. The level of β-galactosidase and abundance of RFm increased in proportion to the amount of infecting wild type Ad (FIG. 6A) and d1802 (FIG. 6B). These data suggest that synthesis of an episomal duplex intermediate is an obligatory event in transduction.

Example 13

Duplex End-Analysis

The following is a description of a model for leading strand synthesis of a complementary AAV strand in the presence of Rep (+Rep) or absence of Rep (−Rep). Refer to FIGS. 7A–7F. Rep expresses a terminal resolution activity that can convert a duplex structure with closed-ends to an open-ended duplex. In the absence of Rep, terminal resolution is impaired leaving the covalently closed, hairpin structures intact. Under these conditions, hairpins are expected to be found leftward and rightward, since both strands of a rescued ds AAV genome are packaged into virions. FIGS. 7B–7F are a flow chart demonstrating the strategy for identifying the terminal structure of duplex RFm that is synthesized from ss AV.CNVLaCZ in response to adenoviral gene expression.

Figure 7A:
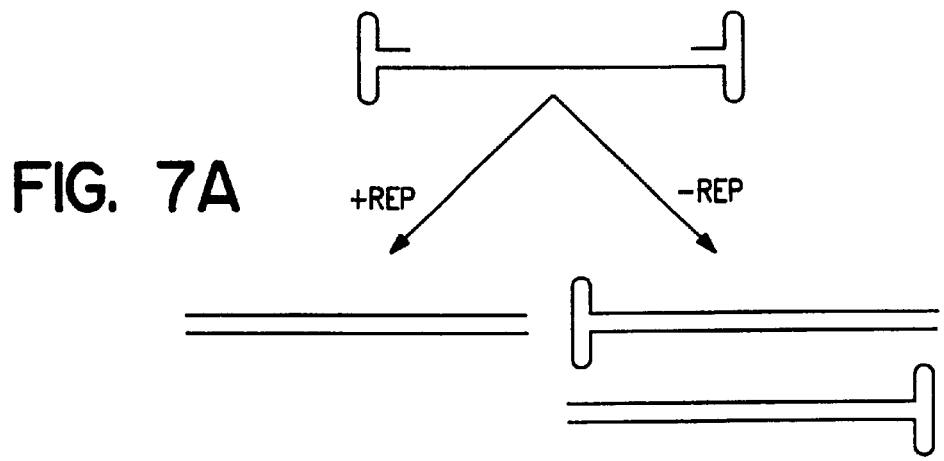
FIG. 7A illustrates a model for leading strand synthesis of a complementary AAV strand in the presence of Rep (+Rep) or absence of Rep (–Rep). Rep expresses a terminal resolution activity that can convert a duplex structure with closed-ends to an open-ended duplex. In the absence of Rep, terminal resolution is impaired leaving the covalently closed, hairpin structures intact. Under these conditions, hairpins are expected to be found leftward and rightward, since both strands of a rescued ds AAV genome are packaged into virions.
Figure 7B:
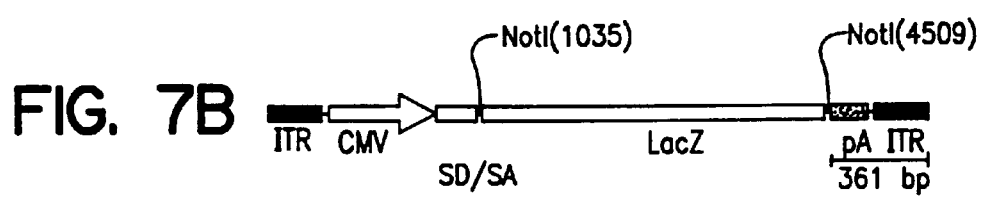
FIG. 7B is a schematic of linear AV.CMVLacZ with labeled domains including the AAV ITRS, CMV immediate early enhancer/promoter (CMV), SV40 splice donor-splice acceptor (SD/SA), E. coli β-galactosidase cDNA (LacZ), and SV40 polyA signal (pA). Two NotI sites located at bp positions 1035 and 4509 are indicated.
Figure 7C:
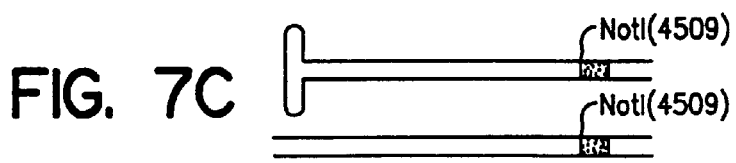
FIG. 7C illustrates a closed end and an open end fragment of rAV.CNVLacZ.
Figure 7D:
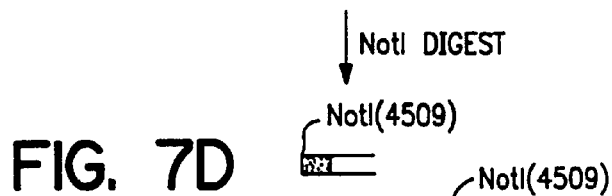
FIGS. 7D, 7E and 7F indicate the mixture of open-ended and covalently closed duplex fragments generated by NotI digestion of ss AV.CMVLacZ at position 4509 in the absence of terminal resolution. The NotI 4509 digestion provides a convenient means of releasing a 361 bp fragment that contains the right ITR in the context of a hybridization target (i.e. SV40 pA). In the presence of terminal resolution, only the open-ended 361 bp fragment would be expected to be generated (FIG. 7D) by such digestion.
Figure 7E:
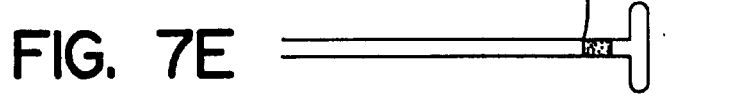
Figure 7F:
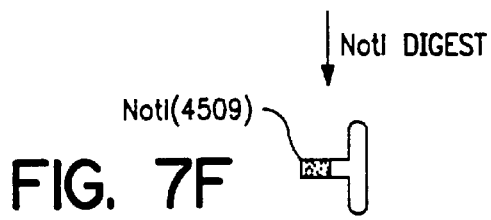

FIG. 7C illustrates a closed end and an open end fragment of rAV.CMVLacZ. FIGS. 7D, 7E and 7F indicate the mixture of open-ended and covalently closed duplex fragments generated by NotI digestion at position 4509 in the absence of terminal resolution. The NotI 4509 digestion provides a convenient means of releasing a 361 bp fragment that contains the right ITR in the context of a hybridization target (i.e. SV40 pA). In the presence of terminal resolution, only the open-ended 361 bp fragment would be expected to be generated (FIG. 7D) by such digestion.

The resulting electrophoretic gel (not pictured), revealed in lane (1) the results of digestion of a plasmid carrying an AV.CMVLacZ cDNA to release the rAAV vector and subsequent digestion with NotI to release the right terminal 361 bp fragment. In lane (2) a sample of NotI digested Hirt DNA extracted from HeLa cells infected with wild-type Ad5 and transduced with AV.CMVLaCZ resulted in the release of two fragments, labeled FormI and FormII. (See, also, FIGS. 8A and 8B). The migration of ss AV.CMVLacZ (SS) and RPm were also seen.

The ds AV.CMVLacZ intermediates that accumulated in calls infected with adenovirus were likely the result of leading strand DNA synthesis, initiating from the duplex region of the vector ITR. In the absence of Rep, this conversion event was anticipated to generate molecules in which one end is open and the other is covalently closed (FIG. 7A). To further characterize the structure of this ds intermediate Hirt extracts from cells coinfected with rAV.C-MBLacZ and Ad5 were digested with NotI to release the termini of the ds intermediate which, if left open, would be approximately 361 bp in length. The resulting filters were hybridized with a probe specific for the SV40 polyadenylation signal positioned immediately upstream of the rightward ITR. At least two forms were released from the right end of duplex genomes, one that migrated to a position in the gel that predicted an open-ended conformation (Form II), and a second slower migrating species (Form I). Although this result was consistent with the model (FIGS. 7A–7F), it was difficult to predict with certainty the structure of Form I. Its retarded mobility did, however, suggest a conformation that differed from the open-ended Form II.

Example 14

Analysis of AV.CMVLacZ Transduction Efficiency in 293 Cells Stably Transfected with an Inducible E4 ORF6 cDNA Cell lines used in this assay were prepared as described in Example 1. 293(MT-ORF6) cells and HeLa(MT-ORF6) cells were seeded in 6 well 35 mm culture plates ($2 \times 10^6$ cells/well) and infected with purified, heat-treated AV.CM-VLacZ at an MOI of 1000 virus particles/cell. Induction of ORF6 expression with from none to increasing concentrations of zinc sulfate was initiated 2 hours before the addition of virus and continued throughout the duration of the experiment.

Twenty-four hours after the addition of virus, cells were harvested, lysates were generated by sonication and analyzed for the β-galactosidase expression (i.e., β-galactosidase activity) and virus DNA as described in the preceding examples. Hirt extracts were prepared from low molecular weight DNA from cell extracts. The preparation of the Hirt extracts and subsequent analysis by Southern hybridization were performed similarly to those described in the examples above.

The results of this experiment were as follows:

(1) Specific Activity

The results are illustrated in the bar graph of FIG. 8A. Specific activity (milliunits β-galactosidase/mg protein) is plotted along the vertical axis. Below each bar is given the concentration of zinc used for induction, the fold-induction relative to 293 cells, and the fold-induction relative to 293(ORF6) cells maintained in the absence of zinc. As shown in FIG. 8A, in the absence of Zn+2, the 293(MT-ORF6) cell line generated 39-fold higher levels of β-galactosidase in rAAV infected 293 cells. Induction of ORF6 expression with increasing amounts of $Zn^{+2}$ resulted in a concomitant rise in AV.CMVLacZ cell transduction to a level that was 445-fold greater than the parent 293 line. Expression of E1 alone was insufficient to have an effect in the adenovirus mediated augmentation of rAAV transduction.

The specific activity of β-galactosidase was 196.2 mUnits/mg in E1/E4 expressing 293 cells, compared to 1.0 mUnit/mg in 293 cells that only expressed E1 genes. These experiments support a mechanism for enhancing rAAV transduction that is dependent on the combined expression of both E1 and E4 adenoviral genes.

(2) Molecular Analysis of the AV.CMVLacZ Genome

The duplex monomer replicative form (RFm) was quantitated and the values (CPM) plotted along the vertical axis in the bar graph of FIG. 8B. The concentration of zinc used for induction and the fold-induction relative to 293(ORF6) cells maintained in 0 mM zinc is given below each bar.

An autoradiogram (not pictured) shows the agarose gel resolved Hirt extracts from the AV.CMVLaCZ transduced cells described above. A plasmid carrying the AV.CMVLacZ cDNA was digested to release the entire sequence and loaded in a lane of the autoradiogram. The band that appeared in this lane therefore reflected the migration of a monomer duplex replicative form (RFm). The migration of the ss AV.CMVLacZ genome (SS), RFm, and dimers of the duplex replicative form (RFd) were also shown. Lanes of the autoradiogram labeled (0), (50), (100), (150), (200), and (250) contained samples from 293(MT-ORF6) cells that were induced with the indicated concentration of zinc. A Hirt extract from 293 cells (lane labeled 293) transduced with AV.CMVLacZ was also shown.

Analysis of Hirt extracts revealed the presence of the RFm in the rAAV infected 293(MT-ORF6) cells that was not present in similarly infected 293 cells. When the induction profiles (FIGS. 8A and 8B) that describe AV.CMVLacZ transduction efficiency were compared, the results were plotted in FIG. 8C. Specific activity (milliunits β-galactosidase/mg protein) data from FIG. 8A and counts-per-minute data (CPM) of AV.CKVLaCZ RFm from FIG. 8B are plotted along the vertical axis, and concentration of zinc sulfate used during the experiment is shown along the horizontal axis.

The two profiles are near mirror images. Importantly, the RFm increased in proportion to the increment in lacZ transducing activity that occurred as ORF-6 expression was induced with $Zn^{+2}$ (FIG. 8C). Similar results were obtained with a 293 derived cell line that expresses ORF6 from the glucocorticoid responsive MTv promoter.

Example 15

Enhanced AV.CMVLacZ Transduction in HeLa Cells Carrying an Inducible ORF6 Minigene HeLa(MT-ORF6) cells ($2 \times 10^6$) were transduced at an MOI of 1,000 AV.CMVLacZ recombinant particles/cell in absence of zinc sulfate inducer or in the presence of 50, 100, 150, 200, or 250 µM zinc sulfate inducer in the media during transduction. Twenty-four hours later, cells were harvested, cell extracts were prepared by sonication, and analyzed for transgene expression (i.e., β-galactosidase activity). Cell monolayers were histochemically stained for β-galactosidase activity.

The resulting photomicrographs (not pictured) illustrated that histochemical staining revealed an increase in the number of cells scored lacZ positive as the concentration of $Zn^{+2}$ in the medium was raised from 0 to 200 mM. Concentrations of 250 mM zinc were found to be toxic to the cells.

Figure 9:
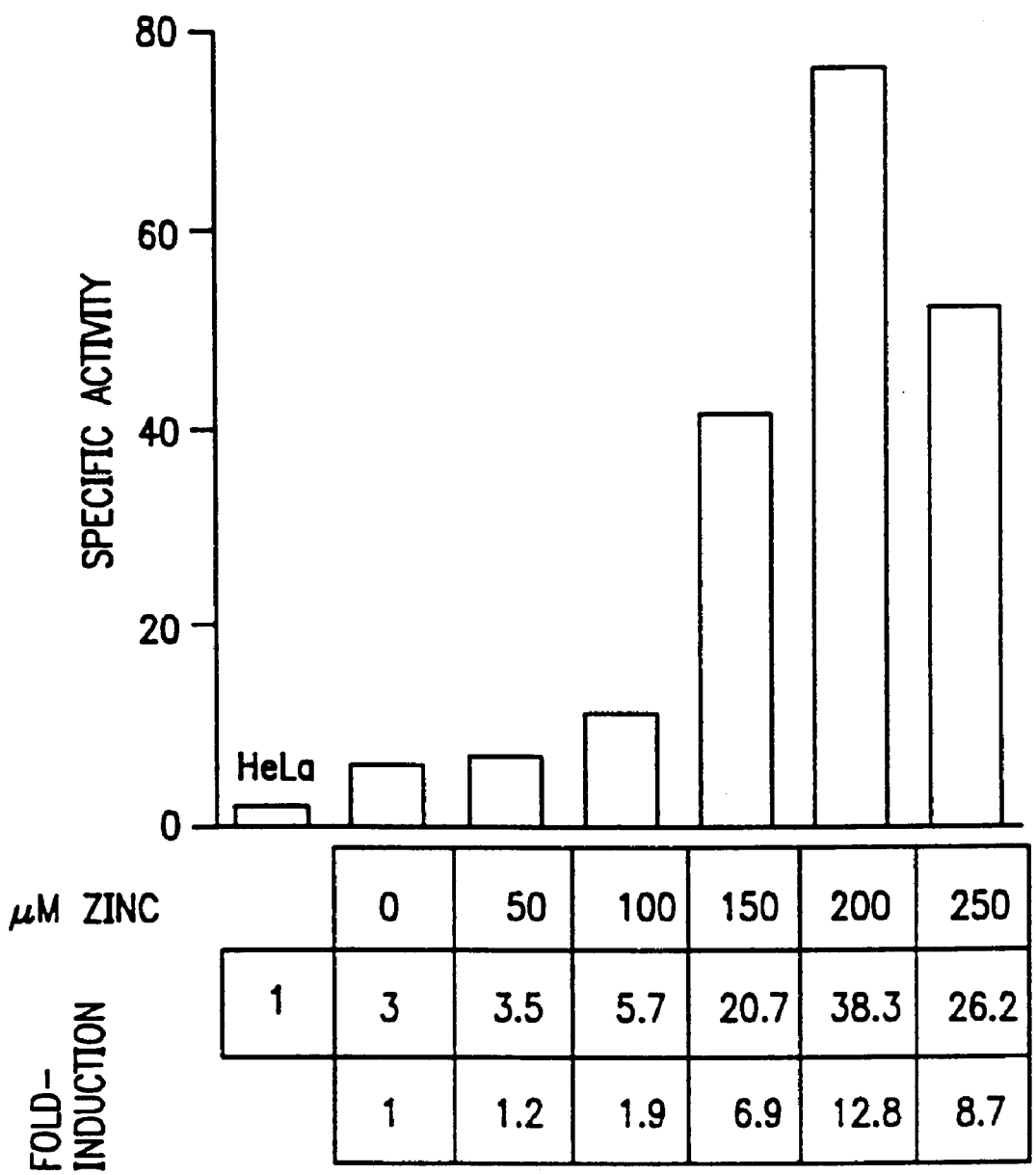
FIG. 9 is a bar graph plotting specific activity (milliunits β-galactosidase/mg protein) vs the concentration of zinc used for induction (first row under the horizontal axis), the fold-induction relative to Hela cells (second row), and the fold-induction relative to HeLa(Mt-ORF6) cells maintained in the absence of zinc (third row), for the HeLa(MT-ORF6) cells transduced at an MOI of 1,000 AV.CMVLacZ virus particles/cell in the absence of zinc sulfate inducer or in the presence of 50, 100, 150, 200 or 250 $\mu$M zinc sulfate inducer.

Specific activity (milliunits β-galactosidase/mg protein) is plotted in FIG. 9 along the vertical axis. Below each bar is given the concentration of zinc used for induction, the fold-induction relative to HeLa cells, and the fold-induction relative to HeLa(Mt-ORF6) cells maintained in the absence of zinc. Histochemical staining revealed an increase in the amount of β-galactosidase in lysates as the concentration of $Zn^{+2}$ in the medium was raised from 0 to 200 mM.

Example 16

Southern Blot Analysis of Low Molecular Weight DNAs from AV.CMVLacZ Transduced HeLa(MT-ORF6) Cells Following Induction of E4ORF6

Hirt extracts were prepared from HeLa(MT-ORF6) cells transduced with AV.CMVLacZ as described in Example 15 in the presence of increasing concentrations of $Zn^{+2}$ to determine whether synthesis of duplex intermediates contributed to the augmentation in AV.CNVLacZ transduction.

Samples of HeLa(MT-ORF6) cells that were induced with a concentration of zinc sulfate (0, 50, 100, 150, 200, and 250) were resolved on a 1.2% agarose Southern gel (not pictured), transferred to a nylon membrane, and hybridized with a LacZ-specific probe. One lane contained a plasmid encoding AV.CMVLacZ that was digested to release the entire genome. Bands corresponding to the ss AV.CMVLacZ genome (SS), duplex monomers (RFm), and duplex dimers (RFd) were indicated on the gel.

Southern analysis indicated that Hela and uninduced Hela(MT-ORF6) cells demonstrated a single band on Southern blots which comigrated with the ss genome. Induction of ORF-6 resulted in the appearance of detectable levels of ds monomer but only at higher concentrations of Zn+2. A band comigrating with the RFd was present in all cell preparations, the relevance of which is unclear since the monomer is a likely precursor to the dimer.

Example 17

Effect of Adenovirus Infection on In Vivo AV.CMVLacZ Taraeting Efficiency To Murine Liver The impact of adenoviral gene expression on rAAV transduction in murine liver was studied by sequentially infusing into the portal vein early gene mutants of adenovirus followed by rAAV.

Balb/c mice, 4- to 6-weeks old (Jackson Laboratories, Bar Harbor, Me.] were anesthetized by an intraperitoneal injection of ketamine (70 mg/kg) and xylazine (10 mg/kg). For liver studies, a 1 cm left flank incision was made and the spleen exposed.

Samples of purified, heat-treated AV.CNVLacZ in 50 $\mu$l HBS ($1 \times 10^{11}$ virus particles) were used alone or spiked with helper adenovirus containing $2 \times 10^{10}$ $A_{260}$ particles of purified dl1004, H5.CBALP, or ts125 in a final volume of 50 $\mu$l. The dose of adenovirus was sufficient to transduce >25% of hepatocytes. The virus mixture was injected just beneath the splenic capsule and the abdomen was closed with 3-0 vicryl.

Necropsies were performed 3 days post-infusion and tissue frozen in O.C.T. embedding compound. Frozen sections (6 $\mu$m) (LacZ+ALP) were prepared and histochemically stained for $\beta$-galactosidase enzyme and alkaline phosphatase activity. Sections were counterstained with neutral red and mounted.

A $\beta$-galactosidase positive hepatocyte targeted with AV.CMVLacZ at magnification 20X was obtained. Histochemical analyses of liver tissue harvested 3 days after gene transfer demonstrated that administration of $10^{11}$ particles of purified rAV.CMVLacZ alone into the portal vein was not associated with appreciable gene transfer (<0.01% of cells), confirming the inherent inefficiency of the rAAV system.

Preinfusion with E4 deleted virus had no impact on rAAV transduction in mouse liver, whereas E1 deleted virus demonstrated a modest increment in lacZ positive hepatocytes to about 0.1%. The most significant increase in rAAV transduction occurred following infusion of the E2a adenovirus mutant ts125 with lacZ expression detected in 10–25% of hepatocytes. A direct relationship between adenovirus gene expression and rAAV transduction was demonstrated in animals infused with both lacZ rAAV and the ALP expressing E1 deleted virus. The dose of adenovirus was reduced 10-fold to minimize the coincidental occurrence of coinfection. Histochemical studies demonstrated co-localization of ALP and $\beta$-galactosidase in the majority of $\beta$-galactosidase expressing hepatocytes.

Example 18

Effect of Adenovirus Infection on In Vivo AV.CMVLacZ Targeting Efficiency To Murine Lung Experiments described in Example 17 for mouse liver were adapted for the study of rAAV mediated gene transfer to mouse lung. For lung experiments, anesthetized Balb/C animals were intubated as described in DeMatteo et al, *Transplantation* (*Baltimore*), 59(5):787–789 (1995). Briefly, a midline 2 cm skin incision was made in the neck to expose the trachea. A 2 inch 18 gauge angiocatheter was passed through the mouth, positioned in the midportion of the trachea, and connected to a rodent ventilator (#55-3438 Harvard). Polyethylene (PE#10, Intramedic) was fed through the catheter via a side port and advanced beyond the tracheal bifurcation. Using a Hamilton syringe, virus samples (30 $\mu$l) were slowly infused into the lung through the polyethylene tubing. Samples contained the same formulation of purified, heat-treated AV.CMVLacZ with or without helper adenovirus, as described for liver injections.

Tissue was harvested 72 hours post-infusion. Frozen sections were histochemically stained for $\beta$-galactosidase activity and counterstained with neutral red.

Frozen sections from lung (AV.CMVLacZ) showed a $\beta$-galactosidase positive airway epithelial cell targeted with AV.CMVLaCZ. Similar studies were performed in the murine model of lung-directed gene transfer. Adenoviruses were instilled into the trachea prior to the instillation of rAAV. Analysis of lung tissue 3 days later revealed only a rare $\beta$-galactosidase positive cell in animals instilled with rAAV alone. No detectable enhancement of rAAV transduction was noted in animals preinstilled with adenovirus deleted of either E1 or E4. Substantial enhancement of transduction was achieved in conducting airway and alveolar cells of animals administered the E2a mutant adenovirus.

These experiments in murine models of gene therapy directed to liver and lung verified that the efficiency of rAAV transduction is low due limited conversion of the input ss genome to a transcriptionally active ds intermediate, and that this conversion is facilitated by expression of adenovirus E1 and E4 gene products.

Example 19

Second Generation rAAV with Regulated Minigene Capable of Enhancing Transduction The experiments described in previous examples illustrated the following principles: 1) purified rAAV is a relatively inefficient gene transfer vehicle in vitro and in vivo and 2) the rate limiting step in transduction is not viral entry but rather conversion of the virion's ss DNA genome to a transcriptionally active ds DNA genome. Adenovirus can substantially enhance transduction through expression of a subset of its genes. It does this by promoting conversion of the virion's genome to its ds form. One approach to accomplish this is to incorporate into the recombinant AAV genome a minigene that expresses the minimal adenoviral genes necessary to enhance transduction, i.e., the ORF6 region of E4.

Two approaches have been considered in designing this modified rAAV. The first strategy is based on a rAAV genome that has two transcriptional units in series, one expressing the therapeutic gene and the other expressing its E4 ORF6 from a constitutive promoter. While this may, in fact, be useful in many situations, constitutive expression of ORF6 may be detrimental to the cell and potentially could elicit a destructive immune response.

The second version of this rAAV includes the therapeutic minigene in addition to the ORF6 transcriptional unit which, in this case, is expressed from an inducible promoter. When this second gene rAAV is administered to the cells (ex vivo strategies) or to the patient (in vivo strategies), the inducing agents are administered at the time of gene transfer or soon thereafter. If the ds genomic form or its integrated derivative is stable, the induction of ORF6 will only be necessary at the time of gene transfer into the recipient cell. Following this, its inducing agent will be withdrawn and the ORF6 gene will be turned off.

Figure 11:
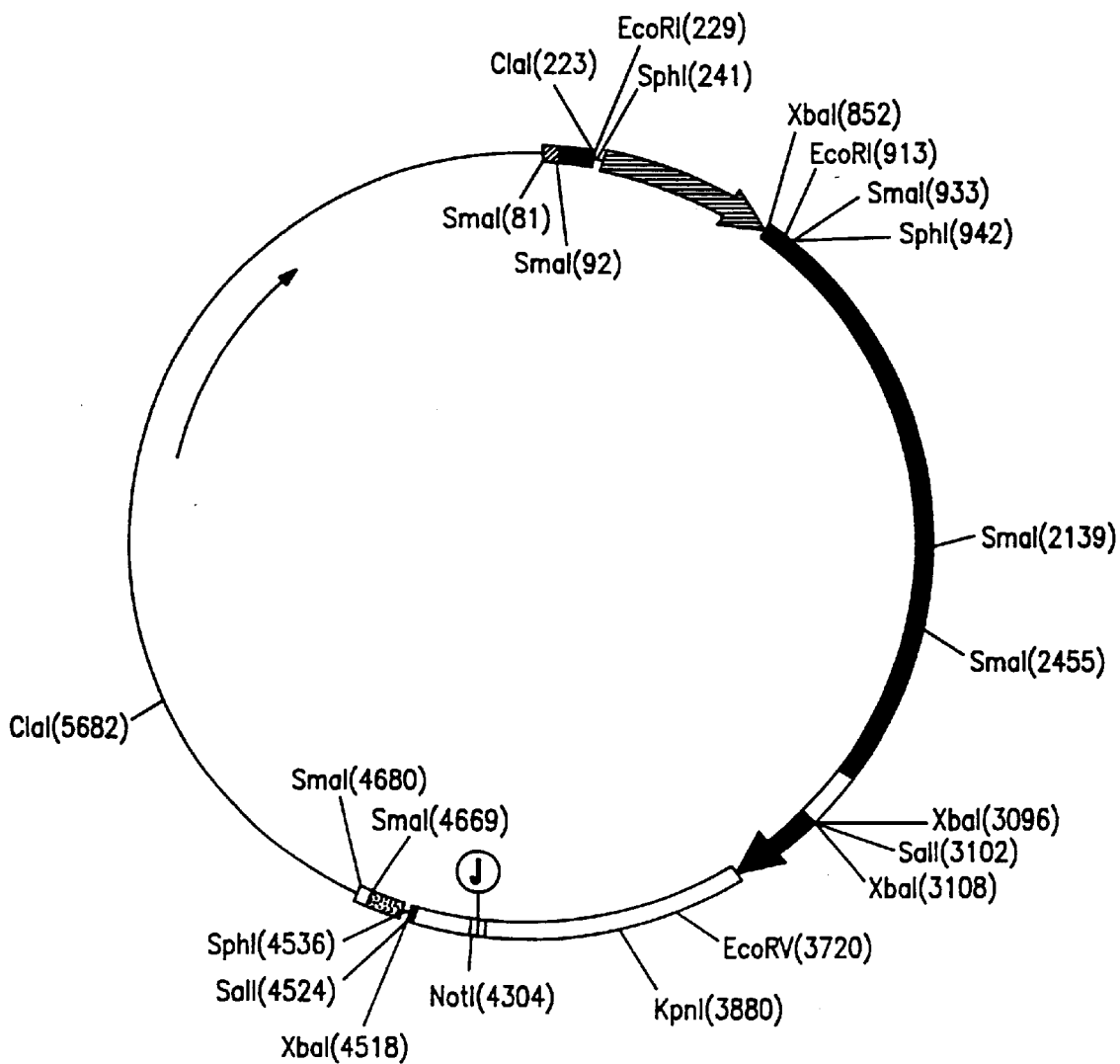
FIG. 11 illustrates plassid pAV.CMVALP.GRE-ORF6 [SEQ ID NO: 5].

An rAAV that illustrates this concept of inducible ORF6 has been constructed and tested in vitro. A schematic of the vector pAV.CMVALP.GRE-ORF6, is shown in FIG. 11 and its sequence is illustrated in SEQ ID NO: 5. This second generation construct contains flanking 5' and 3' AAV ITR sequences. The human placental alkaline phosphatase cDNA (ALP) is included in a minigene in which the promoter from the immediate early gene of cytomegalovirus drives the transcription. A second transcriptional unit is cloned between the ITRs in series and in direct orientation with the alkaline phosphatase minigene. The second transcriptional unit expresses the Ad5-E4-ORF6 from a glucocorticoid dependent promoter (GRE) with an SV40 polyadenylation signal. This is called a second generation rAAV construct.

Specifically, pAV.CMVALP.GRE-ORF6 [SEQ ID NO: 5] generates a novel rAAV containing the LaCZ transgene and the Ad E4 ORF 6 which facilitates ss to ds conversion of rAAV. The plasmid includes a flanking AAV 5' ITR sequence (nucs. 53–219); CKV enhancer/promoter (nucs. 255–848); human placenta alkaline phosphatase cDNA (ALP) (nucs. 914–2892); SV40 polyA (nucs. 2893–3090); GRE promoter (nucs. 3114–3393); Ads E4-ORF6 cDNA (nucs. 3402–4286); SV40 polyA (nucs. 4315–4512); and 3' AAV ITR (nucs. 4547–4713). All other nucleotides are plasmid derived.

The second generation rAAV construct was used to produce and purify rAAV virions which were exposed to HeLa cells that were left untreated or incubated with dexamethasone. In the absence of dexamethasone, (a condition under which little ORF6 should be expressed), little transduction was observed as measured by expression of the alkaline phosphatase gene. Cells incubated in dexamethasone expressed in ORF6 gene and the transduction efficacy was enhanced at least 5-fold. This provides evidence to support that a gene product expressed from the rAAV can function in cis to enhance expression of the transgene.

Example 20

Application to Bone Marrow Directed Gene Therapy

Bone marrow directed gene therapy represents the paradigm of ex vivo gene therapy where the target cell is the hematopoietic stem cell. The basic strategy is to incorporate (i.e., integrate) a therapeutic minigene into the chromosomal DNA of hematopoietic stem cells which are transplanted into a recipient patient whose own bone marrow has been ablated allowing repopulation of its lymphohematopoietic system with progeny of the genetically corrected stem cell.

The problem with this approach has been efficiently transfecting genes into stem cells. Most studies of bone marrow directed gene therapy have utilized recombinant retroviruses which have not been very efficient. One problem is that retroviruses integrate their provirus only when the target cell is dividing. Unfortunately, most stem cells in vitro are quiescent and not dividing. rAAV holds the promise of integrating the provirus more efficiently into non-dividing stem cells. However, purified rAAV is not very efficient with respect to integration when used alone. In cultured cells, integration is observed in less than 1% of the cells. The same conditions that activate the conversion of ss to ds genome also enhance the integration of the ds intermediate into the chromosomal DNA.

Therefore, a desirable application of the methods and compositions of this invention is in bone marrow directed gene therapy. According to this method, stem cells are genetically modified with rAAV and an inducing agent ex vivo using the constructs and methods described above (see e.g., Example 19). Genetically modified stem cells are subsequently transplanted by conventional techniques.

Numerous modifications and variations of the present invention are included in the above-identified specification and are expected to be obvious to one of skill in the art. Such modifications and alterations to the compositions and processes of the present invention, such as selections of different transgenes and plasmids for the construction of the packaging cell lines and rAds, or selection or dosage of the viruses or immune modulators, are believed to be encompassed in the scope of the claims appended hereto.

What is claimed is:

1. A method for enhancing the efficiency of transduction of a recombint AAV into a target cell comprising the steps of:
    infecting said target cell with a recombinant adeno-associated virus purified from contamination with adenovirus and comprising (a) adeno-associated virus inverted terminal repeat sequences necessary for transduction; and (b) a selected gene operatively linked to regulatory sequences directing its expression, wherein said gene is flanked by the sequences of (a); and
    introducing into said target cell a non-naturally occurring agent which delivers an adenovirus E4 gene product to said target cell, whereby said adenovirus E4 gene product enhances the efficiency of transduction of the recombinant AAV into the target cell.

2. The method according to claim 1 wherein said agent further delivers an adenovirus E1 gene product to the target cell.

3. The method according to claim 1 wherein said agent is a recombinant helper virus comprising the adenovirus E4 gene or a functional fragment thereof.

4. The method according to claim 1 where said non-naturally occurring agent is a DNA molecule comprising a DNA sequence encoding said adenovirus E4 gene product, said DNA sequence operatively linked to regulatory sequences which direct expression of said E4 gene product in said target cell.

5. The method according to claim 3 wherein said recombinant helper virus further comprises the adenovirus E1 gene or a functional fragment thereof.

6. The method according to claim 3 wherein said functional fragment of said E4 gene comprises the open reading frame 6 of E4.

7. The method according to claim 3 or 6 wherein said recombinant helper virus is an adenovirus.

8. The method according to claim 7, wherein said DNA molecule further comprises a DNA sequence encoding an adenovirus E1 gene product, said DNA sequence operatively linked to regulatory sequences which direct expression of said E1 gene product in said target cell.

9. The method according to claim 7 or 8 wherein said regulatory sequences directing expression of said adenovirus E4 gene product and/or said E1 gene product comprise a constitutive promoter.

10. The method according to claim 7 or 8 wherein said regulatory sequences directing expression of said adenovirus E4 gene product and/or said adenovirus E1 gene product comprise an inducible promoter, and wherein said cells are exposed to an inducing agent.

11. A method for enhancing the efficiency of transduction of a recombinant AAV into a target cell comprising infecting said target cell with a recombinant adeno-associated virus purified from contamination with advirus and comprising: (a) adeno-associated virus inverited terminal repeat sequences necessary for transduction; (b) a selected gene operatively linked to regulatory sequences directing expression of the selected gene product; and (c) an adenovirus E4 gene or a functional fragment thereof operatively linked to regulatory sequences which direct expression of an adenovirus E4 gene product, wherein said selected gene and said E4 gene or functional fragment are flanked by the sequences of (a), whereby said adenovirus E4 gene product enhances the efficiency of transduction of the recombinant AAV into the target cell.

12. The method according to claim 11, wherein said recombinant adeno-associated virus further comprises an adenovirus E1 gene or a functional fragment thereof operatively linked to regulatory sequences which direct expression of an adenovirus E1 gene product, wherein said E1 gene or functional fragment is flanked by the sequences of (a) in said target cell.

13. The method according to claim 11 wherein said functional fragment of E4 is the ORF6 sequence.

14. The method according to claim 11 wherein said regulatory sequences directing expression of said adenovirus E4 gene product comprise an inducible promoter, and cells are exposed to an inducing agent.

15. The method according to claim 11 wherein said regulatory sequences directing expression of said adenovirus E4 gene product comprise a constitutive promoter.

16. The method according to claim 12 wherein said regulatory sequences directing expression of said E1 gene product comprise an inducible promoter, and wherein said cell is exposed to an inducing agent.

17. The method according to claim 12 wherein said regulatory sequences directing expression of said adenovirus E1 gene product comprise a constitutive promoter.

18. A recombinant adeno-associated virus comprising:

(a) adeno-associated virus inverted terminal repeat sequences necessary for transduction;

(b) a selected gene operatively linked to regulatory sequences directing its expression; and (c) an adenovirus E4 gene or functional fragment thereof operatively linked to regulatory sequences which direct expression of an adenovirus E4 gene product, wherein said selected gene and said adenovirus E4 gene or fragment thereof are flanked by the sequences by the sequences of (a).

19. The recombinant adeno-associated virus according to claim 18 wherein said functional fragment is the ORF6 of E4.

20. The recombinant adeno-associated virus according to claim 18 wherein said regulatory sequences directing expression of said adenovirus E4 gene product comprise an inducible promoter.

21. The recombinant adeno-associated virus according to claim 18 wherein said regulatory sequences directing expression of said adenovirus E4 gene product comprise a constitutive promoter.

22. The reconibinat adeno-associated virus according to claim 18 further comprising an adenovirus E1 gene or functional fragment thereof operatively linked to regulatory sequences which direct expression of an E1 gene product, wherein said E1 gene or functional fragment is flanked by the sequences of (a).

23. The recombinant adeno-associated virus according to claim 22 wherein said regulatory sequences directing expression of said E1 gene product comprise an inducible promoter.

24. The recombinant adeno-associated virus according to claim 22 wherein said regulatory sequences directing expression of said E1 gene product comprise a constitutive promoter.

25. A mammalian cell transduced with the recombinant adeno-associated virus of any one of claims 18–24.

* * * * *

UNITED STATES PATENT AND TRADEMARK OFFICE
CERTIFICATE OF CORRECTION

PATENT NO. : 6,261,551 B1
DATED : July 17, 2001
INVENTOR(S) : James M. Wilson

It is certified that error appears in the above-identified patent and that said Letters Patent is hereby corrected as shown below:

Column 1,
Line 14, delete "+gi"
Line 49, replace "adenovirus-transforned," with -- adenovirus-transformed --.

Column 3,
Line 57, replace "The symbols are an" with -- The symbols are as --.

Column 6,
Line 18, replace "(HERK)" with -- (HEK) --.
Line 27, replace "calls" with -- cells --.
Line 29, replace "call" with -- cell --.

Column 10,
Line 12, replace "51" with -- 5' --.
Line 23, replace "rAds" with -- rAd --.
Line 25, replace "rAds" with -- rAd --.
Line 40, replace "plassid" with -- plasmid --.

Column 12,
Line 7, replace "overcoxe" with -- overcome --.
Line 11, replace "in" with -- is --.
Line 27, replace "In" with -- in--.
Line 47, replace "ant" with -- art --.
Line 53, replace "rAAVS" with -- rAAVs --.
Line 61, replace "vivo" with -- ex vivo --.

Column 13,
Line 11, replace "as" with -- ss --.
Line 12, replace "as" with -- ss --.
Line 44, replace "gone" with -- gene --.
Line 44, replace "as" with -- ss --.

Column 15,
Line 30, replace "as" with -- ss --.
Line 53, replace "as" with -- ss --.

UNITED STATES PATENT AND TRADEMARK OFFICE
CERTIFICATE OF CORRECTION

PATENT NO.    : 6,261,551 B1
DATED         : July 17, 2001
INVENTOR(S)   : James M. Wilson It is certified that error appears in the above-identified patent and that said Letters Patent is hereby corrected as shown below:

Column 19,
Line 3, replace "Expressina" with -- Expressing --.
Line 7, replace "Ads" with -- Ad5 --.
Line 56, replace "Ads" with -- Ad5 --.
Line 66, replace "plasaid" with -- plasmid --.

Column 20,
Line 46, replace "Ban" with -- Bam --.
Line 46, replace "HI-Bc1I" with -- HI-BclI --.

Column 22,
Line 43, replace "AV.CNVLaCZ" with -- AV.CMVLacZ --.
Line 51, replace "MTV" with -- MMTV --.

Column 23,
Line 14, Example 4, replace "plaguing" with -- plaquing --.

Column 25,
Line 11, replace "21: 6196-6200" with -- 91: 6196-6200 --.
Line 49, replace, "H5.001CBLacZ" (1st occurrence) with -- H5.000CBLacZ --.

Column 27,
Line 28, replace "Ads" with -- Ad5 --.
Line 36, replace "Ads" with -- Ad5 --.
Line 41, replace "Ads" with -- Ad5 --.

Column 29,
Line 10, replace "50 ml" with -- µl --.
Line 26, replace "AV.CNVLacZ" with -- AV.CMVLacZ --.
Line 50, replace "diners," with -- dimers --.

Column 30,
Line 51, replace "Rpm" with -- Rfm --.
Line 54, replace "calls" with -- cells --.

Column 32,
Line 16, replace "AV.CKVLaCZ" with -- AV.CMVLacZ --.
Line 25, replace "Mtv" with -- MMTV --.

UNITED STATES PATENT AND TRADEMARK OFFICE
CERTIFICATE OF CORRECTION

PATENT NO. : 6,261,551 B1
DATED : July 17, 2001
INVENTOR(S) : James M. Wilson

It is certified that error appears in the above-identified patent and that said Letters Patent is hereby corrected as shown below:

<u>Column 33,</u>
Line 21, Example 17, replace "Taraeting" with -- Targeting --.
Line 33, Example 17, replace "AV.CNVLacZ" with -- AV.CMVLacZ --.

<u>Column 35,</u>
Line 32, "CKV" with -- CMV --.
Line 35, "Ads" with -- Ad5 --.

<u>Column 97,</u>
Line 28, replace "advirus" with -- adenovirus --.

Signed and Sealed this

Twenty-fifth Day of June, 2002

Attest:

JAMES E. ROGAN
Attesting Officer   Director of the United States Patent and Trademark Office